United States Patent
Kopf-Sill et al.

(10) Patent No.: US 6,524,790 B1
(45) Date of Patent: Feb. 25, 2003

(54) APPARATUS AND METHODS FOR CORRECTING FOR VARIABLE VELOCITY IN MICROFLUIDIC SYSTEMS

(75) Inventors: Anne R. Kopf-Sill, Portola Valley; Andrea W. Chow, Los Altos; Claudia B. Cohen, Palo Alto; Steven A. Sundberg, San Francisco; John Wallace Parce, Palo Alto, all of CA (US)

(73) Assignee: Caliper Technologies Corp., Mountain View, CA (US)

( * ) Notice: Subject to any disclaimer, the term of this patent is extended or adjusted under 35 U.S.C. 154(b) by 0 days.

(21) Appl. No.: 09/093,542

(22) Filed: Jun. 8, 1998

Related U.S. Application Data
(60) Provisional application No. 60/049,013, filed on Jun. 9, 1997, and provisional application No. 60/076,468, filed on Mar. 2, 1998.

(51) Int. Cl.[7] .......................... C12G 1/68; G01N 21/00; G01N 33/558; G01F 5/00; G01P 3/36

(52) U.S. Cl. ................. 435/6; 435/6; 435/7.9; 435/287.1; 435/287.2; 435/288.3; 435/288.4; 435/288.7; 435/810; 435/7.1; 435/7.21; 436/4; 436/6; 436/514; 436/501; 436/518; 436/527; 436/519; 436/531; 436/535; 436/149; 436/150; 436/151; 436/164; 436/165; 436/172; 436/805; 436/809; 422/50; 422/68.1; 422/55; 422/57; 422/58; 422/82.01; 422/52; 422/82; 422/82.09; 422/73; 422/102; 422/119; 422/108; 422/182.8; 422/182.9; 204/400; 204/403; 204/193; 204/194; 204/409; 204/412; 204/455; 204/451; 204/601; 210/451; 210/505

(58) Field of Search ................ 435/7.9, 287.1, 435/287.2, 288.3, 288.4, 288.7, 810, 7.1, 7.21; 436/4, 6, 514, 501, 518, 527, 519, 531, 535, 149, 150, 151, 164, 165, 172, 805, 809; 422/50, 68.1, 55, 57, 58, 82.01, 52, 82, 82.09, 73, 102, 119, 108, 182.8, 182.9; 204/400, 403, 93, 194, 409, 412, 455, 451, 601; 210/451, 505

(56) References Cited

U.S. PATENT DOCUMENTS
4,390,403 A  6/1983  Batchelder (List continued on next page.)

FOREIGN PATENT DOCUMENTS
WO  WO 96/04547  * 2/1996  .......... G01N/27/00

(List continued on next page.)

OTHER PUBLICATIONS
Sutton et al., "A novel instrument for studying the flow behavior of erythrocytes through microchannels simulating human blood capillaries"., Microvascular Research, 53, 272–281, (1997).*

(List continued on next page.)

*Primary Examiner*—Christopher L. Chin
*Assistant Examiner*—Lisa V. Cook
(74) *Attorney, Agent, or Firm*—Matthew B. Murphy; Jonathan Alan Quine; The Law Offices of Jonathan Alan Quine

(57) ABSTRACT

Electrokinetic devices having a computer for correcting for electrokinetic effects are provided. Methods of correcting for electrokinetic effects by establishing the velocity of reactants and products in a reaction in electrokinetic microfluidic devices are also provided. These microfluidic devices can have substrates with channels, depressions, and/or wells for moving, mixing and monitoring precise amounts of analyte fluids.

50 Claims, 26 Drawing Sheets

U.S. PATENT DOCUMENTS

| | | | |
|---|---|---|---|
| 4,908,112 A | | 3/1990 | Pace |
| 5,126,022 A | | 6/1992 | Soane et al. |
| 5,223,219 A | * | 6/1993 | Subramanian et al. ........ 422/55 |
| 5,316,630 A | * | 5/1994 | Dasgupta .................... 204/180 |
| 5,442,169 A | * | 8/1995 | Kunz .................... 250/227.21 |
| 5,498,392 A | | 3/1996 | Wilding et al. |
| 5,526,109 A | * | 6/1996 | Johnson ..................... 356/28.5 |
| 5,571,410 A | | 11/1996 | Swedberg et al. |
| 5,585,069 A | | 12/1996 | Zanzucchi et al. |
| 5,593,838 A | | 1/1997 | Zanzucchi et al. |
| 5,599,432 A | * | 2/1997 | Manz et al. ................ 204/451 |
| 5,603,351 A | | 2/1997 | Cherukuri et al. |
| 5,635,358 A | | 6/1997 | Wilding et al. |
| 5,637,458 A | * | 6/1997 | Frankel .......................... 435/6 |
| 5,637,469 A | | 6/1997 | Wilding et al. |
| 5,750,015 A | | 5/1998 | Soane et al. |
| 5,779,868 A | | 7/1998 | Parce et al. |
| 5,800,690 A | | 9/1998 | Chow et al. |
| 5,852,495 A | | 12/1998 | Parce |
| 5,869,004 A | * | 2/1999 | Parce et al. |
| 5,876,675 A | | 3/1999 | Kennedy |
| 5,880,071 A | | 3/1999 | Parce et al. |
| 5,882,465 A | | 3/1999 | McReynolds |
| 5,885,470 A | | 3/1999 | Parce et al. |
| 5,942,443 A | * | 8/1999 | Parce et al. |
| 5,948,227 A | * | 9/1999 | Dubrow |
| 5,955,028 A | | 9/1999 | Chow |
| 5,957,579 A | | 9/1999 | Kopf-Sill et al. |
| 5,958,203 A | | 9/1999 | Parce et al. |
| 5,958,694 A | | 9/1999 | Nikiforov |
| 5,959,291 A | | 9/1999 | Jensen |
| 6,046,056 A | * | 4/2000 | Parce et al. ................. 436/514 |

FOREIGN PATENT DOCUMENTS

| | | |
|---|---|---|
| WO | WO 9702357 | 1/1997 |
| WO | WO 98/00231 | 1/1998 |
| WO | WO 98/00705 | 1/1998 |
| WO | WO 98/00707 | 1/1998 |
| WO | WO 98/02728 | 1/1998 |
| WO | WO 98/05424 | 2/1998 |
| WO | WO 98/22811 | 5/1998 |
| WO | WO 98/45481 | 10/1998 |
| WO | WO 98/45929 | 10/1998 |
| WO | WO 98/46438 | 10/1998 |
| WO | WO 98/49548 | 11/1998 |
| WO | WO 98/55852 | 12/1998 |
| WO | WO 98/56956 | 12/1998 |
| WO | WO 99/00649 | 1/1999 |
| WO | WO 99/10735 | 3/1999 |
| WO | WO 99/12016 | 3/1999 |
| WO | WO 99/16162 | 4/1999 |
| WO | WO 99/19056 | 4/1999 |
| WO | WO 99/19516 | 4/1999 |
| WO | WO 99/29497 | 6/1999 |
| WO | WO 99/56954 | 11/1999 |

OTHER PUBLICATIONS

Cohen, C.B. et al., "A Microchip–Based Enzyme Assay for Protein Kinase A", *Anal. Chem.* (1999) 273:89–97.

Dasgupta, P.K. et al., "Electroosmosis: A Reliable Fluid Propulsion for Flow Injection Analysis," *Anal Chem.* (1994) 66:1792–1798.

Jacobson, S.C. et al., "Fused Quartz Substrates for Microchip Electrophoresis," *Anal. Chem.* (1995) 67:2059–2063.

Manz, A. et al., "Electroosmotic pumping and electrophoretic separations for miniaturized chemical analysis systems," *J. Micromech. Microeng.* (1994) 4:257–265.

Ramsey, J.M. et al., "Microfabricated chemical measurement systems," *Nature Med.* (1995) 1:1093–1096.

Seiler, K. et al., "Planar Glass Chips for Capillary Electrophoresis: Repetitive Sample Injection, Quantitation, and Separation Efficiency," *Anal. Chem.* (1993) 65:1481–1488.

Seiler, K. et al., "Electroosmotic Pumping and Valveless Control of Fluid Flow Within a Manifold of Capillaries on a Glass Chip," *Anal. Chem.* (1994) 66:3485–3491.

* cited by examiner

APPARATUS AND METHODS FOR CORRECTING FOR VARIABLE VELOCITY IN MICROFLUIDIC SYSTEMS

CROSS REFERENCE TO RELATED APPLICATIONS

This application is a continuation-in-part of U.S. Ser. No. 60/049,013 filed Jun. 9,1997 entitled "APPARATUS AND METHODS FOR CORRECTING FOR ELECTROKINETIC EFFECTS IN MICROFLUIDIC SYSTEMS" by Kopf-Sill and Parce and U.S. Ser. No. 60/076,468 filed Mar. 2, 1998 "HIGH THROUGHPUT SCREENING APPLICATIONS OF MICROFLUIDIC SYSTEMS" by Cohen et al.; the present application claims priority to each of these applications and incorporates each of the applications herein in their entirety for all purposes.

FIELD OF THE INVENTION

The present invention provides microfluidic apparatus, methods and integrated systems for the separation and analysis of reaction components, fluid velocities, component velocities and reaction rates. Exemplary software is provided.

BACKGROUND OF THE INVENTION

There exists a need for assay methods and associated equipment and devices that are capable of performing repeated, accurate assays that operate at very small volumes. U.S. Ser. No. 08/761,575 entitled "High Throughput Screening Assay Systems in Microscale Fluidic Devices" by Parce et al. (see also, U.S. Ser. No. 08/881,696) provides pioneering technology related to microscale fluidic devices, including electrokinetic devices. The devices are generally suitable for assays relating to the interaction of biological and chemical species, including enzymes and substrates, ligands and ligand binders, receptors and ligands, antibodies and antibody ligands, as well as many other assays.

In the electrokinetic devices provided by Parce et al., an appropriate fluid is placed in a microchannel etched into a substrate having functional groups present at the surface. The groups ionize when the surface is contacted with an aqueous solution. For example, where the surface of the channel includes hydroxyl functional groups at the surface, protons can leave the surface of the channel and enter the fluid. Under such conditions, the surface possesses a net negative charge, whereas the fluid will possess an excess of protons, or positive charge, particularly localized near the interface between the channel surface and the fluid. By applying an electric field along the length of the channel, cations will flow toward the negative electrode. Movement of the positively charged species in the fluid pulls the solvent with them.

Improved methods and devices for monitoring reactions between chemical or biological species would be desirable. Electrokinetic microfluidic devices and assays using such devices are particularly desirable, due to the general adaptability of electrokinetic movement of small volumes of fluids to high throughput assay systems. The present invention fulfills these and a variety of other needs.

SUMMARY OF THE INVENTION

It has now been discovered that accurate determination of the reaction rate of a reaction conducted in a microscale fluidic device is facilitated by consideration of the velocity of the components in the reaction. In a microscale system in which the flux of reactants and reaction products is conserved, the velocity of at least one reactant or product is determined and the concentration of a reaction product is measured or calculated, facilitating determination of the reaction rate.

The concentration of products and reactants is typically measured at a selected position on the microscale fluidic device, e.g., spectrophotometrically, radioscopically, electrochemically, or optically. Velocity rates are optionally determined by measuring the speed of a component in a portion of the microscale fluidic device over time, or are determined by consideration of the parameters influencing velocity, e.g., the charge and mass of the component in an electric field. As described herein, methods of determining velocities are also provided in a constant flux state by indirect measurements, e.g., the velocity of a reactant or product can be determined by measuring a different reactant or product. Thus, any or all reactants or product velocities can be observed or determined. Velocity markers are also optionally used to approximate velocity. In one series of embodiments, electrokinetic devices and fluid injection schemes are described which self-correct for velocity effects on fluids.

A variety of reactants and products are assessed by these methods, including ligand and ligand binders such as an antibody and an antibody ligand, a receptor and a receptor ligand, biotin and avidin, proteins and complementary binding proteins, carbohydrates and carbohydrate binding moieties, nucleic acids, etc. Reactions which are monitored are fluorogenic or non-fluorogenic. A variety of microscale apparatus are adaptable to the methods such as microvalve and micropump arrangements, and particularly electrokinetic devices and the like. Multiple reactants and products are optionally assessed by serial or simultaneous detection methods or a combination thereof.

In one preferred class of embodiments, the microscale fluidic device provides for electrokinetic movement of reactants and products along a microfluidic channel. An electrokinetic microfluidic device is provided, having a microfluidic channel. An electric field is applied along the length of the microchannel, thereby causing charged species such as reactants, solvent molecules and products to move along the length of the channel due to electrophoretic flow, as well as by electroosmotic flow of the solvent in the channel. A first reaction component having a first charge mass ratio ($CM_1$) and a first velocity ($U_1$) is contacted to a second reaction component having a second charge mass ratio ($CM_2$) and a second velocity ($U_2$) in the microchannel, thereby permitting formation of a reaction product with a third charge mass ratio ($CM_p$) and a third velocity ($U_p$). Additional reaction components and products are optionally provided and assessed for velocities and concentrations. In one embodiment, a reactant can have a velocity of zero, e.g., because it is fixed to a substrate of the detection apparatus. However, the more typical case is for flowing reactants, where all reactants and products are flowing in channels of the system. Typically, the product has a velocity different from one or more reactants in the system.

Apparatus for practicing the methods of the invention are provided. For example, a microfluidic detection apparatus for determining the rate of formation of a moving analyte on an electrokinetic microfluidic substrate is provided. The apparatus has a microfluidic substrate holder for receiving a microfludic substrate during operation of the apparatus, having a microfluidic substrate viewing region. An analyte detector such as a phototube, photodiode, a charge coupled device, a camera, a microscope, a spectrophotometer, or the like is mounted proximal to the substrate viewing region to detect the moving analyte in a portion of the substrate viewing region. A computer operably linked to the analyte detector is provided. The computer determines the rate of formation of the analyte, correcting for the effects of the motion of the analyte, e.g., by determining or collating the velocities of one or more components and the concentrations of one or more components and calculating the rate of formation of one or more components, correcting for the velocity of the components. In preferred embodiments, the apparatus also includes an electrokinetic fluid direction system for moving fluids in the microfluidic substrate, such as one or more electrodes which fit into wells of the substrate, operably coupled to one or more electrical power supply.

Electrokinetic microfluidic devices are also provided. The devices have a substrate or body with a top portion, a bottom portion and an interior portion. The interior portion has at least two intersecting channels, with at least one of the two intersecting channels having at least one cross sectional dimension between about 0.1 $\mu$m and 500 $\mu$m. The device has an electrokinetic fluid direction system for moving an analyte through at least one of the two intersecting channels, a detection zone for detecting the analyte within at least one of the two intersecting channels, when the analyte is in motion, and a data detection device for detecting the analyte in the detection zone. A data analyzer which determines a rate of formation of the analyte in motion, such as a computer, is operably connected to the microfluidic device, e.g., with cables to the data detection device, or by recording data on the data collection device and transporting the recorded data (e.g., on a computer-readable storage medium) to the computer. Typically, the computer has appropriate software for determining reaction rates and other related information.

In one embodiment, at least two intersecting channels are etched in a top surface of the bottom portion, with the top portion being fused to the top surface of the bottom portion, thereby forming the interior portion disposed between the top portion and the top surface of the bottom portion. When heat lamination of glass or polymeric surfaces is performed, the glass or polymer fuses, typically with no seam existing between the top and bottom portion of the resulting microfluidic chip. In one preferred embodiment, the top portion of the device has a plurality of wells in fluid communication with the electrokinetic fluid direction system comprising an electrode adapted to fit into at least two of the plurality of wells. By applying an electric current with the electrode, solvent and analyte molecules are moved through the channels.

DEFINITIONS

Figure 1:
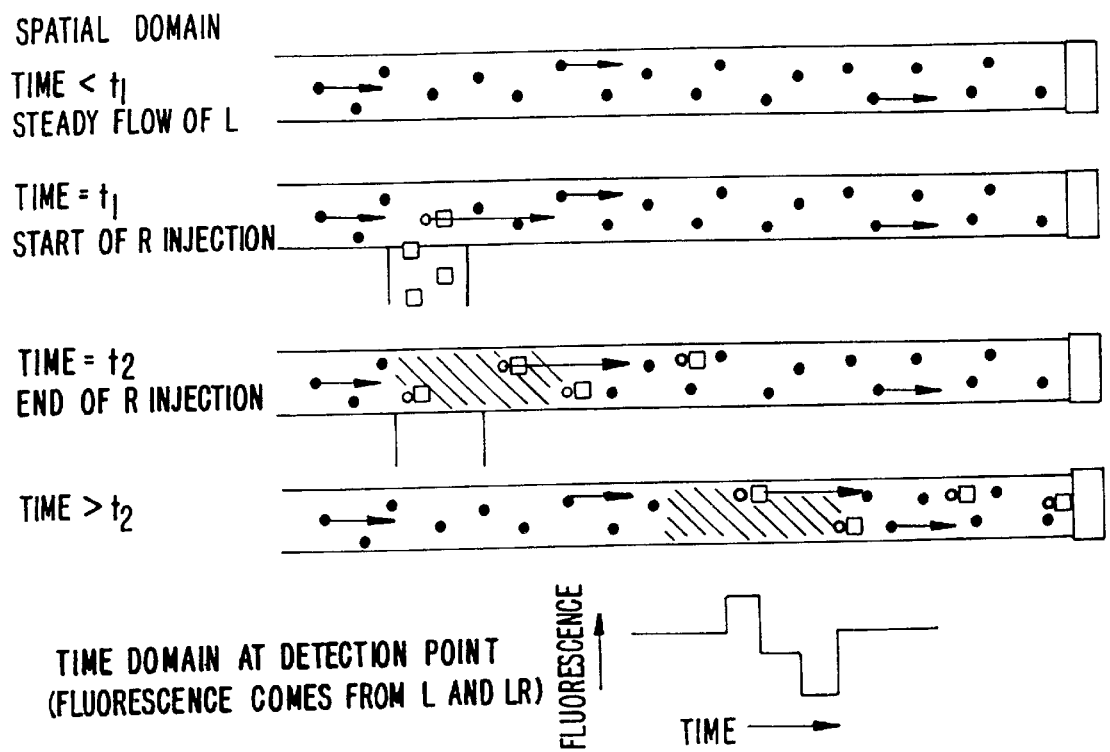
FIG. 1 is a schematic depiction of the basic concept of continuous flow non-fluorogenic binding assays on microchips showing changes in electrophoretic mobility over time and distance, including signal output.

Flux ("J") is equal to the velocity of analyte molecules (generally referred to herein as "U") times the concentration of the analyte molecules (generally referred to as "C") in a selected microfluidic system. Flux is "conserved" in a microfluidic system, such as a microchannel, when U times C is constant for a selected set of analyte molecules, such as reactants, products or both. For example, in a three component system, having a first reaction component with a mass concentration $C_1$ and a velocity $U_1$, a second reaction component with velocity $U_2$ and concentration $C_2$, and a product, with velocity $U_p$ and concentration $C_p$, flux is constant when $U_{1w}C_{1w}+U_{2w}C_{2w}+U_{pw}C_{pw}=U_{1z}C_{1z}+U_{2z}C_{2z}+U_{pz}C_{pz}$ where w is one point in the channel and z is a second point in the channel. An alternative notation is $[U_1C_1+U_2C_2+U_pC_p]_w=[U_1C_1+U_2C_2+U_pC_p]_z$. A more general notation that allows for multiple product (P) or reactant (R) species is:

$$\sum_{h=1}^{m} C_{R_h} U_h = \sum_{i=1}^{n} C_{P_i} U_i$$

where C is mass concentration (not molar concentration), m is the number of species before the reaction, and n is the number of species after the reaction. Thus, the sum of the mass concentration times the velocity of each of the species before a reaction is equal to the sum of the mass concentration times the velocity of each of the species after a reaction. In the cases when the reaction yields no net change in the total number of molecules, the molar flux as well as the mass flux are conserved.

"Velocity" typically refers to the distance a selected component travels (l) divided by the time (t) required for the travel. In many embodiments, the velocity under consideration is essentially constant, e.g., for the travel of reaction components along the length of a microchannel under a constant rate of current in an electrokinetic system. Although products of reactions typically change velocity as they are made from, or by, reactants, the velocity change is often considered to be instantaneous because the product reaches its terminal velocity in the system in a very short period of time. Thus, the velocity of a product is essentially constant immediately following formation of the product. Where the velocity changes significantly over time, due, e.g., to change of applied current in an electrokinetic system, or where a change from substrate to product results in a slow acceleration (or deceleration) in the system, an "instantaneous velocity" equal to the change in distance for a selected time ($\Delta l/\Delta t$) can be determined by graphing distance against time and taking the tangent of the resulting function at a particular point in time.

A "microfluidic" channel is a channel (groove, depression, tube, etc.) which is adapted to handle small volumes of fluid. In a typical embodiment, the channel is a tube having at least one subsection with a cross-sectional dimension of between about 0.1 $\mu$m and 500 $\mu$m; ordinarily, the channel is closed over a significant portion of its length, having top, bottom and side surfaces.

As used herein, "electrokinetic material transport systems" or "electrokinetic devices" include systems which transport and direct materials within an interconnected channel and/or chamber containing structure, through the application of electrical fields to the materials, thereby causing material movement through and among the channel and/or chambers, i.e., cations will move toward the negative electrode, while anions will move toward the positive electrode. Such electrokinetic material transport and direction systems include those systems that rely upon the electrophoretic mobility of charged species within the electric field applied to the structure. Such systems are more particularly referred to as electrophoretic material transport systems. Other electrokinetic material direction and transport systems rely upon the electroosmotic flow of fluid and material within a channel or chamber structure which results from the application of an electric field across such structures. In brief, when a fluid is placed into a channel which has a surface bearing charged functional groups, e.g., hydroxyl groups in etched glass channels or glass microcapillaries, those groups can ionize. In the case of hydroxyl functional groups, this ionization, e.g., at neutral pH, results in the release of protons from the surface and into the fluid, creating a concentration of protons at near the fluid/surface interface, or a positively charged sheath surrounding the bulk fluid in the channel. Application of a voltage gradient across the length of the channel, will cause the proton sheath to move in the direction of the voltage drop, i.e., toward the negative electrode. The steady state velocity of this fluid movement is generally given by the equation:

$$v = \frac{\epsilon \xi E}{4\pi \eta}$$

where v is the solvent velocity, $\epsilon$ is the dielectric constant of the fluid, $\xi$ is the zeta potential of the surface, E is the electric field strength, and $\eta$ is the solvent viscosity. The solvent velocity is, therefore, directly proportional to the surface potential. Use of electrokinetic transport to control material movement in interconnected channel structures was described in WO 96/04547 to Ramsey, which is incorporated by reference.

A "ligand" is a molecule which selectively binds or "hybridizes" to a "ligand binding partner". Many examples of ligands and ligand binding partners are known, including biotin and avidin or streptavidin, substantially complementary strands of nucleic acids, proteins and molecules bound by proteins (including cell receptors and cognate receptor binding molecules, antibodies and cognate antigens, etc.), proteins and "complementary proteins" (proteins which are specifically bound by other proteins, such as a cell receptor and a peptide which specifically binds the cell receptor), carbohydrates and carbohydrate binding molecules, engineered associating peptides and the like.

An "aqueous" solvent comprises primarily water, and optionally further comprises other chemical species, depending on the intended application, such as buffers, dyes, preservatives, or the like.

A "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence optionally includes the complementary sequence thereof.

An "antibody" is a polypeptide substantially encoded by an immunoglobulin gene or immunoglobulin genes, or fragments thereof which specifically bind and recognize an analyte ("antigen" or "antibody ligand").

A "label" is any composition detectable by spectroscopic, photochemical, biochemical, immunochemical, electrical, optical or chemical means. A "label moiety" is the detectable portion of the composition, e.g., the fluorophore, radioactive element or the like.

DETAILED DESCRIPTION

In some assays it is useful to determine the concentrations of products and related reaction rates for reactions in microfluidic devices. In standard laboratory devices where products or reaction rates are determined, such as cuvettes, or systems where reactants are delivered to reaction chambers, the analysis of reaction rates is straightforward, since all components of the reaction are maintained in one location. The reaction rate is related to the concentration of reagents and the time between the mixing of reagents and detection of the product. It has now been discovered that this simple analysis is not applicable to microfluidic systems in which reaction components and products have differing velocities through the channels of the device. Methods of determining the reaction kinetics in electrokinetic systems are provided.

In the case of electrokinetic movement of chemicals, the velocity of different chemical species in a single flowing system is not necessarily identical. Velocity for a particular component depends on the charge of the particular species, the size of the species, the solvent, and the like. For example, in a standard electrophoresis gel, analytes such as nucleic acids move through the matrix of the gel at different rates, depending on the size of the molecule and the charge of the molecule. Large molecules move more slowly in the matrix of the gel. Highly charged molecules have a greater attraction for an oppositely charged electrode than more modestly charged molecules, making more highly charged molecules travel toward an oppositely charged electrode with a higher velocity. These basic properties are understood, and form the basis for purification and analysis of biological and chemical molecules. However, mixing of components in such standard electrophoretic systems is not performed. No attempt is made during standard electrophoresis to determine reaction rates for the mixing of reactants. Accordingly, the special problems encountered during electrokinetic mixing were not considered in the electrophoretic art, and, of course, solutions to these unknown problems were not proposed.

In the special case of electrokinetic movement of fluids in a microfluidic device, different species are commonly mixed to form one or more product. Any or all of the reactant species or reaction products can have differing mobilities. Thus, for example, an enzyme can be reacted with a substrate which is modified to form a product. The substrate, modified substrate (i.e., product) and enzyme will often all have different mobilities. Detection equipment downstream from a reaction site in the microfluidic device will perceive the concentration of reactants and products based, in part, on the differing velocities of the components. For example, if an enzyme and a substrate are mixed at the start of a microchannel down which the components travel, the appearance of any product of the reaction downstream to the reaction site will depend on standard considerations such as the actual rate of the reaction (i.e., the number of product molecules made per unit time in the reaction), and the concentration of the reactants (until non-rate limiting amounts of reactants are provided, the more reactants provided, the faster the reaction will proceed—a simple result of chemical equilibrium). However, the perceived concentration of product downstream of the reaction site also depends on the velocity of the product. For example, if the velocity of the product is substantially slower than the velocity of the substrate in the system, then the product concentration will be substantially higher than the decrease in the substrate concentration that produced it. This is in contrast to the standard non-flowing system in which product concentration would be equal to the substrate that produced it. Thus, the reaction rates determined without consideration of velocities of the system components were discovered not to match results for reactions obtained by standard techniques, where the velocity of the components is zero (or at least not changing). Accordingly, the present invention relates to the discovery of a problem not previously known to exist, and to non-obvious solutions to this new problem.

Although the analysis of reaction rates in an electrokinetic system requires corrections for velocity changes, the value of determining reaction rates for many different concentrations in very short periods of time and in very small volumes of fluids makes the effort worthwhile. Accordingly, the present invention makes possible, for the first time, the accurate and simple analysis of accurate reaction kinetics in an electrokinetic system. The ability to assess reaction kinetics "on the fly" i.e., with the reaction occurring while the components have velocity relative to the observer, greatly speeds the rate at which such reactions can be assessed. This, in turn facilitates accurate high-throughout determination of reaction kinetics, and of a variety of other flowing interactions with applicability to drug screening, nucleic acid sequencing, enzyme kinetics, and the like.

Uses for Correcting for Electrokinetic Effects

It will be appreciated that the ability to quickly and accurately monitor and determine reaction kinetics has broad applicability to many different combinatorial approaches in biology and chemistry, for medical diagnostics, basic research, quality control, and the like. For example, the ability to correct for electrokinetic effects in microfluidic electrokinetic systems enhances the versatility of such systems. Any and all uses contemplated for electrokinetic systems can benefit from the present methods of correcting for electrokinetic effects.

The present methods and compositions are useful in measuring the rate of essentially any chemical or biological reaction, including particularly those which occur in an aqueous or other flowable solution. The methods are particularly desirable where repetitive screening of reactants is needed. This has general applicability to assessing the purity and activity of industrial and laboratory reagents (See, e.g., Kirk-Othmer Encyclopedia of Chemical Technology third and fourth editions, Martin Grayson, Executive Editor, Wiley-Interscience, John Wiley and Sons, NY, and in the references cited therein ("Kirk-Othmer") for a basic discussion of industrial chemical processes). Combinatorial screening of large libraries of compounds for biological activities provides the basis for finding new therapeutics. Thus, the ability to monitor the effect of compounds on biologically relevant reaction rates is of great importance and is of immediate commercial value to a variety of pharmaceutical, agricultural and chemical industries.

Similarly, the ability to rapidly and accurately screen large patient populations for evidence of infection, genetic disease, or the like, is typically performed by monitoring the interaction of chemical or biological components. For example, binding of HIV antigens to antibodies in a patient's blood is commonly used to detect whether a patient has been exposed to HIV. In a system in which the binding constant between the antibody and the relevant antigen can easily be monitored, it is possible to reduce the incidence of false-positives. Thus, the present invention provides for increased sensitivity in biological assays, as well as increased throughput.

In addition to monitoring antibody-antigen and other protein-protein interactions, it is possible to monitor the affinity of nucleic acid-nucleic acid interactions. This is particularly useful for empirically determining percent similarity for complementary related nucleic acids, and for detecting nucleic acids in various biological samples (including PCR samples; See, *PCR Protocols A Guide to Methods and Applications* (Innis et al. eds) Academic Press Inc. San Diego, Calif. (1990) (Innis)). As an alternative to standard solid state Southern or northern analysis (See, Sambrook, Ausubel, or Berger, supra.) the assay provides increased automation, a clear indication of the efficiency of nucleic acid hybridization (providing an increase in signal to noise ratios) and the like.

Monitoring reaction rates between enzymes and substrates has applicability as a general laboratory tool for basic research, where the reaction rate is unknown, and as a quality control tool for the assessment of the quality of reagents such as enzymes or substrates. And in diagnostic assays. Enzymes and other chemical and biological catalysts are in common use as components of foods, food supplements, detergents, therapeutics, and, e.g., as laboratory tools for recombinant nucleic acid manipulation (e.g., restriction enzymes, see, Berger and Kimmel, *Guide to Molecular Cloning Techniques, Methods in Enzymology* volume 152 Academic Press, Inc., San Diego, Calif. (Berger); Sambrook et al. (1989) Molecular Cloning—A Laboratory Manual (2nd ed.) Vol. 1–3, Cold Spring Harbor Laboratory, Cold Spring Harbor Press, NY, (Sambrook); and *Current Protocols in Molecular Biology,* F. M. Ausubel et al., eds., Current Protocols, a joint venture between Greene Publishing Associates, Inc. and John Wiley & Sons, Inc., (1994 Supplement) (Ausubel) for a discussion of some enzymes commonly used in molecular biology). Defective enzymes also serve as the direct cause for the etiology of many inherited diseases, including, e.g., ADA and phenylketonuria. The ability to screen enzymes rapidly from patients suffering enzyme defects is of considerable medical diagnostic value.

Methods of Correcting for Electrophoretic Effects

The present invention provides methods of accurately determining the rate of a chemical reaction. The reaction can be between two or more components that chemically join (by forming a covalent or non-covalent association) to form a new component or complex, or between a component such as an enzyme, catalyst or electromagnetic radiation that converts a first reactant or other component into a product, or due to spontaneous degradation of a component. In the methods, a first component and a second component are contacted, often by mixing, typically in a channel in an electrokinetic device. The components react to form a product.

Flux (J), with units of molecules/(cross sectional area× time) or mass/cross sectional area×time, is equal to the velocity of the molecules under consideration (U) times the concentration of molecules (C); thus, J=U×C. Flux is conserved in the microchannel. In other words, the number of analyte molecules (enzymes, substrates and products, or ligands and ligand partners) times the velocity of the components in a microchannel is constant along the channel.

The components and the solvent all travel along the length of the channel at different velocities to a position downstream of the mixing point where they are detected, typically by detecting a label (a variety of labels are described supra).

The velocity of one or more reaction components ($U_{r1}$, $U_{r2}$, $U_{r3}$ ...) or products ($U_{p1}$, $U_{p2}$, $U_{p3}$ ...) in the channel are determined. As explained in the examples below, in a system in which flux is conserved, if the velocity of one component is known, the velocities of the other components can be determined, given concentration information, charge mass ratios (ordinarily, the charge mass ratio (CM) is proportional to velocity in a flowing system, i.e., $U_{r1}$ is proportional to $CM_{r1}$, $U_{r2}$ is proportional to $CM_{r2}$, $U_3$ is proportional to $CM_{r3}$, $U_{p1}$ is proportional to $CM_{p1}$ ...), or the like. In some unusual instances, velocity (U) and charge mass ratios (CM) are not directly proportional due to unusual molecular shapes which either shield charge on portions of the molecules, or which cause molecular drag during electrophoretic motion.

In one convenient embodiment, the velocities of the reactants are known, either from direct measurement, or from previous measurements in a similar system, or by comparison to known velocity markers. Velocity markers are components which are run in the system which are detectable and known to have a particular velocity relative to an analyte. Measurement of the marker is used to estimate the velocity of the analyte (reactant, product or the like). The product velocity may be similarly known, or directly measured, e.g., by measuring the velocity of a detectable product over a section of the microchannel. Similarly, the velocities of the reactants can be measured over a section of the microchannel.

The concentration of the reaction product is determined in a portion of the microchannel. This determination can be done by measuring the number of molecules with the detector as described above, typically in a given section of an electrokinetic channel. Alternatively, the concentration can be determined indirectly, by measuring velocities and concentrations of other components in the system. Where flux is conserved, the sum of the concentration of reactants and products times the respective velocity of reactants and products is constant. Accordingly, the concentration of particular components can be measured, or determined from measurements for other components in the system, e.g., using simple algebra. For example, in a simple system having reactant 1 (R1) reactant 2 (R2) and a product (P) where J is constant, and $J=(U_{R1})[R1]+(U_{r2})[R2]+(U_p)C_P$, one of skill can easily determine $C_P$ where J is constant and $J=[U_1C_1+U_2C_2+U_PC_P]_w=[U_1C_1+U_2C_2+U_PC_P]_z$. By algebraic manipulation, $C_{Pz}=(U_1/U_p)(C_{1w}-C_{1z})+(U_2/U_p)(C_{2w}-C_{2z})+C_{Pw}$. Similar algebraic considerations can be used to yield the velocities or concentrations of other components where sufficient information is available. Linear algebra techniques are conveniently used to solve for the concentrations or velocities of components where there are multiple unknowns related in multiple flux relationships.

Given the velocity of a product ($U_p$) and the concentration of a product ($C_p$), it is possible to correctly determine the rate of a reaction. In particular, it is possible to determine the rate at which a product is formed, by conversion of one or more of the reactants into a product.

In the system in which one of the reactants aids in converting the other reactant into the product (e.g., where R1 is an enzyme or catalyst and R2 is a substrate), the following flux relationship can be used in determining a reaction rate: Flux $(J)=[R1]\times T_{LR2}\times k\times U_{R2}=[R2]_{converted}\times U_{R2}=U_p\times C_P$, where k is the turnover number for the enzyme reaction. Rearranging and writing transit time ($T_{LR2}$) of substrate as $L/U_{R2}$ results in: $[R1]\times L/U_{R2}\times k\times U_{R2}=U_p\times C_P$. Thus, [R1]/

$U_p \times L \times k = C_P$. Substituting transit time for product ($T_{LP}$) for $L/U_p$ gives the result that product concentration is proportional to the transit time of the product, not the substrate as might have been extrapolated from the stationary or non-mobility changing case above: $[R1] \times T_{LP} \times k = C_P$. Thus, $k = C_P/([R1]T_{LP})$. In one embodiment, where the product concentration before a reaction is zero and the enzyme concentration, R1 remains essentially constant, then, rearranging, $$C_P = ([R2]_{total} - [R2]_{unreacted})U_2/U_P.$$

Consideration of the case in which two or more components are joined to form a product is similar. When two reactants join, they typically result in a product with a different velocity than either of the two individual reactants (R1 and R2). With the flux being conserved, the concentration of detected species changes as a result of a change in velocity. The product optionally results in a different detectable label than either of the reactants, or can have the same label. Where R1 and R2 molecules are converted to P, taking the principle of the conservation of flux into account:

$$[R1] \times U_{R1} = C_P \times U_P$$

Recognition of this relationship allows quantification of the amount of R2 present in the system by detecting downstream fluorescence (all R2 is bound to R1). The relationship between the concentrations of R1 bound to R2 (i.e., forming P) and unbound R1 is proportional to their mobilities: $C_P = [R1] \times U_{R1}/U_P$.

At intermediate amounts of R2, where a portion of R1 is bound to R2, the concentration is proportional to the fraction ($Y_{R1}$) of R1 that is bound to R2:

$$C_P = Y_{R1}([R1]U_{R1}/U_P).$$

Without the knowledge that concentration changes as velocity changes, as taught herein, the assay is necessarily more complicated. For example, one could sample the mixture into a separation column which separated reacted and unreacted molecules, and detected florescence. The amount of material coming off of the column per unit time could be detected (see also, the Examples below). However, using conservation of flux, much simpler arrangements are possible. For instance, an electrokinetic system with one channel and two electrodes driving fluid flow in an electrokinetic device is used to monitor formation of reaction products.

It will be appreciated that products and reactants need not be fluorogenic (producing or quenching a fluorescent signal), but only need to be "velocitigeneic," i.e., a reaction need only produce a detectable change in velocity of a product compared to a substrate. This ability to sort signals based on the velocity of products as compared to reactants provides for the detection of multiple reactions and multiple products in a single electrokinetic device. Additional assays utilizing non-fluorogenic assays are described below.

A mass balance on the substrate of an enzyme reaction yields:

$$[S]_{total} = a[S]_{converted} + (1-a)[S]_{remaining},$$

where "a" is the fraction of substrate (S) that is converted to product. By definition, $[S]_{converted} = C_P$.

From the conservation of flux: $C_P = [S] \times U_s/U_P$. Therefore, $[S] = a[S]U_s/U_P + (1-a)[S]$. After measuring the signal before the reaction (l.h.s.) and after the reaction (r.h.s.), it is possible to solve for "a" if the velocity of substrate and product, $U_s$ and $U_P$, are known.

In many enzyme reactions, enzyme kinetics are studied in a range in which a very small portion of substrate is converted into product; in these cases, the substrate concentration can be treated as a constant. This makes the signal change due to formation of the product relatively small. To optimize the signal to noise ratio for observation of the product, it is possible to optimize electrokinetic flow so that the product velocity is slow (or close to zero) when the substrate velocity is relatively high, or to make product velocity fast while substrate mobility is slow.

When reactions are performed on microsubstrates with electrokinetic movement of solutions, the analysis of reaction rates and product formation is done from a starting point of conservation of flux. This is in contradistinction from prior art systems in which the velocities of reactants and products do not differ, permitting analysis from a simple standpoint of concentration balance. The present invention, therefore, provides for correct determination of reaction rates, a wider range of detectable reagents (e.g., velocitigenic, rather than flourescent), and simpler electrokinetic movement and detection apparatus.

Non-Fluorogenic Assays

The detection of results for many biochemical assays in conventional cuvette experiments, as well as in microfluidic devices has primarily been based on fluorogenic or chromogenic reactions in which the quantum efficiency of a labeling fluorescent moiety or the amount of colored label (chromophore) changes as a result of the reaction. However, for certain classes of assays the reactions are non-fluorogenic (i.e., there is no change in the quantum efficiency of the labeling fluorescent species upon reaction by the enzyme). As noted above, a reaction need only be velocitigenic for accurate rate determination; the formation of a new detectable element is not necessary in the practice of the invention.

It will be appreciated that the concepts described for non-fluorogenic assays are equally applicable for non-fluorescent systems, in which the label is other than a fluorophore, i.e., a colorimetric label, a radioactive label, an electrochemical label, or the like; for example, a non-chromogenic assay is an assay in which the color or intensity of a label does not change upon reaction; a non-radiogenic assay is an assay in which the radioactive component of the label is not modified by the reaction. Again, the relevant criterion is that a product have a different velocity than a reactant. For simplicity, fluorogenic assays and non-fluorogenic assays are discussed in more detail; it will be appreciated upon review of this disclosure that similar considerations apply for radio labels, chromophore labels, pH labels, ionic labels, or other common labels known to one of skill.

Detection of non-fluorogenic assays is possible in an electroosmotically driven microfluidic device using periodic injections of reaction mixture into a separation channel, in which reactants and products are separated by electrophoresis due to changes in the electrophoretic mobility resulting from the reaction, as discussed above (see also, A. R. Kopf-Sill, T. Nikiforov, L. Bousse, R. Nagel, & J. W. Parce, "Complexity and performance of on-chip biochemical assays," in *Proceedings of Micro- and Nanofabricated Electro-Optical Mechanical Systems for Biomedical and Environmental Applications,* SPIE, Vol. 2978, San Jose, Calif., February 1997, p. 172–179). The periodic injections are typically on the order of from about 0.0001 to 10 minutes, typically about 0.001 to 1 minute, often about 0.1 seconds to 10 second. See also, concurrently filed U.S. application Ser. No. 09/093489.

In an alternate non-fluorogenic continuous flow mode assays of the invention, the injection/separation step is eliminated. The binding reaction of fluorescently-labeled biotin to streptavidin was chosen as a model system for non-fluorogenic continuous flow mode.

The following discussion provides the basic concept of continuous flow non-fluorogenic assay on microchips, the use of conservation of flux to predict and interpret non-fluorogenic assay data quantitatively, modeling and experimental information to validate these concepts, applications of the format to biochemical assays on microchips, and the applicability of non-fluorogenic assays e.g., to high throughput drug screening.

The Continuous Flow Non-Fluorogenic Assay Format

In an electroosmotically driven microfluidic device, each type of dissolved species in a buffer moves down a channel at a velocity ($U_{tot}$) equal to the vector sum of the electroosmotic velocity of the buffer ($U_{eo}$) and the electrophoretic velocity of the molecule ($U_{ep}$):

$$U_{tot} = U_{eo} + U_{ep} = (\mu_{eo} \pm \mu_{ep})E.$$

In this equation, $\mu_{eo}$ and $\mu_{ep}$ are the electroosmotic mobility of the buffer and the electrophoretic mobility of the dissolved species, respectively, and E is the applied electric field. The electrophoretic mobility in turn depends on the charge-to-mass ratio of the molecule. In most biochemical reactions, the charge-to-mass ratio of the reactant molecule changes as a result of the reaction, thus changing the electrophoretic mobility of the molecules. This change in mobility, and therefore velocity, is the basis for detection of non-fluorogenic reactions in a continuous flow format.

Accordingly, methods of determining concentration of a reaction or assay product ($C_p$) in a channel of a microfluidic device are provided. In the methods, a labeled first reactant or assay component having a velocity ($U_r$) and a label ($L_r$), such as a fluorophore, chromophore or other label (see, supra for a discussion of labels) is flowed down a microfluidic channel and past a signal detector (detectors are also described supra). The labeled first reactant or assay component produces a signal ($S_{as}$) detectable by the detector. The labeled first reactant or assay component is converted to a reaction or assay product comprising a label $L_p$, the product having a velocity ($U_p$). In the typical case, ($U_r$) does not equal ($U_p$), resulting in a change in signal from $L_p$, thereby providing an indication of $C_p$. Because the assay is non-fluorogenic, $L_p$ comprises component elements of $L_r$ (i.e., the labels are typically essentially the same for the product and reactant, i.e., providing the same detectable output). Reactant or assay component signal ($S_{as}$ of a labeled first reactant or component prior to addition of a second reactive component, termed "$S_r$") can be subtracted from $S_{as}$ after the addition of additional components which react with the first reactant or component to provide a normalized signal ($S_n$) produced by the product.

In non-fluorogenic assays, a molecule comprising $L_p$ is converted from a molecule comprising $L_r$ by treating the molecule with any physical component or force which results in a modification of the molecule, including light, heat, electrical charge, a polymerization agent, a catalyst, or a binding molecule. $L_r$ and $L_p$ are optionally identical after the conversion, with only distal portions of the molecule being affected. Alternatively, $L_r$ can be modified so that a new label, $L_p$, is produced; however, the output of the label typically does not change in a non-fluorogenic assay. Of course, where the label does change, the concepts herein can also be applied, as the velocity will typically also concomitantly change.

The basic concept of the continuous flow mode of a non-fluorogenic assay can easily be illustrated with a schematic drawing of a binding reaction as shown in FIG. 1. In FIG. 1, the fluorescently-labeled reactant molecules are denoted by circles and the unlabeled reactant are denoted by squares. The reaction product molecules, denoted by the combined shape of a circle and a square, are shown lighter toned as a result of a binding reaction which, for the sake of simplifying this discussion, is fast and has a high association constant ($K_a$). ($K_a=[P]/[A][B]$ for a reaction A+B→P, where the brackets denote concentrations.) The labeled reactant (circles) flows continuously down the main channel at a constant concentration, whereas the unlabeled reactant (squares) is injected in a short pulse from a side channel into the main channel. In this illustration, the labeled reactant is assumed to move slow whereas the product moves fast (in the figure, motion is from left to right).

As the squares are injected into the main channel, they bind to the circles and convert them to fast moving molecules (for purposes of simplification, the binding is considered to be instantaneous). Downstream of the injection point, the faster moving product catches up with the slower reactant, giving rise to a higher local concentration of fluorescent species (i.e., the sum of labeled reactants and labeled products) ahead of the injection plug, and a lower concentration at the trailing end of the injection plug due to the depletion in reactants. Quantitatively, it is important to recognize that the product zone occupies a larger volume in the channel than the depleted reactant zone due to the higher product velocity. Consequently, the apparent concentration of product in the channel is less than the concentration of the reacted reactant, since the same number of molecules are now spread out in a larger volume. Interestingly, in the time domain as illustrated in the bottom of FIG. 1, the widths of the peak and valley are the same because the spatially wider product zone, which has been increased by a factor equal to the ratio of product velocity ($U_p$) to reactant velocity ($U_r$), moves past the detector faster by the same factor of $U_p/U_r$. If the concentration of the reacted reactant ($C_r$) and the velocities $U_r$ and $U_p$ are known, the concentration of the product ($C_p$) can be calculated as: $C_p=C_r (U_r/U_p)$. This equation makes use of the concept of conservation of flux (flux is defined as the product of velocity and concentration as discussed above).

When a label detector is placed downstream of the injection point (e.g., a photomultiplier tube, photo diode, or the like), depending on the distance between the injection and detection points, the length of the injection plug, and the species velocities, the plug of faster moving product can be partially or totally separated from the slower moving depletion hole of the reactant. In the case of partial separation, the detector signal ($S_{as}$) displayed in time will show a characteristic shape of a peak followed by a plateau region and a valley. The ratio of the magnitude of the peak to valley is ($C_p/C_r$), which, by algebraic manipulation, is equal to ($U_r/U_p$). The plateau region is lower in fluorescence than the background level. The ratio of the magnitude of the plateau region to the valley is $1-(C_p/C_r)$ or $1-(U_r/U_p)$. In the case of total separation, the signal shows a peak and a valley separated by the baseline fluorescence level instead of the plateau region.

Mobility Shift Modeling

For the case of a fast binding assay with a high $K_a$ (e.g., between about $10^5$ and $10^{15}$ or higher, typically higher than about $10^8 M^{-1}$ for a 1 μM concentration of reactants) as described in the last section, the fluorescence signal can easily be modeled in the time domain, e.g., using an Excel™ spreadsheet. Input parameters include reactant concentrations, electroosmotic mobility of the buffer, electrophoretic mobilities of the labeled reactant and product, distance between injection and detector locations, injection pulse time, and applied field strength. See, Appendix 1.

Figure 2:
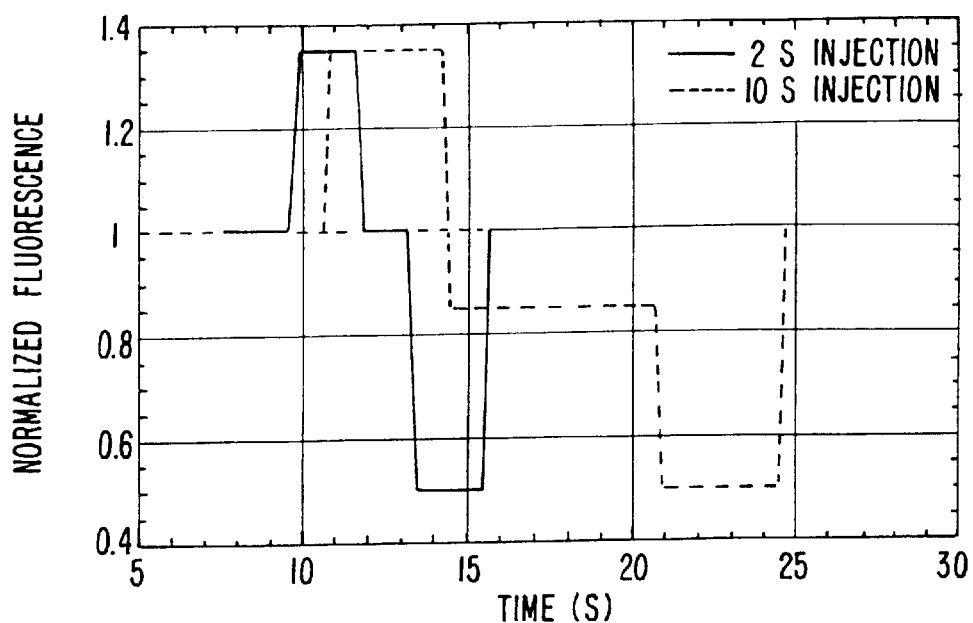
FIG. 2 is a graph providing model predictions of a non-fluorogenic binding assay with large association constant $K_a$.

Two cases of the model predictions are shown in FIG. 2. The first case, denoted by the solid curve in FIG. 2, is for a long injection time such that the signal peak and valley are only partially separated and a plateau region is clearly seen. The second case (dash curve) is for a short injection time such that the peak and valley are fully separated by the baseline fluorescence level. Note that in both cases, the magnitude of the peak height is smaller than the magnitude of the valley depth due to the principle of conservation of flux in flowing systems.

Figure 3:
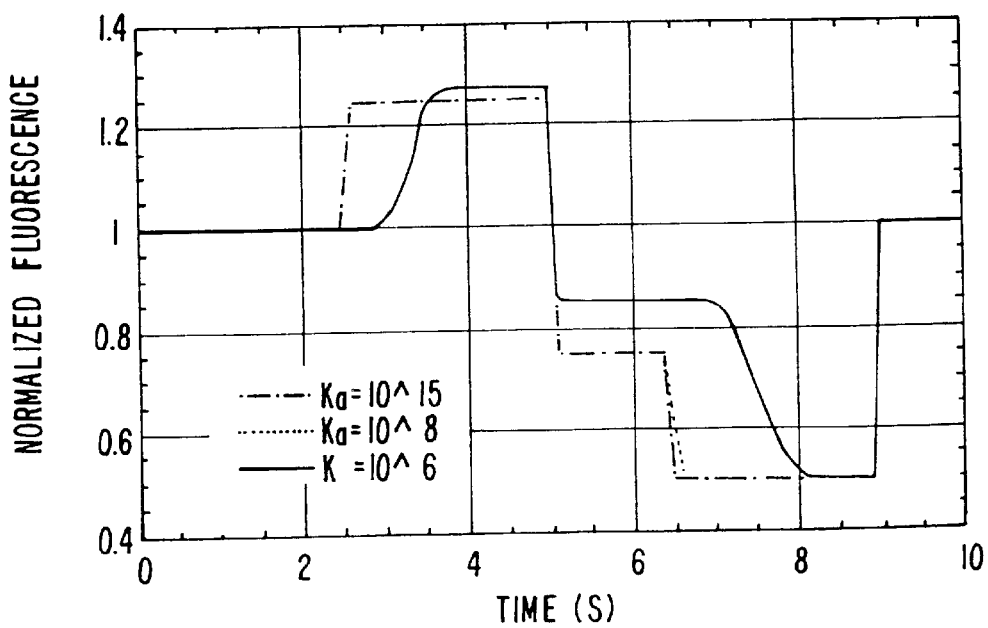
FIG. 3 is a graph providing model predictions of the fluorescence signal of a non-fluorogenic binding assay at three values of the association constant $K_a$.

For the more general case of a reaction with variable reaction rates and $K_a$ values, continuous flow non-fluorogenic assays can be modeled in the spatial domain. In one convenient embodiment, an Excel spreadsheet is again utilized. The basic construct of the spatial domain model is to split the channel into discrete sections spatially and in time. At an initial time, the channel is filled with the labeled reactant. For each subsequent time step, the second reactant is allowed to be injected into the channel and then reacted with the labeled reactant to form products at some prescribed reaction kinetics, which are required as input parameters. In this model, an algorithm is included to ensure that the concentration flux of each species moving down the channel is conserved. The Macro program listing, in Visual Basic Applications (VBA), for binding assays with variable $K_a$ values is included in Appendix A. FIG. 3 illustrates model predictions of the fluorescence signal at various values of $K_a$ when the concentrations of the reactants were chosen to be 1 $\mu$M.

Integrating Non-Fluorogenic Assays in High-Low Salt Format

In one series of high throughput screening embodiments, compounds of interest (e.g., potential drugs, or other analytes) are dissolved in a high salt buffer and placed in a source of materials, such as the wells of a microtiter dish, with a low salt buffer used as the running buffer to pipette the compounds from the wells into the planar LabChip™, e.g., through a capillary. A variety of source-chip arrangements and interfaces are described in Ser. No. 08/835,101 and CIP application Ser. No. 09/054,962 by Knapp et al. See also, U.S. Ser. No. 08/671,986. In brief, an electropipettor pipettor having one or several separate channels is fluidly connected to an assay portion of the microfluidic device (i.e., a microfluidic substrate having the reaction and/or analysis and/or separation channels, wells or the like). In one typical embodiment, the electropipettor has a tip fluidly connected to a channel under electroosmotic control. The tip optionally includes features to assist in sample transfer, such as a recessed region to aid in dissolving samples. Fluid can be forced into or out of the channel, and thus the tip, depending on the application of current to the channel. Generally, electropipettors utilize electrokinetic or "electroosmotic" material transport as described herein, to alternately sample a number of test compounds, or "subject materials," and spacer compounds. The pipettor then typically delivers individual, physically isolated, sample or test compound volumes in subject material regions, in series, into the sample channel for subsequent manipulation within the device. Individual samples are typically separated by a spacer region of low ionic strength spacer fluid. These low ionic strength spacer regions have higher voltage drop over their length than do the higher ionic strength subject material or test compound regions, thereby driving the electrokinetic pumping, and preventing electrophoretic bias. On either side of the test compound or subject material region, which is typically in higher ionic strength solution, are fluid regions referred to as first spacer regions (also referred to as high salt regions or "guard bands"), that contact the interface of the subject material regions. These first spacer regions typically comprise a high ionic strength buffer solution to prevent migration of the sample elements into the lower ionic strength fluid regions, or second spacer region, which would result in electrophoretic bias. The use of such first and second spacer regions is described in greater detail in U.S. patent application Ser. No. 08/671,986. These electropipettors are used to physically sample a source of materials of interest, such as a microtiter dish, a membrane having dried or wet samples disposed thereon (dry samples can be resolublized, e.g. by expelling fluids from the electropipettor followed by drawing the expelled fluid into the device; for other arrangements see Ser. No. 09/054,962) or the like.

In the high-low salt format, the electric field within the high salt region in the channel of a pipettor chip is relatively small compared to that in the low salt region, due to the lower electrical resistance of the high salt buffer. Consequently, electrophoresis of compounds in the high salt plug is greatly retarded, whereas the high salt plug itself is dragged along by electroosmosis driven primarily by the conditions in the low salt region.

At least two general approaches to integrate non-fluorogenic assays into this high-low salt pipettor chip format for high throughput drug screening—continuous flow mode and injection/separation mode are provided. In the continuous flow format, integration of the two opposing principles of preventing and encouraging electrophoresis at will into one simple chip design requires careful chip and experimental design. One method is to inject a buffer into the latter part of the main reaction channel to "spoil" the high-low salt format after the assay has had adequate incubation time to generate product.

Incorporating non-fluorogenic assays into the high-low salt format by injection followed by separation in another channel is likely to be less dependent on the buffer systems, and thus is general in its applicability to a wide range of biochemical assays. However, a control mechanism is used to time the injection. External control mechanisms to time the arrival of the high salt plug to trigger injection include use of an electromagnetic means such as an in-situ conductivity probe in the channel and/or optical methods based upon the intrinsic properties of the buffer (e.g., refractive index changes in high/low salt buffers), or placing a dye marker in the buffer in conjunction with using an optical detector to time the flow. Another method is to use the pressure developed at the interfaces of the high and low salt regions to induce injection at a channel intersection. In this case, the injection is automatic; no external control and feedback means is required. See also, concurrently filed U.S. application Ser. No. 09/093,489.

Continuous Flow Assay Formats Using Interference Patterns of Analyte Concentration Waves in Electrokinetic Microfluidic Systems Methods to enhance the detection of non-fluorogenic assays on chips for small mobility shifts are available. One approach is to inject the reaction mixture into a planar cyclic capillary electrophoresis channel to separate products from reactants. In this case, the separation time can be made very long by continuously cycling the voltage around the cyclic structure. Another method is to use the concept of interference of concentration waves in channels to enhance to the magnitude of peaks and valleys in the non-fluorogenic assay fluorescence signal (see, below).

Use of Concentration Waves for Data Correction

In a microfluidic device in which an electric field is applied along the length of the microchannel, charged species such as analytes, solvent molecules, reactants and products move along the microchannel by the electrokinetic forces of electroosmosis and electrophoresis. The net mobility of each species is determined by the vectorial sum of the electroosmotic and electrophoretic mobilities, the latter of which is a function of the hydrodynamic radius-to-charge ratio of each species. During a chemical or biological reaction such as ligand-receptor binding, antibody-antigen binding, etc., the reactants in general have different electrophoretic mobilities than those of the products. The differences in mobilities are useful for detection, e.g., of non-fluorogenic assays described above, in which reaction detection is not dependent on the production or quenching of fluorescence as a consequence of the reaction. Instead, the mobility difference during flow in the microchannel is used to separate the "reactant hole" (i.e., decrease in reactant concentration) of the labeled reactant from the "product peak" (i.e., increase in product concentration) under continuous flow, thereby providing a signature from which quantitative information on the reaction kinetics can be extracted from calculation methods based on conservation of species flux discussed supra. Non-fluorogenic assay formats are unique to electrokinetic microfluidic systems; there is no analogy for cuvette assays.

The invention provides methods for performing continuous flow assays in electrokinetic microfluidic devices to facilitate determination of reaction kinetics using the generation and detection of reactant and product "concentration waves" in microchannels. The reactant concentration wave is generated temporally by modulating the concentration of one or more reactants using electroosmotic pumping. The product/concentration wave is generated as a result of the reaction. At the point of reaction in the microchannel, the product wave is inherently 180° out-of-phase with the reactant wave. If the reaction is non-fluorogenic, a detection device placed very close to the point of reaction along the microchannel measures a constant signal (such as due to fluorescence of a labeling moiety covalently bonded to a reactant), since the sum of the signals from the labeled reactant and converted product is constant. Further downstream of the microchannel, however, the reactant and product waves separate spatially due to differences in electrophoretic mobility, and the reaction can be detected. The measured signal can be viewed as "interference" of the reactant and product waves, analogous to the phenomenon of interference of electromagnetic (such as optical) waves. The "phase shift" in the reactant and product waves is a function of the net mobility difference of the labeled reactant and product, the average flow velocity in the microchannel, and the distance from the point of reaction. At the point of reaction, the phase shift is zero and the waves interfere destructively. As the phase shift approaches 180°, the waves interfere constructively and the signal is maximized.

In studying the kinetics of a reaction in a microfluidic device, analyte concentration waves with a constant frequency and varying concentrations can be used to elucidate the dependence of kinetics on concentration (analogous to analyte titration). An "interference pattern" as a function of spatial position can be measured by placing the detector at different points along the microchannel. Deconvolving the interference patterns using wave equations, conservation of flux, and diffusion equations provides quantitative information on species mobilities and reaction kinetics.

In many cases when the mobility shift of the reactant and product is not known, a reactant concentration wave with varying frequencies can conveniently be used to study the reaction. For instance, the frequency of the reactant concentration wave can be increased linearly with time. A detector located at a fixed distance from the point of reaction can measure an increase in the signal intensity as the mobility-induced phase shift becomes a significant fraction of the wavelength of the concentration wave. Again, kinetics data can be obtained by deconvolving the signal using wave, diffusion, and flux conservation equations.

In general, this continuous flow assay format using interference patterns of analyte concentration waves can be applied to a wide range of assays. This format can be especially sensitive to small changes in the mobility shift of the converted product, such as in the case of ligand-receptor assay, in which the mobility of the protein-ligand complex is expected to differ little from that of the labeled protein of interest since the binding ligands are usually small molecules. The following is an example to illustrate the practicality and usefulness of this format. The reaction of interest is:

$$P+L \rightarrow PL$$

where P is a labeled protein with molecular weight of 10 to 100 kDaltons, L is a ligand with molecular weight of 50 to 500, and PL is the protein-ligand complex. If a concentration wave of an unlabeled ligand is electroosmotically pumped into a microchannel containing a constant concentration of the labeled protein, the binding reaction generates a complementary concentration wave of the labeled complex.

Assume for illustrative purposes that the electroosmotic (EO) mobility of the buffer is 0.4 $cm^2$/kV-s and the protein has an electrophoretic (EP) mobility of −0.2 $cm^2$/kV-s. If the EP mobility shift due to binding is only 1%, then the EP mobility of the complex is −0.202 $cm^2$/kV-s. In a nominal electric field of 250 V/cm along the microchannel, the velocities of the protein and complex is 0.5 and 0.495 mm/s, respectively. For a nominal channel distance of 20 mm between the point of reaction and detector location, the time for the protein and complex to arrive the detector is 40 and 40.4 s, respectively. The time difference is therefore 0.4 s between the 2 labeled species. If this time difference is a significant fraction of the wavelength to achieve noticeable constructive interference, say ¼ (or 90° in phase shift), then a ligand concentration wave of frequency 0.625 Hz (=1/(4× 0.4 s)) is needed. This frequency is practical compared to the response time of a typical electrical controller and a data acquisition rate of 20 Hz. Furthermore, for 0.5 mm/s velocity, this frequency is equivalent to ligand injection plugs of 800 μm per cycle spatially. This dimension is also reasonable when compared to a nominal detector window of ~50 μm, and a Brownian diffusion length of ~70 μm under the given flow conditions and the assumption of a protein diffusion constant of 6×10$^{-7}$ $cm^2$/s.

Constant Flux Microchip Injector in Quantitative Analysis

Essentially any analysis in which a starting compound is converted to a product with a different mobility can be analyzed in a microfluidic device of the invention. As noted above, essentially any velocitogenic assay can be analyzed. One exemplar class of velocitogenic assays includes enzymatic reactions. Kinases are a specific example of enzymes of this type. Kinases recognize specific polypeptide sequences and phosphorylate them. Phosphorylation changes the peptide charge, mass and structure, and thus the mobilities of the non-phosphorylated and phosphorylated species are different. As a consequence of this change in mobility, substrate and product move at different rates in an applied field.

Enzyme kinetics (i.e., the determination of kcat, Km, and Ki) may be performed in a microchip capillary electrophoresis experiment by determining the extent of conversion of substrate to product. Traditionally, kinetic analyses in a cuvette experiment are performed under conditions such that the reaction is not substrate limited and the enzymatic turnover is simply a function of the solution conditions and the inherent catalytic nature of the enzyme. Velocity is irrelevant in this format. In the microfluidic system, the reaction is homogeneous in that it occurs in the flowing stream in the capillary. There is typically no surface immobilization of reagents (as described supra, the special case where the velocity of a reagent is zero leads to special considerations). Reagents are typically pumped electrokinetically into a reaction channel. The field imposed on the flowing stream results in a separation of each species according to its mobility. In the case where the substrate concentration is high relative to the Km of the enzyme reaction, the amount of product produced does not depend on the concentration of substrate. The reaction rate depends only on the reaction conditions and the inherent enzyme reactivity. The signal generated in any unit volume is a function of the amount of enzyme in the reaction mixture, the reaction time, and the electrokinetic mobility of each species. Unlike the homogeneous cuvette experiment, the electrokinetic forces used in the microchip format to move reagents along the microchannels bias the species concentrations in a reaction. On a microchip, substrate and enzyme flow together through a capillary network, mix, and the substrate is converted to product as the reaction mixtures flows along the length of the mixing channel. Typically in fluorescence detection, the substrate and product species are both labeled with a fluorescent tag. After mixing, the reagents are pumped electrokinetically through a portion of the channel passing in front of the detector. Samples of the reaction mixture are analyzed quantitatively as substrate and product moieties are separated by their different electrokinetic mobilities either in the continuous flow mode as described above or by injection followed by separation in another channel.

In the injection/separation mode, one way to make injections in a microchip is in a cross or orthogonal injector. In this design, reagents flow in a fluid path along the length of the applied field. They mix and react as they flow along the channel. At some distance down the reaction channel, a perpendicular cross channel is encountered. Injections can be made from the reaction channel into the separation channel by modulating the voltages applied at the end of the capillary length. The injection volume is the volume mostly defined by the intersection of the orthogonal channels. The consequence of this type of injection is that the amount of reactants and products is a direct reflection of the concentrations in the reaction channel at the injection point. These concentrations are a function of the solution composition, the enzyme reactivity, the reaction time, and the electrokinetic mobilities of the reactants and products. Therefore, in order to determine the substrate and product concentrations, the relative mobilities of each reactant and product are determined. Kinetics constant determination requires electrokinetic correction using the relative mobilities of substrate and product as discussed herein.

Alternatively, an injector that compensates for the different mobilities of substrate and product in the microchip reaction mixture can be used. The gated injector is realized in the microchip design where the separation channel is collinear with the reaction channel. In this case, the electric field for electrokinetic pumping is applied along the axis of the reaction channel. The fluid mixture flows along this axis but it is directed off the main reaction channel into a side channel most of the time, with periodic injection into the collinear separation channel passing in front of the detector. Buffer or background electrolyte from another side channel flows through the separation channel between the injected aliquots from the reaction channel. The injections of reaction mixture into the separation channel are pulsed by voltage or current control. The bias imposed by the electric field pulsing aliquots of reaction mixture to the detector influences the rate at which reagents enter the separation channel. The result is that species of highest apparent mobility move fastest into the separation channel while the low mobility species travel slowly into the separation channel. This electrokinetic bias in the injection causes species that are concentrated in the reaction channel because they move relatively slowly to map out a smaller volume of injection into the separation channel.

Conversely, faster species that are diluted in the reaction channel map out a proportionately larger volume into the separation channel due to the higher velocity. Because the same electrokinetic forces that result in the concentrating and diluting of analyte concentrations in the reaction channel also cause the bias in the injection volumes for the gated injector, the collinear chip injector can be used to compensate for the effects of changes in mobility on the determination of the extent of reaction in microchips.

In a simple example in which a substrate with concentration Cs and velocity Us is partially converted by an enzyme to a product with concentration Cp and velocity Up, conservation of flux dictates that $J=C_p U_p=(yC_s)U_s$, where y is the fraction of substrate conversion. When this reaction mixture is injected through a gated injector into a separation channel, the length of the sample bands for the unconverted substrate ($L_s$) and for the product ($L_p$) are proportional to their respective velocities, $U_s$ and $U_p$. $L_s U_s$; $L_p U_p$. The total amount for each species in the injection volume is the concentration times the volume injected. If A is the cross-sectional area of the separation channel, then the total amount of unconverted substrate injected is (y $C_s)L_s A$, which is proportional to $(yC_s U_s)$. The total amount of product injected is $(C_p L_p A)$, which is proportional to $(C_p U_p)$. Consequently, the total amount injected for each species is representative of the flux of the species in the reacting channel. Thus, the result of using a gated injection is that the extent of chemical conversion can be determined accurately without further electrokinetic correction if the total amount of each species can be measured. A "total amount" detector can be accomplished by setting the detector window (such as a photomultiplier tube or PMT slit) spatially wider than the longest sample band length, resulting in peaks whose amplitude is proportional to the amount (as well as the concentration) one would measure in a non-flowing cuvette experiment. Other examples of detectors that report the total amount of reagent are ones based on total photobleaching and total charge upon complete electrochemical conversion. On the other hand, for "concentration" detectors such as a narrow PMT slit compared to the sample band lengths, the extent of reaction still requires the relative mobility correction as disclosed herein because the gated injector does not alter the species concentrations in the aliquot.

Accordingly, in one aspect, the invention provides methods for dispensing representative mixtures by gated injection. In the methods, a first fluidic mixture is introduced into a first microfluidic channel. The mixture has at least first and second materials; e.g., assay components, reactants or the like, and optionally comprises any number of additional reaction components. The first and second materials are transported through the first channel at different velocities, i.e., due to differences in charge/mass ratios, differing electrophoretic mobility or the like. An aliquot of the first and second materials is gated (i.e., injected for a selected period of time) into the second channel. The injection can be performed electrokinetically, i.e., by applying a voltage or current difference at the intersection between the first and second channel. The precise arrangement of the first and second channel is not critical. For example, the first and second channels optionally communicate at a crossing intersection or a T intersection. The relative amount of first and second materials in the aliquot are proportional to the flux of first and second materials in the first mixture, thereby dispensing a representative mixture of the first and second components.

Flux is ordinarily conserved in these methods. The flux of the first and second components can be the same or different during electrokinetic movement. The first or second material can be labeled, and a product resulting from combining the first or second material is optionally produced. This product is optionally labeled; in non-fluorogenic labeled, the method comprising measuring signal from the aliquot of first or second labeled material, wherein the amount of labeled material is determined by measuring the signal.

Modifying Detection Window Size to Analyze Velocitogenic Reactions

As set forth above, the size of the detection region compared to the size of a sample plug has an effect on the data which is acquired. For a gated injection of a reaction produced on the fly an "amount" detector such as a wide PMT slit (wider than the longest sample plug) results in peaks whose amplitude is proportional to the concentration (or amount) one would measure in a cuvette experiment. For concentration detectors (e.g., narrow PMT detection) the concentration is corrected by the velocity to correctly calculate the percentage of reactant converted.

As noted above, a gated injection produces a sample plug in a channel. As the sample plug travels in the channel, the molecules separate in the sample plug based upon their respective electrokinetic mobilities. As the sample plug passes a detector, all or only a portion of the plug can be detected. If the entire plug is detected, then the total amount of any detected species in the plug can be detected. If only a portion of the plug is detected, then the concentration of molecules in the detected portion can be determined, by taking velocity into account as noted herein. If the entire sample plug is detected, a velocity correction does not have to be applied to correctly determine the amount of product in the plug. Thus, by using gated injection as noted above, in conjunction with a detection window as wide or wider than a sample plug passing the detector, amounts of products, reactants and the like can be determined. Several methods can be used to vary the detection window size, including varying the slit width where the detector is a photomultiplier or other similar physical adjustments to the detector, or by data sampling frequently in time and adding all of the data for an entire sample plug.

Signal Processing, Digital Deconvolution, and Assay Component Inactivation

Complex time dependent label signals are observed for reactions in flowing microfluidic systems. Some of this complexity is due to stacking of charged molecules in the low conductivity running buffer used to separate high conductivity sample plugs and to drive electroosmotic flow. These complex signals can hinder direct interpretation of data for continuous flow enzyme inhibition or receptor binding pipettor chip experiments that rely on the use of the high/low conductivity format for electrokinetic injection.

Digital signal processing techniques provide a way of simplifying the interpretation of data in these types of experiments. Examples of data analysis routines that are implemented to simplify data interpretation include baseline subtraction and masking.

In baseline subtraction, a series of blanks are injected in a control experiment to measure the time dependent baseline, which is then subtracted from an actual experiment to obtain a difference signal that is proportional to the degree of inhibition of enzyme activity or receptor binding.

In the masking approach, a series of label (e.g., fluorescent dye) injections are made in a control experiment to characterize the timing of sample plugs as they pass a detection point. For example, the dyes can be injected (e.g., electrokinetically or by pressure injection) into a channel of a microfluidic apparatus and flowed in the channel through or past the detection point. The resulting label intensity versus time data is then normalized and subjected to a round off function to yield a mask file which has values of 1 corresponding to points in time at which sample plugs are positioned in front of the detector and values of 0 for all other times. Multiplication of the mask file with the data from an actual screening experiment then identifies the time windows of interest.

In both of these approaches, the synchronization of data acquisition and sample injection is optimally the same for control experiments and screening experiments and light source intensities, optics (or other appropriate detector) alignment and injection cycle are optimally stable over the time course of the experiments. In a preferred embodiment, the labels are fluorescent, although the same approach is used with any label described herein, in conjunction with an appropriate detector.

In addition to digital deconvolution techniques, assays are optionally performed in a format which obviates some of the difficulties observed for interpreting assays e.g., utilizing fluidic regions comprising high conductivity and low conductivity buffers (bracketing components in high or low salt buffers tends to keep components together during electroosmotic flow; see, U.S. Ser. No. 08/761,575 entitled "High Throughput Screening Assay Systems in Microscale Fluidic Devices" by Parce et al. (see also U.S. Ser. No. 08/881, 696)). In particular, assay components are optionally deactivated in regions of fluid flowing past a detector. For example, the interpretation of data for continuous flow enzyme inhibition or receptor binding studies are optionally simplified by using a running buffer having a pH sufficiently high (or low) to deactivate an assay component in the running buffer, so that signal is only generated in a sample plug (a region or fluid comprising a high concentration of sample, typically bracketed by regions of high or low salt buffer). Thus, buffers with pH in the range of about 1–5 or about 8–14 are useful for inactivating components; for ease of handling, buffers are typically in the range of about pH 3–11.

Alternatively, other inhibitors of the particular assay component are optionally added to running buffer, e.g., to inhibit enzyme activity or block receptor binding outside of the sample plug. For example, ion chelators such as EDTA or EGTA are commonly added to reactions to inhibit enzymatic reactions (e.g., where the enzyme requires a $Mg^{++}$ or $Ca^{++}$ ion). Similarly, aliquots of high or low temperature buffers, can be added to inhibit reactions comprising temperature sensitive components. Similarly, heat, cold or light can be applied to the flowing reaction, e.g., by contacting the microfluidic element comprising the microchannel in which the reaction is run with heat, cold or light. In this regard, reactants can be inactivated simply by running the reactants through a region of high electrical resistance (e.g., a narrowed portion of a microfluidic channel). Buffer traversing this region of high electrical resistance heats up (a phenomenon referred to as "joule heating"). Accordingly, by selecting current and channel width, it is possible to inactivate selected portions of flowing reaction components by joule heating. Thermocycling in microscale devices utilizing joule heating is described in co-pending application U.S. Ser. No. 60/056,058, entitled "ELECTRICAL CURRENT FOR CONTROLLING FLUID TEMPERATURES IN MICROCHANNELS" filed Sep. 2, 1997 by Calvin Chow, Anne R. Kopf-Sill and J. Wallace Parce and in Ser. No. 08/977,528, filed Nov. 25, 1997. see also, Ser. No. 08/835,101 and CIP application Ser. No. 09/054,962 by Knapp et al.

The reaction can proceed for either a selected time in the channel prior to addition of the inhibitor, or for a selected distance down the channel. The inhibitor can be added to the entire reaction mixture, or any portion thereof; where the inhibitor is in flowable form, the inhibitor can be added by time or volume gating of the flowable inhibitor.

In addition to inactivating components in selected regions of flow, inhibitors of reaction such as temperature, pH, ion chelator or the like are optionally used to deactivate or stop a reaction, e.g., where the reaction is only to be run for a set period of time.

Microfluidic Detection Apparatus

The microfluidic apparatus of the invention often, though not necessarily, comprise a substrate in which reactants are mixed and analyzed. A wide variety of suitable substrates for use in the devices of the invention are described in U.S. Ser. No. 08/761,575, entitled "High Throughput Screening Assay Systems in Microscale Fluidic Devices" by Parce et al. A microfluidic substrate holder is typically incorporated into the devices of the invention for holding and/or moving the substrate during an assay. The substrate holder typically includes a substrate viewing region for analysis of reactions carried out on the substrate. An analyte detector mounted proximal to the substrate viewing region to detect formation of products and/or passage of reactants along a portion of the substrate is provided. A computer, operably linked to the analyte detector, monitors reaction rates by taking velocities and concentrations of reactants and products into account. An electrokinetic component typically provides for movement of the fluids on the substrate. Microfluidic devices and systems are also described in filed Aug. 2, 1996, U.S. Ser. No. 08/691,632.

One of skill will immediately recognize that any, or all, of these components are optionally manufactured in separable modular units, and assembled to form an apparatus of the invention. See also, U.S. Ser. No. 08/691,632, supra. In particular, a wide variety of substrates having different channels, wells and the like are typically manufactured to fit interchangeably into the substrate holder, so that a single apparatus can accommodate, or include, many different substrates adapted to control a particular reaction. Similarly, computers, analyte detectors and substrate holders are optionally manufactured in a single unit, or in separate modules which are assembled to form an apparatus for manipulating and monitoring a substrate. In particular, a computer does not have to be physically associated with the rest of the apparatus to be "operably linked" to the apparatus. A computer is operably linked when data is delivered from other components of the apparatus to the computer. One of skill will recognize that operable linkage can easily be achieved using either electrically conductive cable coupled directly to the computer (e.g., a parallel, serial or modem cables), or using data recorders which store data to computer readable media (typically magnetic or optical storage media such as computer disks and diskettes, CDs, magnetic tapes, but also optionally including physical media such as punch cards, vinyl media or the like).

Substrates and Electrokinetic Modulators

Suitable substrate materials are generally selected based upon their compatibility with the conditions present in the particular operation to be performed by the device. Such conditions can include extremes of pH, temperature, salt concentration, and application of electrical fields. Additionally, substrate materials are also selected for their inertness to critical components of an analysis or synthesis to be carried out by the device.

Examples of useful substrate materials include, e.g., glass, quartz and silicon as well as polymeric substrates, e.g. plastics, particularly polyacrylates. In the case of conductive or semi-conductive substrates, it is occasionally desirable to include an insulating layer on the substrate. This is particularly important where the device incorporates electrical elements, e.g., electrical fluid direction systems, sensors and the like. In the case of polymeric substrates, the substrate materials may be rigid, semi-rigid, or non-rigid, opaque, semi-opaque or transparent, depending upon the use for which they are intended. For example, devices which include an optical, spectrographic, photographic or visual detection element, will generally be fabricated, at least in part, from transparent materials to allow, or at least, facilitate that detection. Alternatively, transparent windows of, e.g., glass or quartz, are optionally incorporated into the device for these types of detection elements. Additionally, the polymeric materials optionally have linear or branched backbones, and may be crosslinked or non-crosslinked. Examples of particularly preferred polymeric materials include, e.g., polydimethylsiloxanes (PDMS), polyurethane, polyvinylchloride (PVC) polystyrene, polysulfone, polycarbonate and the like.

In certain embodiments, the substrate includes microchannels for flowing reactants and products. At least one of these channels typically has a very small cross sectional dimension, e.g., in the range of from about 0.1 $\mu$m to about 500 $\mu$m. Preferably the cross-sectional dimensions of the channels is in the range of from about 0.1 to about 200 $\mu$m and more preferably in the range of from about 0.1 to about 100 $\mu$m. In particularly preferred aspects, each of the channels has at least one cross-sectional dimension in the range of from about 0.1 $\mu$m to about 100 $\mu$m. Although generally shown as straight channels for convenience of illustration, it will be appreciated that in order to maximize the use of space on a substrate, serpentine, saw tooth or other channel geometries, are used to incorporate longer channels on less substrate area. Substrates are of essentially any size, with area typical dimensions of about 1 cm$^2$ to 10 cm$^2$.

Manufacturing of these microscale elements into the surface of the substrates is generally be carried out by any number of microfabrication techniques that are well known in the art. For example, lithographic techniques are employed in fabricating, e.g., glass, quartz or silicon substrates, using methods well known in the semiconductor manufacturing industries such as photolithographic etching, plasma etching or wet chemical etching. See, Sorab K. Ghandi, *VLSI Principles: Silicon and Gallium Arsenide,* NY, Wiley (see, esp. Chapter 10). Alternatively, micromachining methods such as laser drilling, air abrasion, micromilling and the like may be employed. Similarly, for polymeric substrates, well known manufacturing techniques are used. These techniques include injection molding or stamp molding methods where large numbers of substrates may be produced using, e.g., rolling stamps to produce large sheets of microscale substrates or polymer microcasting techniques where the substrate is polymerized within a micromachined mold. Polymeric substrates are further described in Provisional Patent Application Ser. No. 60/015,498, filed Apr. 16, 1996, and U.S. Ser. No. 08/043,212, filed Apr. 14, 1997.

In addition to micromachining methods, printing methods are also used to fabricate chambers channels and other microfluidic elements on a solid substrate. Such methods are taught in detail in U.S. Ser. No. 08/987,803 by Colin Kennedy, filed Dec. 10, 1997 entitled "Fabrication of Microfluidic Circuits by Printing Techniques." In brief, printing methods such as ink-jet printing, laser printing or other printing methods are used to print the outlines of a microfluidic element on a substrate, and a cover layer is fixed over the printed outline to provide a closed microfluidic element.

The substrates will typically include an additional planar element which overlays the channeled portion of the substrate enclosing and fluidly sealing the various channels. Attaching the planar cover element may be achieved by a variety of means, including, e.g., thermal bonding, adhesives or, in the case of certain substrates, e.g., glass, or semi-rigid and non-rigid polymeric substrates, a natural adhesion between the two components. A preferred embodiment is heat lamination, which results in permanent bonding of, e.g., glass substrates. In fact, during heat lamination, the pieces fuse to form a single piece; there is no joint between the pieces, even when viewed by electron microscopy. The planar cover element can additionally be provided with access ports and/or reservoirs for introducing the various fluid elements needed for a particular screen, and for introducing electrodes for electrokinetic movement.

The introduction of large numbers of individual, discrete volumes of test compounds into the substrate is carried out by any of a number of methods. For example, micropipettors are used to introduce the test compounds to the substrate. In one embodiment, an automated pipettor is used. For example, a Zymate XP (Zymark Corporation; Hopkinton, Mass.) automated robot using Microlab 2200 (Hamilton; Reno, Nev.) pipeting station can be used to transfer parallel samples to regularly spaced wells in a manner similar to transfer of samples to microtiter plates.

In preferred aspects, an electropipettor is used. An example of such an electropipettor is described in, e.g., U.S. patent application Ser. No. 08/671,986, filed Jun. 28, 1996. Generally, this electropipettor utilizes electrokinetic or "electroosmotic" fluid direction as described herein, to alternately sample a number of test compounds, or "subject materials," and spacer compounds. The pipettor then delivers individual, physically isolated sample or test compound volumes in subject material regions, in series, into the sample channel for subsequent manipulation within the device. Individual samples are typically separated by a spacer region of low ionic strength spacer fluid. These low ionic strength spacer regions have higher voltage drop over their length than do the higher ionic strength subject material or test compound regions, thereby driving the electrokinetic pumping. On either side of the test compound or subject material region, which is typically in higher ionic strength solution, are fluid regions referred to as first spacer regions (also referred to as high salt regions on "guard bands"), that contact the interface of the subject material regions. These first spacer regions typically comprise a high ionic strength solution to prevent migration of the sample elements into the lower ionic strength fluid regions, or second spacer region, which would result in electrophoretic bias. The use of such first and second spacer regions is described in greater detail in U.S. patent application Ser. No. 08/671,986, filed Jun. 28, 1996.

Alternatively, the channels are individually fluidly connected to a plurality of separate reservoirs via separate channels. The separate reservoirs each contain a separate analyte, reagent, reaction component or the like, with additional reservoirs being provided, e.g., for appropriate spacer compounds. The test compounds and/or spacer compounds are transported from the various reservoirs into the sample channels using appropriate fluid direction schemes. In either case, it generally is desirable to separate the discrete sample volumes, or test compounds, with appropriate spacer regions.

In operation, a fluid first component of a biological system, e.g., a receptor or enzyme, is placed in a first reservoir on the substrate. This first component is flowed through a channel past a detection window and toward a waste reservoir. A second component of the biochemical system, e.g., a ligand or substrate, is concurrently flowed into the channel, whereupon the first and second components mix and are able to interact. Deposition of these elements within the device are carried out in a number of ways. For example, the enzyme and substrate, or receptor and ligand solutions introduced into the device through open or sealable access ports in the cover. Alternatively, these components are added to their respective reservoirs during manufacture of the device. In the case of such pre-added components, it is desirable to provide these components in a stabilized form to allow for prolonged shelf-life of the device. For example, the enzyme/substrate or receptor/ligand components are provided within the device in lyophilized form. Prior to use, these components are easily reconstituted by introducing a buffer solution into the reservoirs. Alternatively, the components are lyophilized with appropriate buffering salts, whereby simple water addition is all that is required for reconstitution.

Flowing and direction of fluids within the microscale fluidic devices may be carried out by a variety of methods. For example, the devices may include integrated microfluidic structures, such as micropumps and microvalves, or external elements, e.g., pumps and switching valves, for the pumping and direction of the various fluids through the device. Examples of microfluidic structures are described in, e.g., U.S. Pat. Nos. 5,271,724, 5,277,556, 5,171,132, and 5,375,979. See also, Published U.K. Patent Application No. 2 248 891 and Published European Patent Application No. 568 902.

Although microfabricated fluid pumping and valving systems may be readily employed in the devices of the invention, the cost and complexity associated with their manufacture and operation can generally prohibit their use in mass-produced disposable devices as are envisioned by the present invention. Furthermore, the velocity of components in such systems is driven by overall fluid flow, making consideration of velocity less relevant in these systems (there is no electrophoretic component of velocity in a pure pressure-driven system). For that reason, the devices of the invention will typically include an electroosmotic fluid direction system. Such fluid direction systems combine the elegance of a fluid direction system devoid of moving parts, with an ease of manufacturing, fluid control and disposability. Examples of particularly preferred electroosmotic fluid direction systems include, e.g., those described in International Patent Application No. WO 96/04547 to Ramsey et al., as well as U.S. Ser. No. 08/761,575 by Parce et al.

In brief, these fluidic control systems typically include electrodes disposed within reservoirs that are placed in fluid connection with the channels fabricated into the surface of the substrate. The materials stored in the reservoirs are transported through the channel system delivering appropriate volumes of the various materials to one or more regions on the substrate in order to carry out a desired screening assay.

Fluid transport and direction is accomplished through electroosmosis or electrokinesis. In brief, when an appropriate fluid is placed in a channel or other fluid conduit having functional groups present at the surface, those groups can ionize. For example, where the surface of the channel includes hydroxyl functional groups at the surface, protons can leave the surface of the channel and enter the fluid. Under such conditions, the surface will possess a net negative charge, whereas the fluid will possess an excess of protons or positive charge, particularly localized near the interface between the channel surface and the fluid. By applying an electric field along the length of the channel, cations will flow toward the negative electrode. Movement of the positively charged species in the fluid pulls the solvent with them.

To provide appropriate electric fields, the system generally includes a voltage controller that is capable of applying selectable voltage levels, simultaneously, to each of the reservoirs, including ground. Such a voltage controller can be implemented using multiple voltage dividers and multiple relays to obtain the selectable voltage levels. Alternatively, multiple, independent voltage sources may be used. The voltage controller is electrically connected to each of the reservoirs via an electrode positioned or fabricated within each of the plurality of reservoirs. In one embodiment, multiple electrodes are positioned to provide for switching of the electric field direction in a microchannel, thereby causing the analytes to travel a longer distance than the physical length of the microchannel.

Substrate materials are also selected to produce channels having a desired surface charge. In the case of glass substrates, the etched channels will possess a net negative charge resulting from the ionized hydroxyls naturally present at the surface. Alternatively, surface modifications may be employed to provide an appropriate surface charge, e.g., coatings, derivatization, e.g., silanation, or impregnation of the surface to provide appropriately charged groups on the surface. Examples of such treatments are described in, e.g., Provisional Patent Application Ser. No. 60/015,498, filed Apr. 16, 1996. See also, Ser. No. 08/043,212, filed Apr. 14, 1997.

Modulating voltages are then concomitantly applied to the various reservoirs to affect a desired fluid flow characteristic, e.g., continuous or discontinuous (e.g., a regularly pulsed field causing the flow to oscillate direction of travel) flow of receptor/enzyme, ligand/substrate toward the waste reservoir with the periodic introduction of test compounds. Particularly, modulation of the voltages applied at the various reservoirs can move and direct fluid flow through the interconnected channel structure of the device in a controlled manner to effect the fluid flow for the desired screening assay and apparatus.

Detectors and Labels

A "label" is any composition detectable by spectroscopic, photochemical, biochemical, immunochemical, electrical, optical or chemical means. Useful labels in the present invention include fluorescent dyes (e.g., fluorescein isothiocyanate, texas red, rhodamine, and the like), radiolabels (e.g., $^3$H, $^{125}$I, $^{35}$S, $^{14}$C, $^{32}$P, $^{33}$P, etc.), enzymes (e.g., horse-radish peroxidase, alkaline phosphatase etc.) colorimetric labels such as colloidal gold or colored glass or plastic (e.g. polystyrene, polypropylene, latex, etc.) beads. The label may be coupled directly or indirectly to the a component of the assay according to methods well known in the art. As indicated above, a wide variety of labels may be used, with the choice of label depending on sensitivity required, ease of conjugation with the compound, stability requirements, available instrumentation, and disposal provisions. Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, or cortisol, it can be used in conjunction with the labeled, naturally occurring anti-ligands. Alternatively, any haptenic or antigenic compound can be used in combination with an antibody (see, e.g., Coligan (1991) *Current Protocols in Immunology* Wiley/Greene, NY; and Harlow and Lane (1989) *Antibodies: A Laboratory Manual* Cold Spring Harbor Press, NY for a general discussion of how to make and use antibodies). The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol.

In some embodiments, a first and second label on the same or different components interact when in proximity (e.g., due to fluorescence resonance transfer), and the relative proximity of the first and second labels is determined by measuring a change in the intrinsic fluorescence of the first or second label. For example, the emission of a first label is sometimes quenched by proximity of the second label. Many appropriate interactive labels are known. For example, fluorescent labels, dyes, enzymatic labels, and antibody labels are all appropriate. Examples of interactive fluorescent label pairs include terbium chelate and TRITC (tetrarhodamine isothiocyanate), europium cryptate and Allophycocyanin, DABCYL(4-(4-dimethylamine ophenylazo) and EDANS (aminoethylamino-1naphthalene and many others known to one of skill. Similarly, two colorimetric labels can result in combinations which yield a third color, e.g., a blue emission in proximity to a yellow emission provides an observed green emission. With regard to preferred fluorescent pairs, there are a number of fluorophores which are known to quench one another. Fluorescence quenching is a bimolecular process that reduces the fluorescence quantum yield, typically without changing the fluorescence emission spectrum. Quenching can result from transient excited state interactions, (collisional quenching) or, e.g., from the formation of nonfluorescent ground state species. Self quenching is the quenching of one fluorophore by another; it tends to occur when high concentrations, labeling densities, or proximity of labels occurs. Fluorescent resonance energy transfer (FRET) is a distance dependent excited state interaction in which emission of one fluorophore is coupled to the excitation of another which is in proximity (close enough for an observable change in emissions to occur). Some excited fluorophores interact to form excimers, which are excited state dimers that exhibit altered emission spectra (e.g., phospholipid analogs with pyrene sn-2 acyl chains); see, Haugland (1996) *Handbook of Fluorescent Probes and Research Chemicals* Published by Molecular Probes, Inc., Eugene, Oreg. e.g., at chapter 13).

Detectors for detecting labeled compounds are known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers, phototubes, photodiodes or the like. Similarly, enzymatic labels are detected by providing the appropriate substrates for the enzyme and detecting the resulting reaction product. Finally simple colorimetric labels may be detected simply by observing the color associated with the label. This is done using a spectrographic device, e.g., having an appropriate grating, filter or the like allowing passage of a particular wavelength of light, and a photodiode, or other detector for converting light to an electronic signal, or for enhancing visual detection.

The substrate includes a detection window or zone at which a signal is monitored. For example, reactants or assay components are contacted in a microfluidic channel in a first region, and subsequently flowed into a second channel region comprising a detection window or region. The first and second channel region are optionally part of a single channel, but can also be separate channels, e.g., which are in fluid connection. This detection window or region typically includes a light or radiation transparent cover allowing visual or optical observation and detection of the assay results, e.g., observation of a colorometric, fluorometric or radioactive response, or a change in the velocity of colorometric, fluorometric or radioactive component. Detectors detect a labeled compound. Example detectors include spectrophotometers, photodiodes, microscopes, scintillation counters, cameras, film and the like, as well as combinations thereof. Examples of suitable detectors are widely available from a variety of commercial sources known to persons of skill.

In one aspect, monitoring of the signals at the detection window is achieved using an optical detection system. For example, fluorescence based signals are typically monitored using, e.g., in laser activated fluorescence detection systems which employ a laser light source at an appropriate wavelength for activating the fluorescent indicator within the system. Fluorescence is then detected using an appropriate detector element, e.g., a photomultiplier tube (PMT). Similarly, for screens employing colorometric signals, spectrophotometric detection systems may be employed which detect a light source at the sample and provide a measurement of absorbance or transmissivity of the sample. See also, *The Photonics Design and Applications Handbook*, books 1, 2, 3 and 4, published annually by Laurin Publishing Co., Berkshire Common, P.O. Box 1146, Pittsfield, Mass. for common sources for optical components.

In alternative aspects, the detection system comprises non-optical detectors or sensors for detecting a particular characteristic of the system disposed within detection window 116. Such sensors may include temperature (useful, e.g., when a reaction produces or absorbs heat), conductivity, potentiometric (pH, ions), amperometric (for compounds that may be oxidized or reduced, e.g., $O_2$, $H_2O_2$, $I_2$, oxidizable/reducible organic compounds, and the like).

Alternatively, schemes similar to those employed for the enzymatic system may be employed, where there is a signal that reflects the interaction of the receptor with its ligand. For example, pH indicators which indicate pH effects of receptor-ligand binding may be incorporated into the device along with the biochemical system, i.e., in the form of encapsulated cells, whereby slight pH changes resulting from binding can be detected. See Weaver, et al., *Bio/Technology* (1988) 6:1084–1089. Additionally, one can monitor activation of enzymes resulting from receptor ligand binding, e.g., activation of kinases, or detect conformational changes in such enzymes upon activation, e.g., through incorporation of a fluorophore which is activated or quenched by the conformational change to the enzyme upon activation.

One conventional system carries light from a specimen field to a cooled charge-coupled device (CCD) camera. A CCD camera includes an array of picture elements (pixels). The light from the specimen is imaged on the CCD. Particular pixels corresponding to regions of the substrate are sampled to obtain light intensity readings for each position. Multiple positions are processed in parallel and the time required for inquiring as to the intensity of light from each position is reduced. Many other suitable detection systems are known to one of skill.

Assays

In the assays of the invention, a first reactant or assay component is contacted to a second reactant or product, typically to form a product. The reactants or components can be elements of essentially any assay which is adaptable to a flowing format; thus, while often described in terms of enzyme-substrate or receptor-ligand interactions, it will be understood that the reactants or components herein can comprise a moiety derived from any of a wide variety of components, including, antibodies, antigens, ligands, receptors, enzymes, enzyme substrates, amino acids, peptides, proteins, nucleosides, nucleotides, nucleic acids, fluorophores, chromophores, biotin, avidin, organic molecules, monomers, polymers, drugs, polysaccharides, lipids, liposomes, micelles, toxins, biopolymers, therapeutically active compounds, molecules from biological sources, blood constituents, cells or the like. No attempt is made herein to describe how known assays utilizing these components are practiced. A wide variety of microfluidic assays are practiced using these components. See, e.g., U.S. Ser. No. 08/761,575 entitled "High Throughput Screening Assay Systems in Microscale Fluidic Devices" by Parce et al. (see also U.S. Ser. No. 08/881,696).

As used herein, the phrase "biochemical system" generally refers to a chemical interaction that involves molecules of the type generally found within living organisms. Such interactions include the full range of catabolic and anabolic reactions which occur in living systems including enzymatic, binding, signalling and other reactions. Further, biochemical systems, as defined herein, also include model systems which are mimetic of a particular biochemical interaction. Examples of biochemical systems of particular interest in practicing the present invention include, e.g., receptor-ligand interactions, enzyme-substrate interactions, cellular signaling pathways, transport reactions involving model barrier systems (e.g., cells or membrane fractions) for bioavailability screening, and a variety of other general systems. Cellular or organismal viability or activity may also be screened using the methods and apparatuses of the present invention, e.g., in toxicology studies. Biological materials which are assayed include, but are not limited to, cells, cellular fractions (membranes, cytosol preparations, etc.), agonists and antagonists of cell membrane receptors (e.g., cell receptor-ligand interactions such as e.g., transferrin, c-kit, viral receptor ligands (e.g., CD4-HIV), cytokine receptors, chemokine receptors, interleukin receptors, immunoglobulin receptors and antibodies, the cadherein family, the integrin family, the selectin family, and the like; see, e.g., Pigott and Power (1993) *The Adhesion Molecule FactsBook* Academic Press New York and Hulme (ed) *Receptor Ligand Interactions A Practical Approach* Rickwood and Hames (series editors) IRL Press at Oxford Press NY), toxins and venoms, viral epitopes, hormones (e.g., opiates, steroids, etc.), intracellular receptors (e.g. which mediate the effects of various small ligands, including steroids, thyroid hormone, retinoids and vitamin D; for reviews see, e.g., Evans (1988) *Science,* 240:889–895; Ham and Parker (1989) *Curr. Opin. Cell Biol,* 1:503–511; Burnstein et al. (1989), *Ann. Rev. Physiol,* 51:683–699; Truss and Beato (1993) *Endocr. Rev.,* 14:459–479), peptides, retro-inverso peptides, polymers of α-, β-, or ω- amino acids (D- or L-), enzymes, enzyme substrates, cofactors, drugs, lectins, sugars, nucleic acids (both linear and cyclic polymer configurations), oligosaccharides, proteins, phospholipids and antibodies. Synthetic polymers such as heteropolymers in which a known drug is covalently bound to any of the above, such as polyurethanes, polyesters, polycarbonates, polyureas, polyamides, polyethyleneimines, polyarylene sulfides, polysiloxanes, polyimides, and polyacetates are also assayed. Other polymers are also assayed using the systems described herein, as would be apparent to one of skill upon review of this disclosure. One of skill will be generally familiar with the biological literature. For a general introduction to biological systems, see, Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook); *Current Protocols in Molecular Biology,* F. M. Ausubel et al., eds., Current Protocols, a joint venture between Greene Publishing Associates, Inc. and John Wiley & Sons, Inc., (through 1998 Supplement) (Ausubel); Watson et al. (1987) *Molecular Biology of the Gene, Fourth Edition* The Benjamin/Cummings Publishing Co., Menlo Park, Calif.; Watson et al. (1992) Recombinant DNA Second Edition Scientific American Books, NY; Alberts et al. (1989) *Molecular Biology of the Cell Second Edition* Garland Publishing, NY; Pattison (1994) *Principles and Practice of Clinical Virology;* Darnell et al., (1990) *Molecular Cell Biology second edition,* Scientific American Books, W. H. Freeman and Company; Berkow (ed.) *The Merck Manual of Diagnosis and Therapy,* Merck & Co., Rahway, N.J.; *Harrison's Principles of Internal Medicine,* Thirteenth Edition, Isselbacher et al. (eds). (1994) Lewin *Genes,* 5th Ed., Oxford University Press (1994); The "Practical Approach" Series of Books (Rickwood and Hames (series eds.) by IRL Press at Oxford University Press, NY; The "FactsBook Series" of books from Academic Press, NY, ; Product information from manufacturers of biological reagents and experimental equipment also provide information useful in assaying biological systems. Such manufacturers include, e.g., the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

In order to provide methods and devices for screening compounds for effects on biochemical systems, the present invention generally incorporates model in vitro systems which mimic a given biochemical system in vivo for which effector compounds are desired. The range of systems against which compounds can be screened and for which effector compounds are desired, is extensive. For example, compounds are optionally screened for effects in blocking, slowing or otherwise inhibiting key events associated with biochemical systems whose effect is undesirable. As described supra, the effects of velocity of the components are corrected for to provide accurate determinations of the rates of these key events.

For example, assay compounds are optionally screened for their ability to block systems that are responsible, at least in part, for the onset of disease or for the occurrence of particular symptoms of diseases, including, e.g., hereditary diseases, cancer, bacterial or viral infections and the like. Compounds which show promising results in these screening assay methods can then be subjected to further testing to identify effective pharmacological agents for the treatment of disease or symptoms of a disease. Using the data correction methods described herein, the effects of assay compounds on biochemical systems is properly determined. For example, the binding properties of a test molecule to a target, or the effects of an enzyme modulator are easily determined using the methods herein.

Alternatively, compounds can be screened for their ability to stimulate, enhance or otherwise induce biochemical systems whose function is believed to be desirable, e.g., to remedy existing deficiencies in a patient. Furthermore, as described extensively supra, enzyme activity levels (which can be diagnostic of diseases) are correctly determined using the methods herein.

Once a model system is selected, batteries of test compounds can be applied against these model systems. By identifying those test compounds that have an effect on the particular biochemical system, in vitro, one can identify potential effectors of that system, in vivo.

In one form, the biochemical system models employed in the methods and apparatuses of the present invention will screen for an effect of a an assay compound on an interaction between two or more components of a biochemical system, e.g., receptor-ligand interaction, enzyme-substrate interaction, and the like. In this form, the biochemical system model will typically include the two normally interacting components of the system for which an effector is sought, e.g., the receptor and its ligand or the enzyme and its substrate.

Determining whether a test compound has an effect on this interaction then involves contacting the system with an assay compound and assaying for the functioning of the system, e.g., receptor-ligand binding or substrate turnover. The assayed function is then compared to a control, e.g., the same reaction in the absence of the test compound or in the presence of a known effector, taking proper steps to correct for velocity of components as described supra. Typically, such assays involve the measurement of a parameter of the biochemical system. By "parameter of the biochemical system" is meant some measurable evidence of the system's functioning, e.g., the presence or absence of a labeled group or a change in molecular weight (e.g., in binding reactions, transport screens), the presence or absence of a reaction product or substrate (in substrate turnover measurements), or an alteration in electrophoretic mobility (detected, e.g., by a change in signal from a detector in the system).

Although described in terms of two-component biochemical systems, the methods and apparatuses may also be used to screen for effectors of much more complex systems, where the result or end product of the system is known and assayable at some level, e.g., enzymatic pathways, cell signaling pathways and the like. Alternatively, the methods and apparatuses described herein are optionally used to screen for compounds that interact with a single component of a biochemical system, e.g., compounds that specifically bind to a particular biochemical compound, e.g., a receptor, ligand, enzyme, nucleic acid, structural macromolecule, etc. In all of these instances, the ability to correctly measure binding reactions, product production rates, assay component concentrations and the like, using the methods herein, makes the assay more predictive and representative.

Biochemical system models are also embodied in whole cell systems. For example, where one is seeking to screen test compounds for an effect on a cellular response, whole cells are optionally utilized. Modified cell systems are employed in the systems encompassed herein. For example, chimeric reporter systems are optionally employed as indicators of an effect of a test compound on a particular biochemical system. Chimeric reporter systems typically incorporate a heterogenous reporter system integrated into a signaling pathway which signals the binding of a receptor to its ligand. For example, a receptor is fused to a heterologous protein, e.g., an enzyme whose activity is readily assayable. Activation of the receptor by ligand binding then activates the heterologous protein, which then allows for detection. Thus, the surrogate reporter system produces an event or signal which is readily detectable, thereby providing an assay for receptor/ligand binding. Examples of such chimeric reporter systems have been previously described in the art. An example is the common chloramphenicol acetyl transferase (CAT) assay.

Additionally, where one is screening for bioavailability, e.g., transport, biological barriers are optionally included. The term "biological barriers" generally refers to cellular or membranous layers within biological systems, or synthetic models thereof. Examples of such biological barriers include the epithelial and endothelial layers, e.g. vascular endothelia and the like.

Biological responses are often triggered and/or controlled by the binding of a receptor to its ligand. For example, interaction of growth factors, e.g., EGF, FGF, PDGF, etc., with their receptors stimulates a wide variety of biological responses including, e.g., cell proliferation and differentiation, activation of mediating enzymes, stimulation of messenger turnover, alterations in ion fluxes, activation of enzymes, changes in cell shape and the alteration in genetic expression levels. Accordingly, control of the interaction of the receptor and its ligand may offer control of the biological responses caused by that interaction.

Accordingly, in one aspect, the present invention will be useful in screening for, or testing the activity of, compounds that affect an interaction between a receptor molecule and its ligands. As used herein, the term "receptor" generally refers to one member of a pair of compounds which specifically recognize and bind to each other. The other member of the pair is termed a "ligand." Thus, a receptor/ligand pair may include a typical protein receptor, usually membrane associated, and its natural ligand, e.g., another protein or small molecule. Receptor/ligand pairs can include antibody/antigen binding pairs, complementary nucleic acids, nucleic acid associating proteins and their nucleic acid ligands. A large number of specifically associating biochemical compounds are well known in the art and can be utilized in practicing the present invention.

Traditionally, methods for screening for effectors of a receptor/ligand interaction have involved incubating a receptor/ligand binding pair in the presence of a test compound. The level of binding of the receptor/ligand pair is then compared to negative and/or positive controls. Where a decrease in normal binding is seen, the test compound is determined to be an inhibitor of the receptor/ligand binding. Where an increase in that binding is seen, the test compound is determined to be an enhancer or inducer of the interaction. The methods of correcting for velocity and other effects as noted herein provide for correct determination of these parameters.

Typically, effectors of an enzyme's activity toward its substrate are screened by contacting the enzyme with a substrate in the presence and absence of the compound to be screened and under conditions optimal for detecting changes in the enzyme's activity. After a set time for reaction, the mixture is assayed for the presence of reaction products or a decrease in the amount of substrate. The amount of substrate that has been catalyzed is them compared to a control, i.e., enzyme contacted with substrate in the absence of test compound or presence of a known effector. As above, a compound that reduces the enzymes activity toward its substrate is termed an "inhibitor," whereas a compound that accentuates that activity is termed an "inducer." Again, using the data correction methods herein, a correct determination of whether a component is an inhibitor, an inducer, or irrelevant to the system can more easily be determined.

The various methods encompassed by the present invention optionally involve the serial or parallel introduction of one or a plurality of assay components into a microfluidic device. Once in the device, the assay component is screened for effect on a biological or chemical system using a serial or parallel assay format.

Assay components are optionally screened for their ability to affect a particular biochemical or chemical system. Assay components can include a wide variety of different compounds, including chemical compounds, mixtures of chemical compounds, e.g., polysaccharides, small organic or inorganic molecules, biological macromolecules, e.g., peptides, proteins, nucleic acids, or an extract made from biological materials such as bacteria, plants, fungi, or animal cells or tissues, naturally occurring or synthetic compositions. Depending upon the particular embodiment being practiced, the assay components are provided from a source of assay components, e.g., injected, free in solution, optionally attached to a carrier, a solid support, e.g., beads or the like. A number of suitable supports are employed for immobilization of the assay components. Examples of suitable solid supports include agarose, cellulose, dextran (commercially available as, i.e., sephadex, Sepharose) carboxymethyl cellulose, polystyrene, polyethylene glycol (PEG), filter paper, nitrocellulose, ion exchange resins, plastic films, glass beads, polyaminemethylvinylether maleic acid copolymer, amino acid copolymer, ethylene-maleic acid copolymer, nylon, silk, etc. Additionally, for the methods and apparatuses described herein, test compounds are screened individually, or in groups. Group screening is particularly useful where hit rates for effective test compounds are expected to be low such that one would not expect more than one positive result for a given group. Alternatively, such group screening is used where the effects of different test compounds are differentially detected in a single system, e.g., through electrophoretic separation of the effects, or differential labelling which enables separate detection.

Assay components are commercially available, or derived from any of a variety of biological sources apparent to one of skill and as described, supra. In one aspect, a tissue homogenate or blood sample from a patient is tested in the assay systems of the invention. For example, in one aspect, blood is tested for the presence or activity of a biologically relevant molecule. For example, the presence and activity level of an enzyme are detected by supplying and enzyme substrate to the biological sample and detecting the formation of a product using an assay systems of the invention. Similarly, the presence of infectious pathogens (viruses, bacteria, fungi, or the like) or cancerous tumors can be tested by monitoring binding of a labeled ligand to the pathogen or tumor cells, or a component of the pathogen or tumor such as a protein, cell membrane, cell extract or the like, or alternatively, by monitoring the presence of an antibody against the pathogen or tumor in the patient's blood. For example, the binding of an antibody from a patient's blood to a viral protein such as an HIV protein is a common test for monitoring patient exposure to the virus. Many assays for detecting pathogen infection are well known, and are adapted to the assay systems of the present invention.

Biological samples are derived from patients using well known techniques such as venipuncture or tissue biopsy. Where the biological material is derived from non-human animals, such as commercially relevant livestock, blood and tissue samples are conveniently obtained from livestock processing plants. Similarly, plant material used in the assays of the invention are conveniently derived from agricultural or horticultural sources. Alternatively, a biological sample can be from a cell or blood bank where tissue and/or blood are stored, or from an in vitro source such as a culture of cells. Techniques and methods for establishing a culture of cells for use as a source for biological materials are well known to those of skill in the art. Freshney *Culture of Animal Cells, a Manual of Basic Technique Third Edition* Wiley-Liss, New York (1994) provides a general introduction to cell culture.

In addition to biological systems, the apparatus and methods of the invention are adaptable to chemical synthetic approaches. For example chemical synthetic methods for making proteins, nucleic acids, amino acids, polymers, organic compounds and the like are well known. In general, most chemical synthetic protocols employ fluid mixing to mix reactants, reagents and the like. As applied to the present invention, a source of reactants, reagents or the like is fluidly coupled to a microfluidic channel. The reactants or reagents, which optionally comprise labels, are mixed in a microchannel. After mixing, reaction rates, product concentrations, reactant concentrations or the like are easily determined using the methods described herein. Representative mixtures can be aliquoted from one channel into a different channel for subsequent analysis, e.g., using the time-gated methods described supra. No attempt is made to describe all of the possible reactants, reactions or products which can be employed in the methods and devices of the invention; it is presumed that one of skill is generally familiar with such known methods, and that, upon review of this disclosure, could adapt these known assays to the present system.

As described above, the screening methods of the present invention are generally carried out in microfluidic devices or "microlaboratory systems," which allow for integration of the elements required for performing the assay, automation, and minimal environmental effects on the assay system, e.g., evaporation, contamination, human error, or the like. A number of devices for carrying out the assay methods of the invention are described in substantial detail herein. However, it will be recognized that the specific configuration of these devices will generally vary depending upon the type of assay and/or assay orientation desired. For example, in some embodiments, the screening methods of the invention can be carried out using a microfluidic device having two intersecting channels. For more complex assays or assay orientations, multichannel/intersection devices are optionally employed. The small scale, integratability and self-contained nature of these devices allows for virtually any assay orientation to be realized within the context of the microlaboratory system. In addition, it will be realized that the data correction methods herein are applicable to flowing systems generally, and not simply in microfluidic systems.

Computers

Typically, when using a detection device such as that described herein, data thus obtained is stored and analyzed using a computer. This may be accomplished by digitizing an image from the detection device and storing the image on a computer-readable medium. This is normally accomplished by storing the data representing the digitized image in a database, spreadsheet file, or similar storage vehicle on a computer's storage media. A computer operably linked to the analyte detector is therefore provided. The computer is coupled to the microfluidic device using cables to connect the computer to the data detection device. Alternatively, the data may be recorded on a data collection device and transported (e.g., on a computer-readable storage medium) to the computer for processing. Software on the computer determines the rate of formation of the analyte, correcting for the effects of the motion of the analyte. This is done, for example, by determining or collating the velocities of one or more components and the concentrations of one or more components and calculating the rate of formation of one or more components, while correcting for each components' velocity.

A variety of commercially available hardware and software is available for digitizing, storing, and analyzing a signal or image such as that generated by the microfluidic device described herein. Typically, a computer commonly used to transform signals from the detection device into reaction rates will be a PC-compatible computer (e.g., having a central processing unit (CPU) compatible with x86 CPUs, and running an operating system such as DOS™, OS/2 Warp™, WINDOWS/NT™, or WINDOWS 95™), a Macintosh™ (running MacOS™), or a UNIX workstation (e.g., a SUN™ workstation running a version of the Solaris™ operating system, or PowerPC™ workstation) are all commercially common, and known to one of skill in the art. Data analysis software on the computer is then employed to determine the rate of formation of the analyte in motion. Software for determining reaction rates is available, or can easily be constructed by one of skill using a standard programming language such as Visual Basic, Fortran, Basic, Java, or the like. The software is designed to determine velocities, concentrations, flux relationships and the like, as described herein.

Figure 4A:
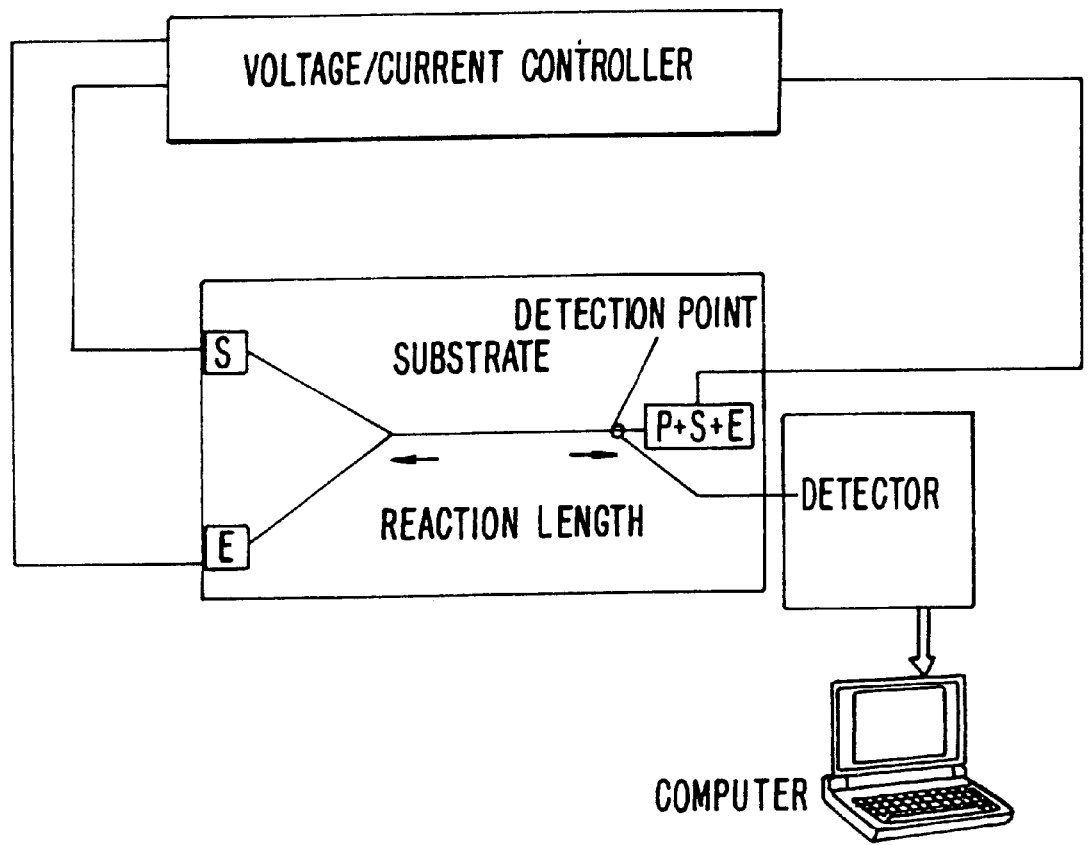
FIGS. 4A–4C provide a schematic of an integrated apparatus of the invention and flowchart operations of software for data manipulation.
Figure 4B:
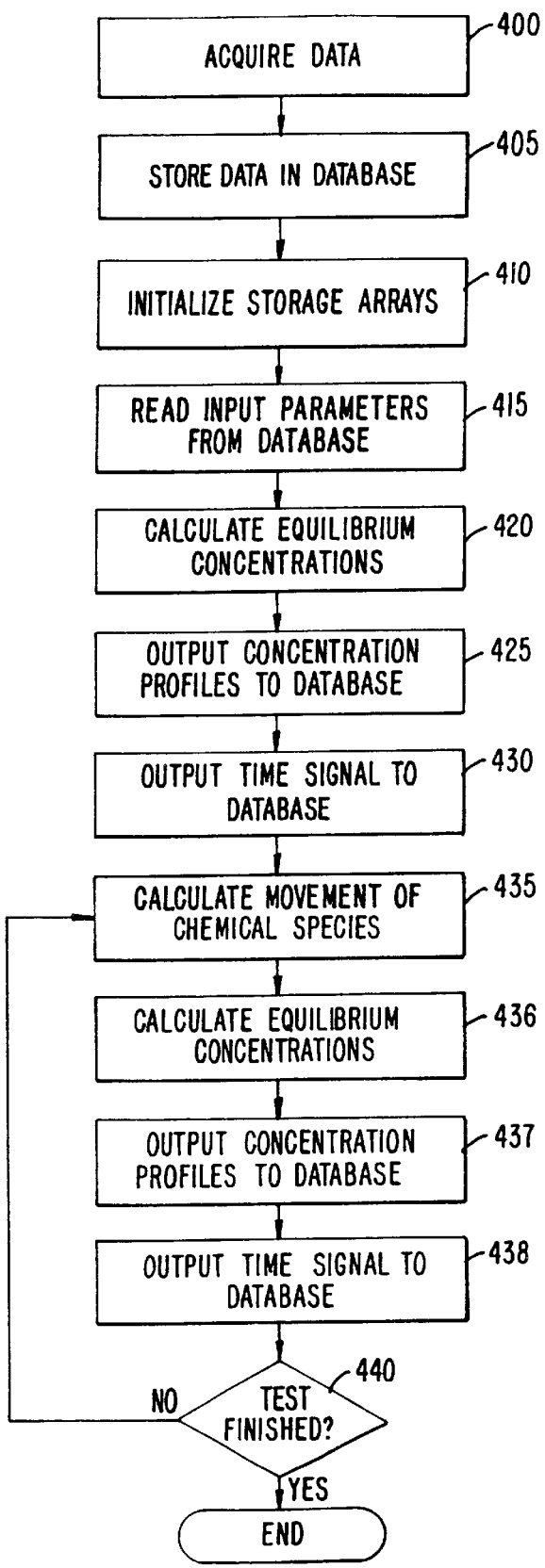

In general, software designed to perform data manipulations will include several common steps. FIG. 4B illustrates the steps performed in calculating a concentration profile along a microfluidic channel for a continuous flow binding assay as a function of time for a given association constant ($K_a$). The process illustrated by FIG. 4B begins at step 400 with the acquisition of the data from the detection device. Data thus acquired is then stored in a database, spreadsheet file, or similar construct (step 405). As noted, these steps may be carried out remotely from the computer system used to analyze the acquired data, with the acquired data being transferred to the computer system using removable media, network, or other such mechanism. The structures used to store the data (e.g., arrays) are then initialized (step 410). This includes calculating row indices and initializing the time index, and zeroing-out the concentration arrays. Test parameters are then read in from storage on the computer (step 415). This includes ranges for the variables, including the time increment between measurements. These operations need not be performed in this order, as they merely set up the variables considered in performing the calculations outlined supra. Next equilibrium concentrations are calculated (step 420). The concentration profile information generated by this step is then output to the database (step 425). The timing signal value corresponding to the concentration profile information is also output to the database (step 430).

Next, at step 435, flow conditions are used to calculate motion of the various chemical species involved in the test being analyzed. This, in effect, corresponds to the motion of the various chemical species down the microfluidic channel. The changes are reflected in the variable representing the concentrations of each of the chemical species. At step 436, new equilibrium concentrations are calculated for each of the chemical species. Again, concentration profile information and corresponding timing signal information generated by the equilibrium calculations are output to the database (steps 437 and 438, respectively). As noted, each test is broken up into time increments. Analysis of the test finishes when the number of time increments equals the duration of the test (step 440). Otherwise, the index representing the time elapsed is incremented (also represented by step 440) and steps 435–438 repeated, as illustrated in FIG. 4B.

Figure 4C:
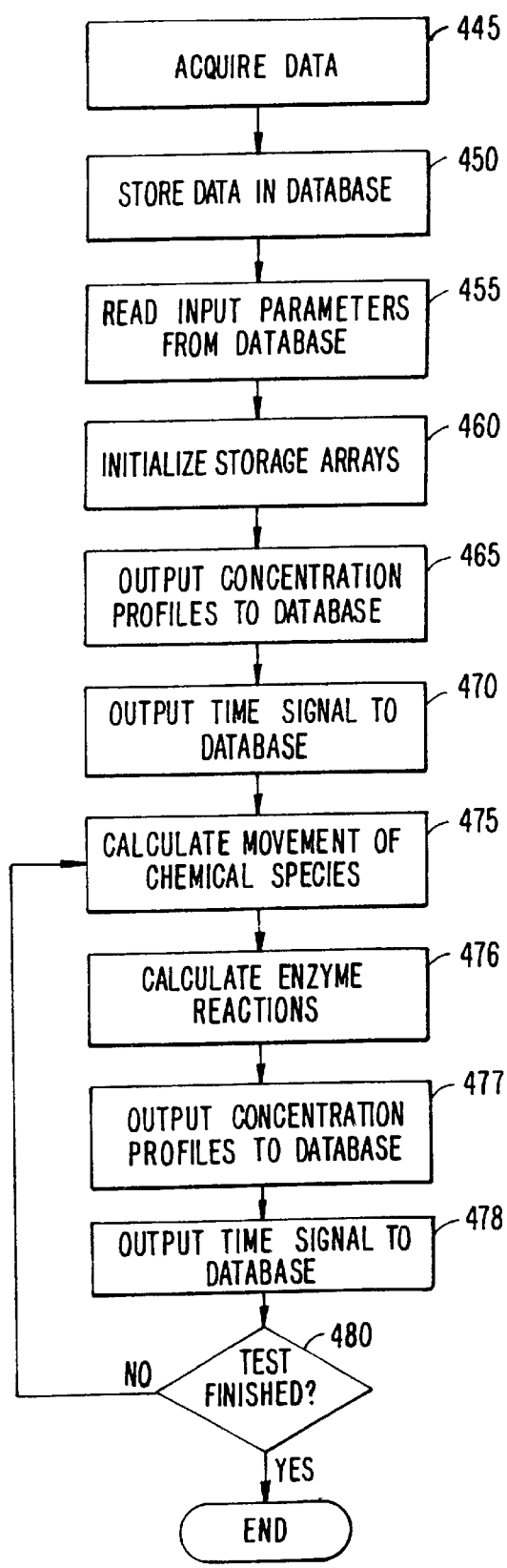

FIG. 4C illustrates an alternative set of steps according to the present invention for calculating a concentration profile along a microfluidic channel for a continuous flow binding assay as a function of time for a given association constant ($K_a$). The process illustrated by FIG. 4C begins at step 445 with the acquisition of the data from the detection device. Data thus acquired is then stored in a database, spreadsheet file, or similar construct (step 450). As noted, these steps may be carried out remotely from the computer system used to analyze the acquired data, with the acquired data being transferred to the computer system using removable media, network, or other such mechanism. Test parameters are then read in from storage on the computer (step 455), including ranges for the considered variables, including the time increment between measurements. The structures used to store the data (e.g., arrays) are then initialized (step 460), including calculating row indices and initializing the time index, and zeroing-out the concentration arrays. As before, these operations need not be performed in this order. Next, initial concentration profile information is output to the database (step 465). The timing signal value corresponding to the concentration profile information is also output to the database (step 470).

Next, at step 475, motion of the chemical species is calculated, corresponding to the motion of the various chemical species down the microfluidic channel. These changes are reflected in the variable representing the concentrations of each of the chemical species. At step 476, enzyme reactions are calculated. Again, concentration profile information and corresponding timing signal information generated by the equilibrium calculations are output to the database (steps 477 and 478, respectively). As noted, each test is broken up into time increments. Analysis of the test finishes when the number of time increments equals the duration of the test (step 480). Otherwise, the index representing the time elapsed is incremented (also represented by step 480) and steps 475–478 repeated, as illustrated in FIG. 4C.

Exemplary spreadsheet macro software is provided in Appendix A and Appendix B.

EXAMPLES

The following examples are offered to illustrate, but not to limit the present invention.

Example 1

Monitoring Flux in a Microchannel

In a given microchannel of a microfluidic device, the flux (J), with units of molecules/(cross sectional area×time), is equal to the velocity of the molecules under consideration (U) times the concentration of molecules (C); $J=U \times C$. Flux is conserved in the microchannel under consideration. In other words, the sum of the number of analyte molecules (enzymes, substrates and products, or ligands and ligand partners) times the velocity of the components is constant.

Enzyme-Substrate Assay

For example, in the following chemical system, a substrate and an enzyme are mixed at point M, and travel along a microchannel with length L to a detection point. The detector at the detection point can observe product molecules formed from the substrate, and/or substrate molecules and/or enzyme molecules as described in FIG. 4A. The enzyme (E) and substrate (S) are mixed and react to convert a small portion of the substrate into a product (P). In a preferred embodiment, the product is florescent, and easily detectable, e.g., using a photodiode, photomultiplier, a spectrometer, or the like.

In the case in which P and S have the same mobility, or in a stationary system, a concentration balance for the reacted and unreacted components is described by a simple concentration balance. $[E] \times T_{LS} \times k = [S]_{converted} = C_P$, where [E], [S] and $C_P$ are enzyme, substrate and product concentrations, respectively, in units of molecules per volume; $T_{LS}$ is the transit time of substrate between mixing and detection points or the reaction time, which is equivalent to the length for reaction divided by the velocity of substrate, $L/U_s$. The reaction constant, k, has units of molecules of product per molecules of enzyme per time.

Analyzing with the flux being conserved in a system where the product velocity and substrate velocity are not necessarily identical results in:

Flux $(J) = [E] \times T_{LS} \times k \times U_s = [S]_{converted} \times U_s = U_P \times C_P$, where $U_P$ is the product velocity. Rearranging and writing transit time of substrate as $L/U_s$ results in:

$[E] \times L/U_s \times k \times U_s = U_P \times C_P$. Then: $[E]/U_P \times L \times k = C_P$. Substituting transit time, $T_{LP}$ for product gives the nonintuitive result that product concentration is proportional to the transit time of the product, not substrate as might be extrapolated from the stationary or non-mobility changing case above: $[E] \times T_{LP} \times k = C_P$.

Joined Reactants Assay

Figure 5:
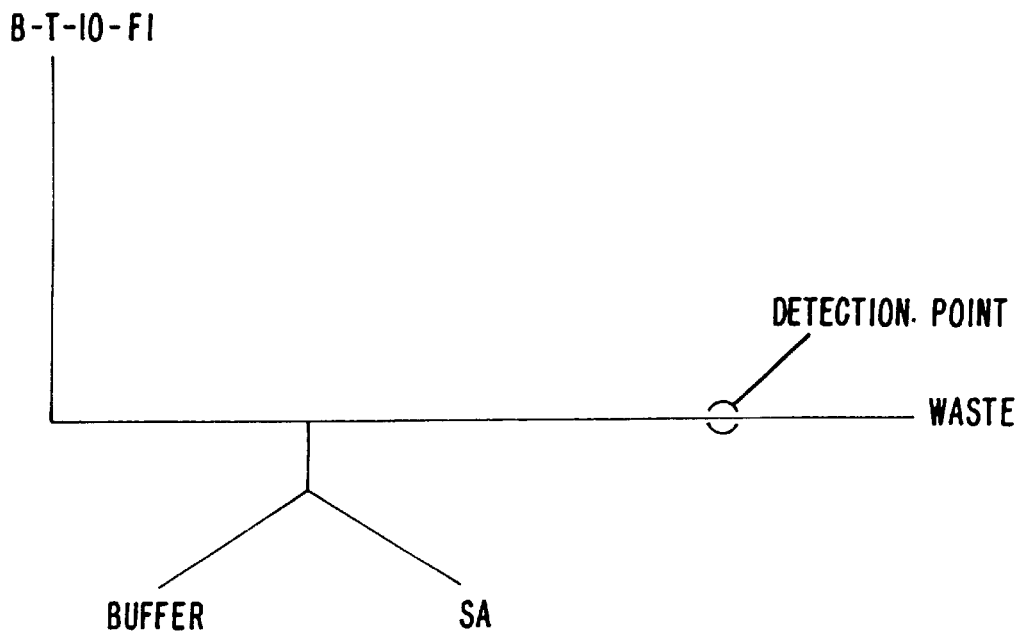
FIG. 5 is a schematic of an exemplar fluorescent assay apparatus of the invention.

In a binding assay where the binding of two molecules in a reaction system results in a product with a change in mobility, a similar analysis can be undertaken. For example when streptavidin (SA), a large molecule, binds to biotin, it changes the mobility of the labeled biotin. In one embodiment, spacer molecules (T10) are placed between the B and SA molecules to prevent quenching of B when SA is bound. Thus, both B and product molecules (B—SA) are fluorescent. The simple device depicted in FIG. 5 can be used for mixing and detection of the substrates and products, optionally further including a detector, computer, or the like.

With flux being conserved, the concentration of detected (in this case fluorescent) species changes as a result of a change in velocity. As the label does not change upon conversion of B into B—SA, the number of labeled molecules in the system remains constant. Where B molecules are converted to B—SA molecules, taking the principle of the conservation of flux into account:

$$[B] \times U_B = [B—SA] \times U_{B—SA}$$

where [B] is the concentration of B—T10-Fl and $U_B$ is the velocity of the same molecule in the system; $U_B$ is relatively slow. [B—SA] is the concentration of the complexed molecule and $U_{B—SA}$ is the velocity of the complexed molecule, which is relatively fast. Recognition of this relationship allows quantification of the amount of streptavidin present in the system by detecting downstream fluorescence. The relationship between the concentrations of B—10-Fl bound to streptavidin (B—SA) and unbound to streptavidin (B) is proportional to their mobilities:

$$[B—SA] = [B] \times U_B/U_{B—SA}.$$

At intermediate amounts of SA, where a portion of B is bound to SA the concentration is proportional to the fraction ($Y_b$) of B that is bound to SA:

$$[F] = (1-Y_b) [B] + Y_B([B]U_B/U_{B—SA}.$$

Figure 6A:
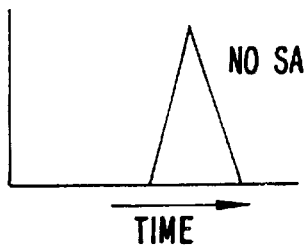
FIG. 6 is a schematic representation of a fluorescent assay of the invention.
Figure 6B:
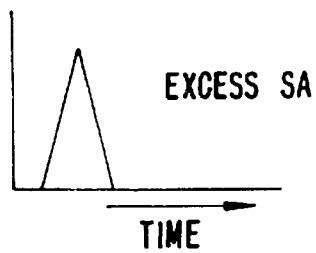
Figure 6C:
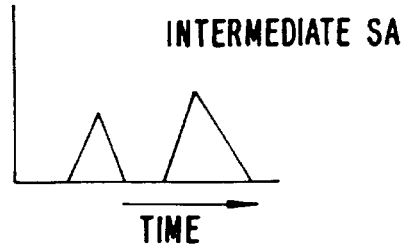

Without the knowledge that concentration changes as velocity changes, the assay is much more complicated. For example, one could sample the mixture into a separation column which separated reacted and unreacted molecules, and detected florescence. The amount of material coming off of the column per unit time is optionally detected as depicted in FIG. 6.

However, assuming conservation of flux, much simpler arrangements are possible. For instance, an electrokinetic substrate with one channel and one electrode driving fluid flow in an electrokinetic device is optionally used to monitor formation of reaction products.

Example 2

Non-fluorogenic Biotin-streptavidin Binding

The binding reaction of biotin and streptavidin was chosen as a model assay to validate the concepts of mobility shift and flux conservation as a means to detect non-fluorogenic assays in a continuous flow mode. The labeled biotin was a 5'-biotin, 3'-fluorescein derivatized short oligonucleotide, containing 10 thymidine residues (B—T10-F). The thymidine residues act as a spacer to prevent changes in the quantum efficiency of fluorescence upon the binding of streptavidin to biotin. Experimentally, it was confirmed by fluorometry (using a Perkin Elmer Luminescence Spectrometer LS50B) that the quantum yield of B—T10-F was indeed unaffected by the binding reaction to streptavidin. Unlabeled biotin (Sigma B-4501, Lot 37H1389) was also used in this study as a competitive reactant for B—T10-F in the binding reaction with streptavidin (Sigma S-4762, Lot 44H6890).

The buffers used for the reagents contain 100 mM Hepes at pH 7.0 and 1M NDSB-195 (a non-detergent sulfobetaine, Calbiochem-Novabiochem), filtered with 0.2 $\mu$m filters. To vary the electroosmotic mobility of the buffer solution, a buffer was prepared without added salt and one with 50 mM NaCl. A neutral dye, Rhodamine B, was used to measure the electroosmotic mobility of the buffers.

Figure 7:
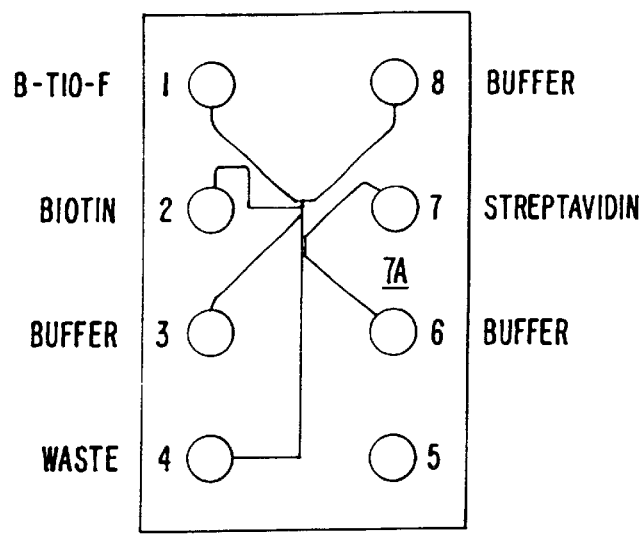
FIG. 7 is a schematic of the channel and reagent well layout of Caliper LabChip™ designated "7A."

All on-chip experiments for this example were performed on a Caliper technologies "7A" chip design; its channel and reagent well layout is illustrated in FIG. 7. In this design, each reagent well (1, 2, and 7) is paired with a buffer well (8, 3, and 6) for on-chip dilution of reagent concentration. The microfluidic channels, 70 $\mu$m wide and 10 $\mu$m deep, were etched in a soda lime glass substrate and then sealed via thermal bonding with a top glass plate containing eight 3-mm diameter holes serving as reagent wells. The electrical currents and voltages of the 8 electrodes in contact with the wells were controlled by a Caliper 3180 LabChip™ controller and Caliper's unified 1 software.

The fluorescence signals were measured in the epifluorescence mode using a Nikon microscope (Nikon Eclipse TE300) equipped with a photomultiplier tube (PTI D104 Microscope Photometer) and a 50 W tungsten/halogen light source. A dichroic filter, High Q FITC Filter Set (#41001, Chroma Technology Corp.), was used for selecting the excitation and emission wavelengths for B—T$_{10}$-F. A High Q TRITC Filter Set (#41002, Chroma Technology Corp.) was used for Rhodamine B.

The electroosmotic mobility of the buffers was measured on the 7A chip using Rhodamine B as a neutral dye marker. The electrophoretic mobility of B—T$_{10}$-F and B—T$_{10}$-F bound to streptavidin (SA—B—T$_{10}$—F) was measured directly on the 7A chip using Hepes buffer without NaCl. For the Rep measurements, the concentrations of B—T$_{10}$-F and SA—B—T$_{10}$-F were 3.1 $\mu$m and 0.88 $\mu$m, respectively. The measured electrokinetic mobilities are tabulated in Table 1. As can be seen from these measurements, B—T$_{10}$-F has an electrophoretic mobility in the opposite direction relative to the electroosmotic flow of the buffers due to its negative charge at pH 7.0. After the binding reaction, $\mu_{ep}$ of the product decreases in magnitude due to a decrease in the charge-to-mass ratio. Thus, the resulting electrokinetic mobility of B—T$_{10}$-F is lower than that of SA—B—T$_{10}$-F, as in the case described in FIG. 1.

TABLE 1

Electrokinetic Parameters of Buffers and Reagents

| Buffer/Reagent | $\mu_{eo}$ (cm$^2$/v.s) | $\mu_{ep}$ (cm$^2$/v.s) |
| --- | --- | --- |
| 100 mM Hepes + 1M NDSB | 5.5 × 10$^{-4}$ | — |
| 100 mM Hepes + 1M NDSB + 50 mMNACL | 3.7 × 10$^{-4}$ | — |
| B-T$_{10}$-F | — | −2.0 × 10$^{-4}$ |
| SA-B-T$_{10}$-F | — | −0.7 × 10$^{-4}$ |

A series of experiments was first performed to determine the concentration of reagents for the binding and competitive binding assays such that the signal-to-noise ratio was high and the fluorescence was still linear as a function of concentration. The optical setup was also varied to ensure that the light intensity and the iris size chosen did not cause a significant photobleaching of the fluorescent dye. Furthermore, based on model calculations, the buffer with salt gives better separation conditions for distinguishing the bound and free B—T$_{10}$-F within the geometric and electrical parameters used in our experiments on the chip. Therefore, the results reported below were performed with the Hepes buffer containing 50 mM NaCl.

Figure 8:
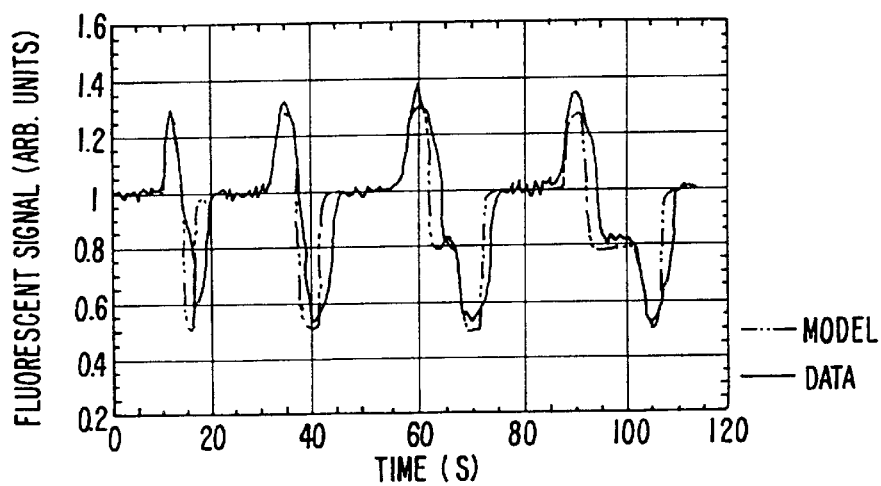
FIG. 8 is a mobility shift signal measured (solid curve) for the binding reaction of B—$T_{10}$—FL and streptavidin under a continuous flow mode for injection times of 2.5 s, 5 s, 10 s, 15 s. The concentrations for B—$T_{10}$—F and streptavidin were 3.1 $\mu$m and 78 nM, respectively. The dashed curve depicts model predictions.

FIG. 8 illustrates the measured fluorescence signal (solid curve) of the non-fluorogenic binding assay of B—$T_{10}$-F with streptavidin in the continuous flow mode. The concentrations of B—$T_{10}$—F and streptavidin were 3.1 μm and 78 nM. Since a streptavidin molecule has 4 biotin binding sites, the stoichiometry of B—$T_{10}$-F to streptavidin is 10:1. In this experiment, the injection time of streptavidin was varied from 2.5 s, 5 s, 10 s, and 15 s. The characteristic signature of a peak followed by a valley can be seen in all cases. For injection times of 10 and 15 s, the plateau region is also clearly exhibited. In this plot, the time domain model calculations using the measured electrokinetic mobilities as input parameters are depicted by the dashed curve. It should be noted that the actual injection pulse shapes were used in the model instead of an assumed square pulse shape. For quantitative comparison, both the measured fluorescence and model prediction were first normalized by the background fluorescence level when the channel contained only B—$T_{10}$-F. Furthermore, the magnitude of the model calculations were adjusted by one multiplicative factor to give the best fit to the measured signals in arbitrary fluorescence units. Thus, the model has one adjustable parameter in the y-axis and no adjustable parameter in the time axis. As can be seen in this comparison, the agreement between the model and experimental data is quite good.

Figure 9:
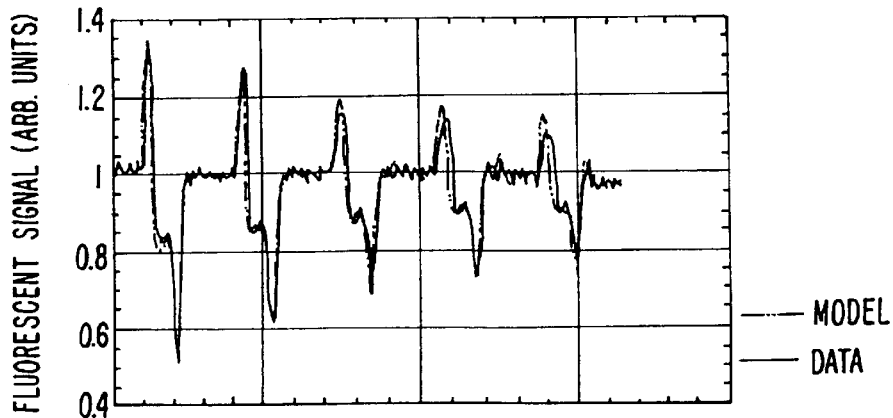
FIG. 9 is a mobility shift signal measured (solid curve) for the competitive binding reaction of B—$T_{10}$—Fl and biotin with streptavidin for a 12-s injection time in a continuous flow mode. The concentrations for B—$T_{10}$—F and streptavidin were 3.1 $\mu$M and 78 nM, respectively. The concentrations of biotin were 0, 0.78, 1.6, 2.3, and 3.1 $\mu$M. The dashed curve depicts model predictions.

In another experiment, the competitive binding reaction between B—$T_{10}$-F and unlabeled biotin with streptavidin was studied. FIG. 9 shows the measured fluorescence signal (solid curve) of the non-fluorogenic competitive binding assay results in the continuous flow mode. The streptavidin injection time was 12 s. The concentrations of B—$T_{10}$-F and streptavidin were 3.1 μm and 78 nM. The concentration of biotin was varied at 5 levels: 0, 0.78, 1.6, 2.3, and 3.1 μM. The dashed curve, denoting model calculations based on the actual injection pulse profiles, was again fitted to the data using one adjustable parameter in the y-axis as in FIG. 8. As expected, the magnitudes of the peaks and valleys decrease proportionately as biotin is titrated into the binding assay to compete with B—$T_{10}$-F. Once again, the agreement between model calculations and measured data is good.

Figure 10:
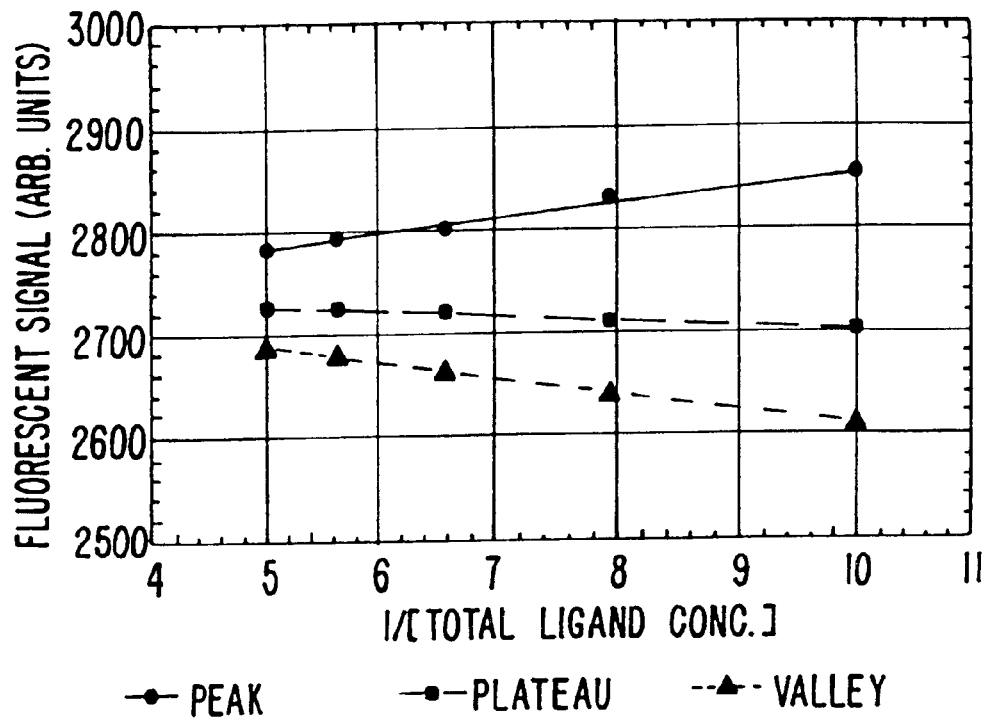
FIG. 10 is a plot of the fluorescence level versus the reciprocal of the total concentration of biotin-containing species.

The data in FIG. 9 is further analyzed by plotting the magnitude of the peak, plateau, and valley fluorescence level versus the reciprocal of the sum of the labeled and unlabeled biotin concentration. A linear relationship is expected for each set of data for a competitive binding assay, which was exhibited experimentally as shown in FIG. 10. Any one of these features can be used as a calibration curve to determine the free biotin concentration in an assay.

In summary, on-chip data of binding assays of biotin and streptavidin validated the use of mobility shift to detect non-fluorogenic assays in a continuous flow mode. The need for product concentration correction using conservation of flux to analyze assays performed in microchannels of a flowing system is also definitively demonstrated by a quantitative comparison of data to model calculations.

Example 3

Applications to Additional Non-Fluorogenic Assays

Figure 11:
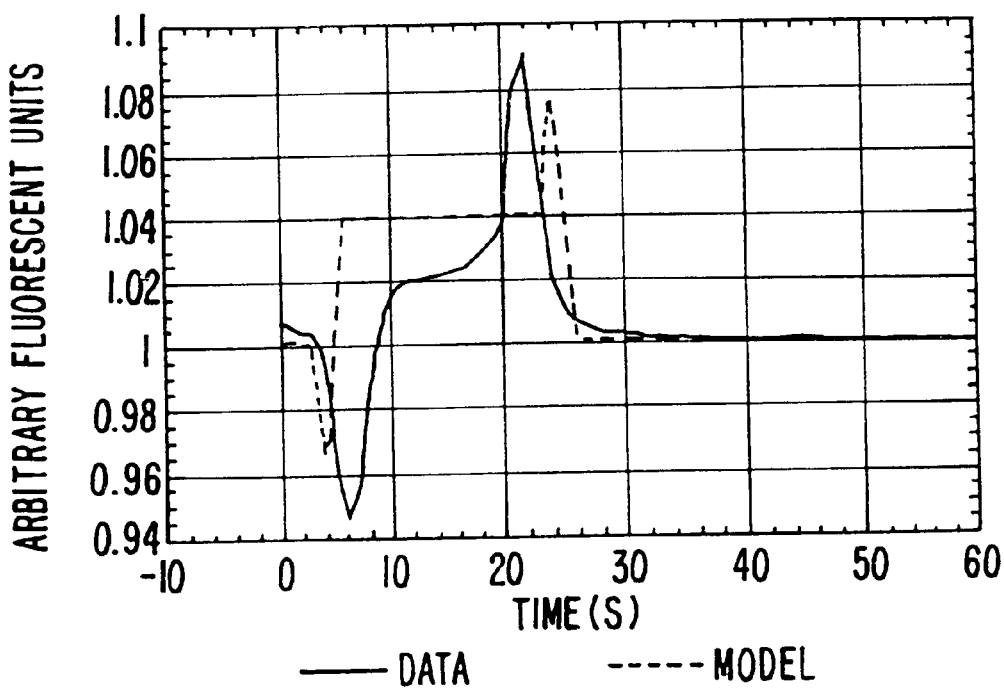
FIG. 11 shows experimental data and model calculations of a non-fluorogenic PKA enzyme assay in a continuous flow mode.

The continuous flow, non-fluorogenic assay format can be applied directly to binding assays such as of antigen-antibody and receptor ligand binding. It is also readily applicable to other biochemical assays such kinase enzyme assays and hybridization of PNA and a complimentary peptide nucleic acid (PNA). FIG. 11 shows a plot of some data on a protein kinase A (PKA) enzyme assay (Promega, V5340) in a continuous flow mode using a Caliper 7A chip. In this assay, the phosphorylation of the substrate alters the peptide's net charge from +1 to −1. Qualitatively, the data (solid curve) shows the expected valley appearing before the peak, with a plateau region in between. A model calculation using estimated electrokinetic mobilities, enzyme kinetic parameters from the literature, and estimated applied voltage values in an Excel spatial domain model (dashed curve) predicted the qualitative features of the fluorescent signal. The Macro program listing of the spatial domain model for non-fluorogenic assay is included as Appendix B.

In the binding assay of biotin and streptavidin presented above, the labeled biotin is a small molecule (244 dalton) whereas the unlabeled streptavidin is large (65,000 dalton). As such, the reaction produced a labeled product with a significantly different electrokinetic mobility compared to the labeled reactant, and this large difference makes the detection of the binding reaction quite straight forward. In the opposite case when the labeled reactant is large (such as a protein receptor) and the unlabeled reactant is small (such as a ligand), the induced mobility shift due to binding could be very small due to a small change in the mass. In this case, it is more difficult to detect the onset of reaction using the continuous flow, non-fluorogenic assay format as described here. However, methods to enhance the detection of non-fluorogenic assays on chips for small mobility shifts are available as described above. One approach is to inject the reaction mixture into a planar cyclic capillary electrophoresis channel to separate products from reactants. In this case, the separation time can be made very long by continuously cycling the voltage around the cyclic structure. Another method is to use the concept of interference of concentration waves in channels to enhance to the magnitude of peaks and valleys in the non-fluorogenic assay fluorescence signal.

Example 4

High Throughput Systems

The present invention relates to the performance of assays, and particularly, high-throughput assays, within microfluidic devices. The performance of high-throughput assays within microfluidic devices has been described in great detail in commonly owned published International Application No. WO 98/00231, as well as supra. Apparatus and methods for introducing large numbers of different compounds into the microfluidic devices are described in commonly owned published International Application No. WO 98/00705, which is also incorporated herein by reference in its entirety for all purposes.

In many cases, the biochemical system that is being assayed can be selected or engineered to have an easily detectable result. For example, assaying enzyme function is typically made simple by utilizing fluorogenic substrates for the enzyme, e.g., non-fluorescent substrates which yield fluorescent products. Such assays are readily incorporated into microfluidic devices for performance of assays to identify compounds that may effect normal enzyme activity. In one embodiment, using a 7A chip as described supra (see, e.g., FIG. 7), one continuously flows enzyme and fluorogenic substrate through a channel of the device. This continuous flow of enzyme and substrate produces a steady state fluorescent signal from the fluorescent product. Enzyme inhibitor (or, e.g., compounds for which one wishes to test inhibitory activity) are periodically introduced into the main channel. These inhibitors then reduce the amount of product produced within the main channel resulting in a deviation from the steady state signal. See also, Examples of specific assays and their results are shown in the figures attached herewith. Specifically, both phosphatase assays and protease assays were performed using a 7A chip.

Figure 12:
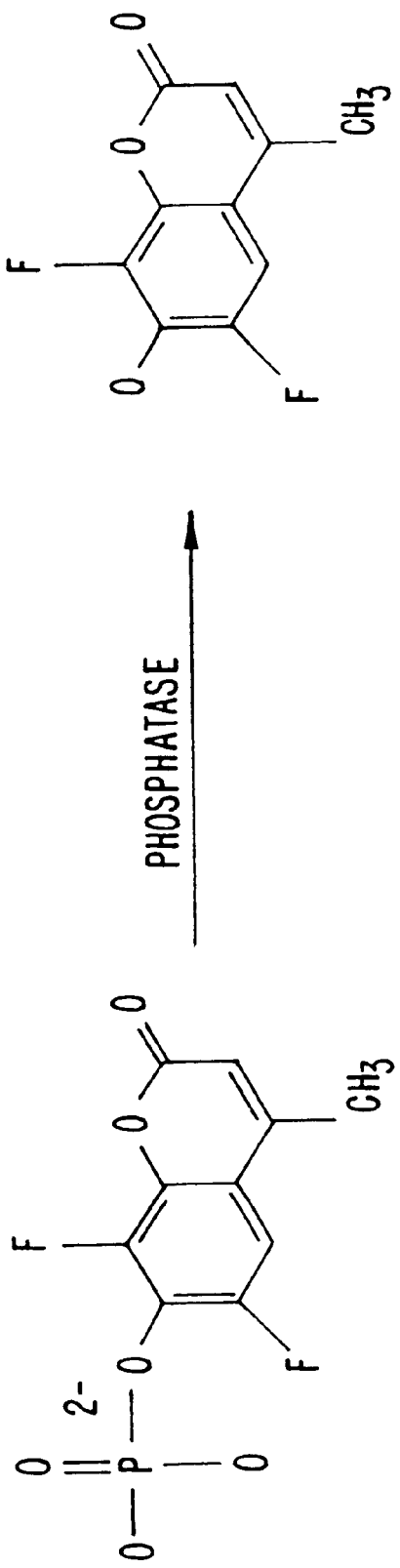
FIG. 12 shows an example of the progression of a phosphatase reaction on the exemplar fluorogenic substrate dFMUP.
Figure 13:
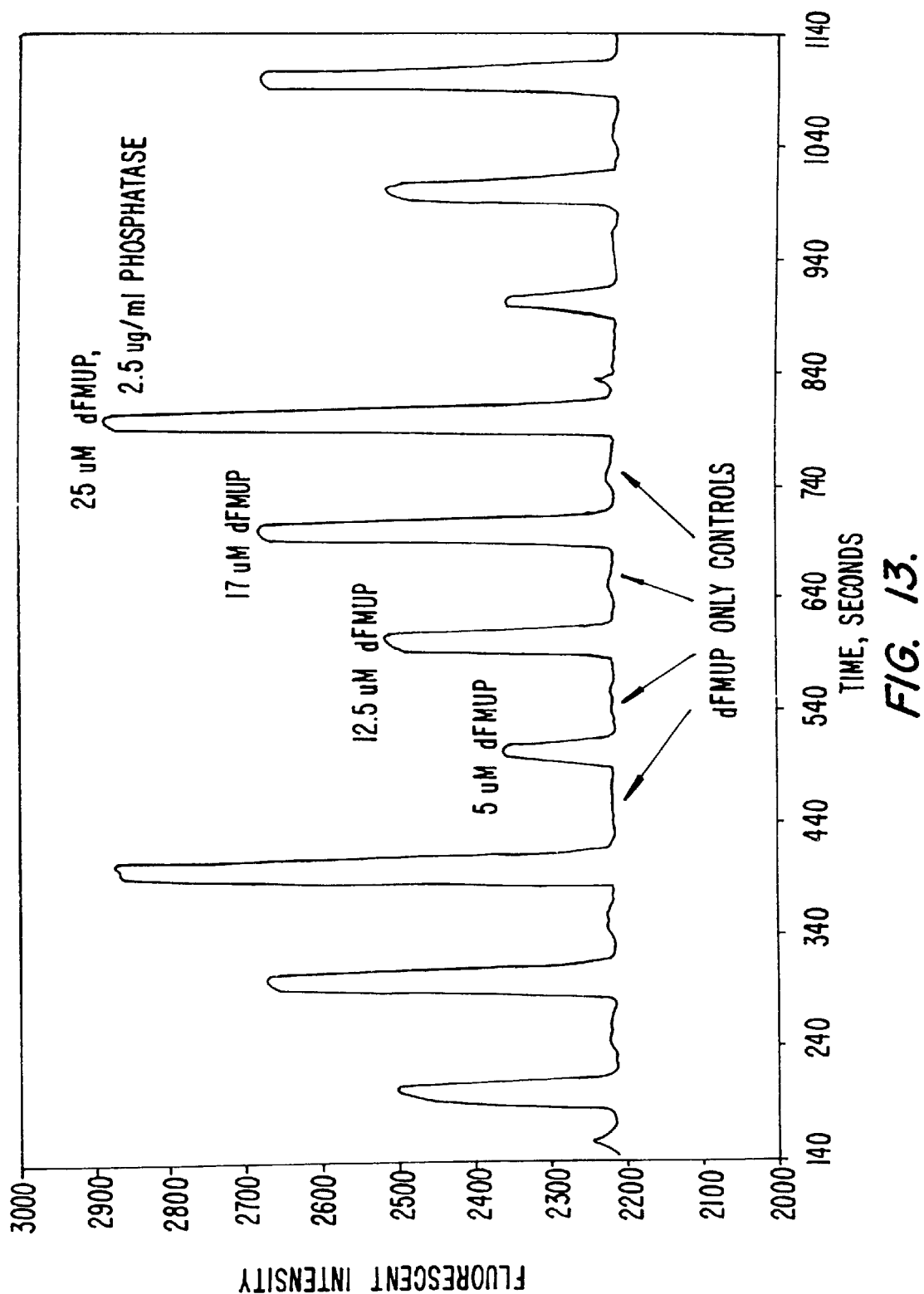
FIG. 13 is a fluorescence trace of the titration of substrate in a microchip phosphatase assay.

The phosphatase assay utilizes a fluorogenic substrate dFMU, which produces a fluorescent signal upon dephosphorylation. The reaction is shown schematically in FIG. 12. FIG. 13 shows typical data obtained from the on-chip phosphatase assay. In this experiment, the running buffer was 1 M NDSB-195 in 25 mM HEPES, pH 7.9. Reagent concentrations were 125 nM LAR, 50 $\mu$M dFMUP and 200 $\mu$M peptide inhibitor in wells 6, 8 and 2 respectively. Each reagent well was paired with a well containing running buffer. The system was programmed to repeatedly run a sixteen-step loop of experiments. The sixteen steps were a series of controls followed by the enzyme plus substrate experiment. Each step of the loop conserved the total current flux in the main reaction channel. The total flux remained constant during each step of the loop by maintaining a constant sum of currents from the wells. The proportion of that overall flux from each reagent and buffer well was selected to provide the desired final reagent concentration in the main reaction channel. The fluorescence response was monitored in each of the sixteen experimental steps where the continuous flow stream alternated between buffer, substrate, buffer, substrate plus enzyme at four different substrate concentrations. An example of a controller program is shown below, Table 2.

TABLE 2

Controller Software Program

| Channel State: | 1 $\mu$A | 2 $\mu$A | 3 $\mu$A | 4 V | 5 $\mu$A | 6 $\mu$A | 7 $\mu$A | 8 $\mu$A | time sec | |
|---|---|---|---|---|---|---|---|---|---|---|
| 1 | 5 | 0 | 5 | 1000 | 0 | 0 | 5 | 0 | 15 | Buffer |
| 2 | 0 | 0 | 5 | 1000 | 0 | 0 | 5 | 5 | 15 | Substrate |
| 3 | 5 | 0 | 5 | 1000 | 0 | 0 | 5 | 0 | 15 | Buffer |
| 4 | 0 | 0 | 5 | 1000 | 0 | 5 | 0 | 5 | 15 | Substrate + Enzyme |

The substrate concentration was varied for each sequence of three controls followed by the enzyme reaction. The concentrations of the reagents in the main channel can be calculated from the ratio of currents used to pump the reagents. The concentrations in the reaction channel are simply the concentration in the well multiplied by the ratio of current applied at that well, divided by the total current. Here the reaction mixture was 62.5 $\mu$M LAR, and either 5, 12.5, 17 or 25 $\mu$M dFMUP. The raw fluorescence data is plotted as a function of time. The purpose of this experiment was to demonstrate the increase in enzymatic signal as a function of increasing substrate concentration in a controlled system. Rise times for the enzyme/substrate signal are less than 5 seconds. The background signal remained low over the course of many experimental cycles.

Figure 14:
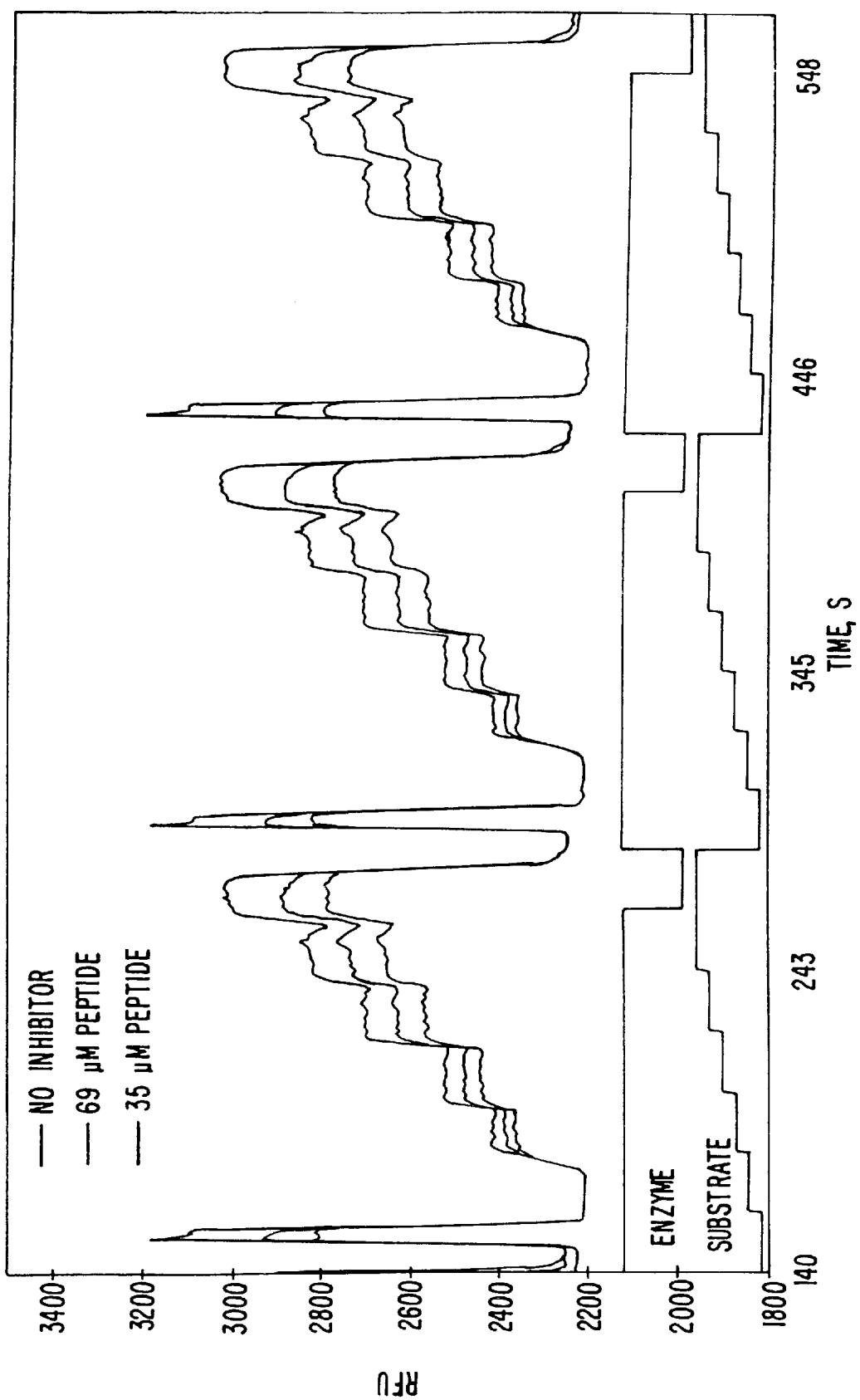
FIG. 14 is a fluorescence trace of the titration of substrate in a microchip phosphatase assay as a function of inhibitor concentration.

The raw data for the $K_m$, $V_{max}$, $k_{cat}$ and $K_i$ determinations are plotted in FIG. 14. Each trace represents a set of experiments performed in seven step cycles. The enzyme solution was pumped continuously, providing a final concentration of 83 nM LAR in 1 M NDSB-195, 50 mM HEPES, pH 7.5 in the reaction channel, while the signal at various substrate concentrations was recorded. The first step of the cycle is an enzyme only control. Steps two through six contain different levels of substrate up to an including 17 $\mu$M dFMUP. The final step of the cycle is a substrate only control, 17 $\mu$M dFMUP with no enzyme. The entire experiment, (no peptide inhibitor), was repeated at two inhibitor concentrations, 35 uM and 69 uM peptide.

The blank subtracted signals were averaged for triplicate measurements and transformed into the reciprocal form of the Lineweaver-Burke equation: $1/v = K_m/V_{max} \times 1/[S] + 1/V_{max}$, where v is the reaction rate in RFU/s, $K_m$ is the Michaelis Menton constant for LAR and dFMUP, $V_{max}$ is the rate of maximum enzyme turnover, and S is the dFMUP concentration. The double reciprocal plot for the range of substrate concentrations, 0–20 $\mu$M dFMUP, in the absence of inhibitor, gives $K_m$ and $V_{max}$. The rates were evaluated as a change in fluorescent product signal over a fixed time. The change in fluorescence is the difference in signal for a given substrate and enzyme concentration minus the substrate only control. The fixed time is the time it takes for the product, dFMU, to travel from the point of mixing of substrate and enzyme to the detector. The time for the product to flow was measured directly. dFMU was placed in well 6, the well in which enzyme typically resides; the time for the product to flow to the detector poised 8 mm from the source of dFMU in the reaction channel was monitored. The slope of a calibration curve of the signal generated as a function of dFMU concentration was used to convert the fluorescent signals to dFMU concentrations such that the rates could be expressed as a change in product concentration per unit time.

Figure 15:
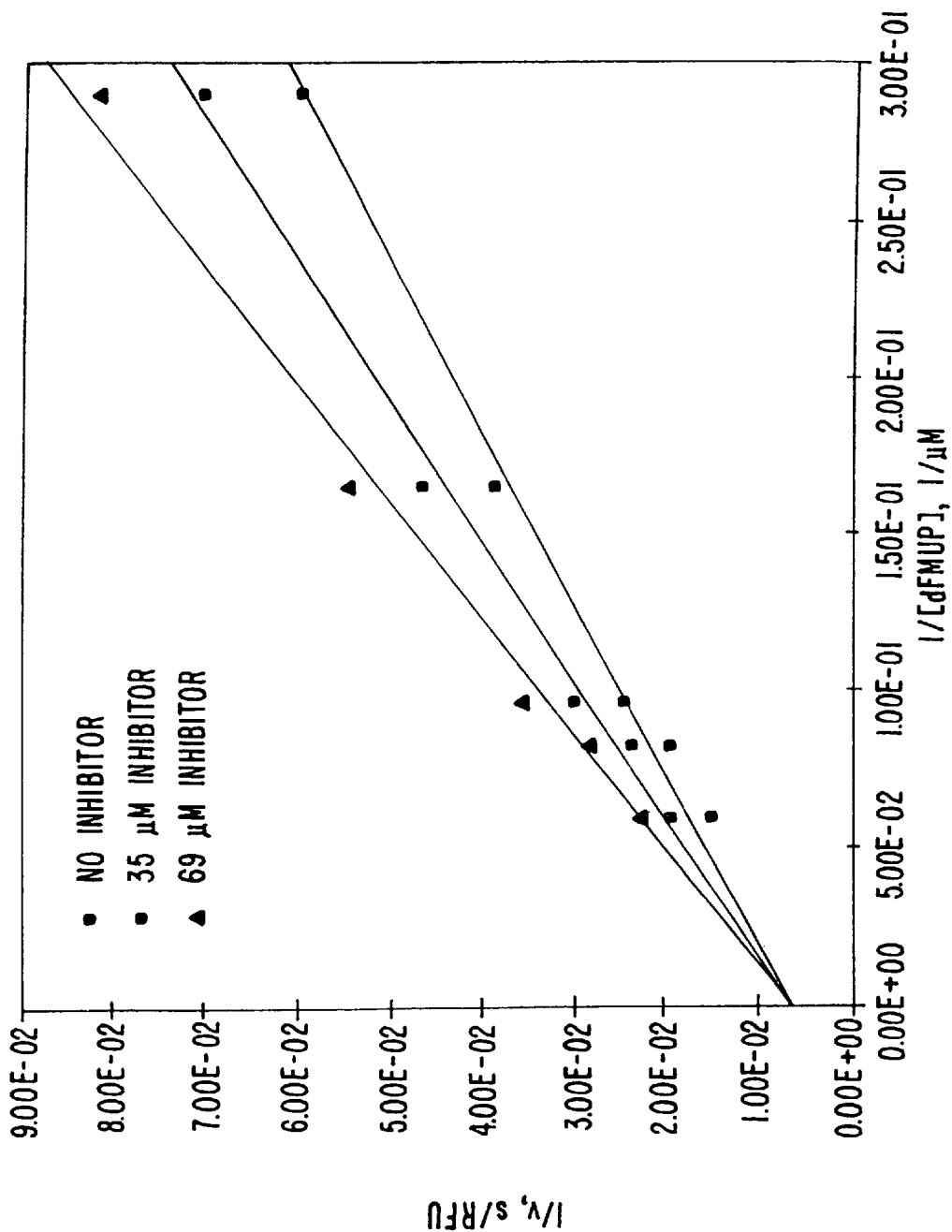
FIG. 15 is a Lineweaver Burke plot used to determine Km and Ki for the phosphatase assay.

A least squares fit of the three straight lines: no inhibitor, 35 $\mu$M and 69 $\mu$M peptide, was performed with the constraint that they meet at a common intercept on the y axis, $1/V_{max}$ FIG. 15. This fit produced a $V_{max}$ of 6.71 $\mu$M dFMU/s. $k_{cat}$ could then be calculated from the ratio of $V_{max}$ to the enzyme concentration. The $k_{cat}$ is 4.74 $\mu$mol/min nmol LAR. The parallel analysis performed on the spectrophotometer in the same running buffer yielded a $k_{cat}$ of 6 $\mu$mol/min nmol LAR. The $K_i$ for 35 and 69 $\mu$M peptide were 155 and 147 $\mu$M, respectively. The same analysis performed in a cuvette experiment with 1 mg/ml BSA in the running buffer gave 167 $\mu$M peptide. The data are summarized in Table 3.

TABLE 3

Summary of LAR/dFMUP Kinetic Constants

| | Km | Ki | kcat | Conditions |
|---|---|---|---|---|
| | LAR/dFMUP $\mu$M | Peptide $\mu$M | $\mu$mol/min nmolLAR | |
| Cuvette | 23.2 | 167 | 6 | 1M NDSB-195/50 mM Hepes, pH 7.5, 0.1 mg/ml BSA |
| Chip | 18.7 | 151 | 4.74 | 1M NDSB-195/50 mM Hepes, pH 7.5 |

In addition to the above kinetic studies, rate as a function of substrate concentration data was collected on three separate chips in order to consider interchip reproducibility for $K_m$ analyses. The combined data were used to prepare a double reciprocal plot. The ratio of the slope to the intercept of the best fit line for these points, ($R^2 = 0.999$), produced a $K_m$ of 18.2 $\mu$M. The average of the three on-chip $K_m$ values is 18.7 $\mu$M +/−4.44 (23.8%), n=3. This is in excellent agreement with cuvette experiments performed on the spectrophotometer where dFMU was detected at 360 nm in a temperature controlled cuvette at 25_C. The cuvette experiments gave an average $K_m$ of 23.25 $\mu$M +/−5.25 (22.6%), for four separate $K_m$ determinations.

Figure 16:
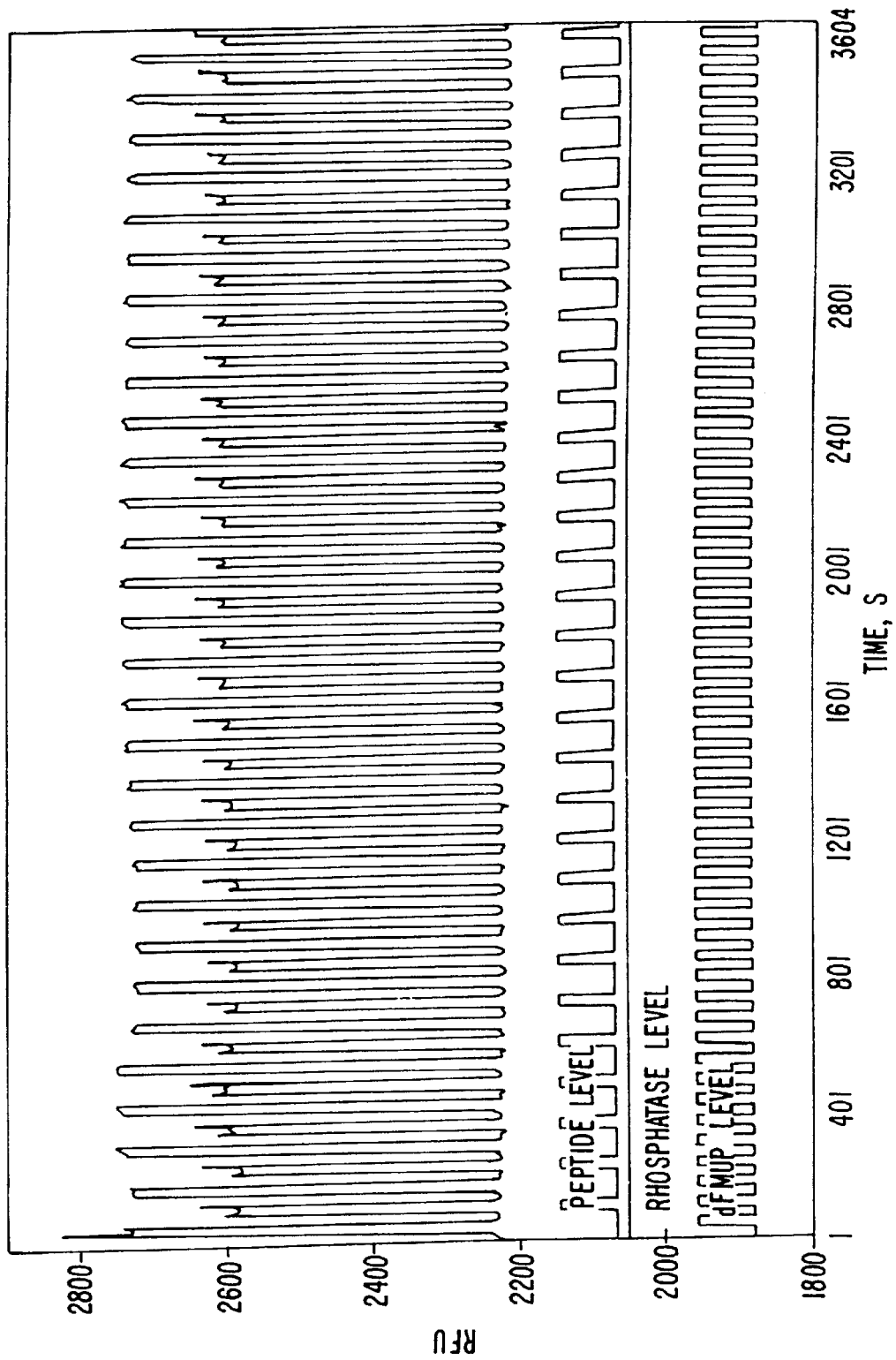
FIG. 16 is the third hour of an eight-hour experiment for a continuous flow phosphatase assay on a microchip with enzyme inhibition.
Figure 17:
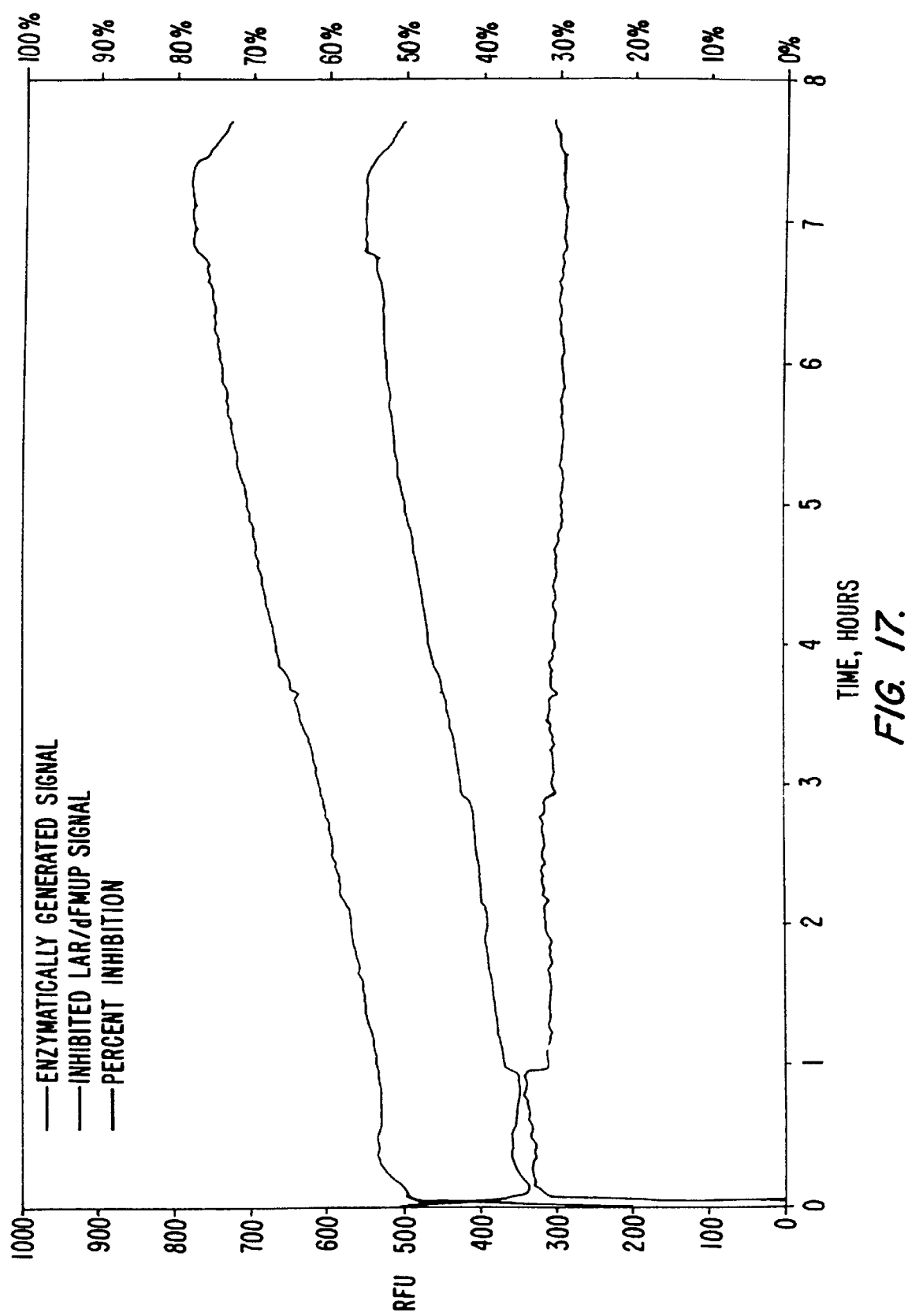
FIG. 17 is the summary of the eight-hour phosphatase inhibition experiment showing continuous inhibition for the duration of the study.

A continuous flow experiment was performed to assess the chip lifetime for the enzyme inhibitor assay. In this experiment 42 nM LAR was continuously pumped through the reaction channel. Alternately, 6.25 nM dFMUP or 6.25 nM dFMUP and 41.6 µM peptide inhibitor were pumped into the flow stream. The reagents were loaded into reagent wells on the chip, the controller was initiated and the script was allowed to run for eight hours. The raw data for the third hour of the experiment is shown in FIG. 16. The entire experiment is summarized by FIG. 17. Note that although both the uninhibited and the inhibited signals drift with time, the percent inhibition remained constant for the entire experiment. The average percent inhibition is 32.45+/−1.73 (5.3%). From the flow rate and the cross sectional area of the capillary it is estimated that approximately 18 µl total reagent volume was consumed during the eight hours.

Figure 18:
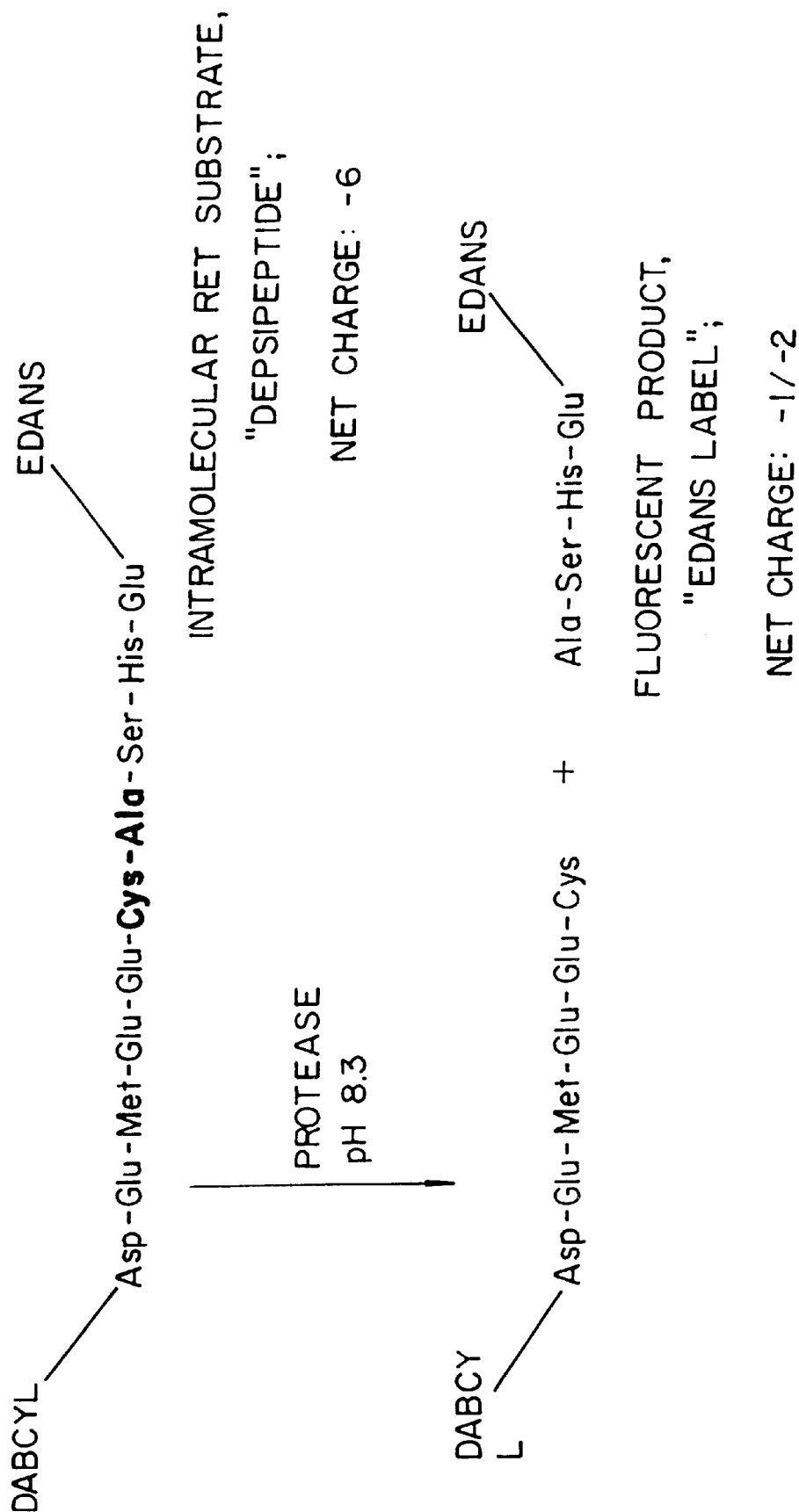
FIG. 18 is a schematic of the exemplar protease reaction on a microchip.
Figure 19:
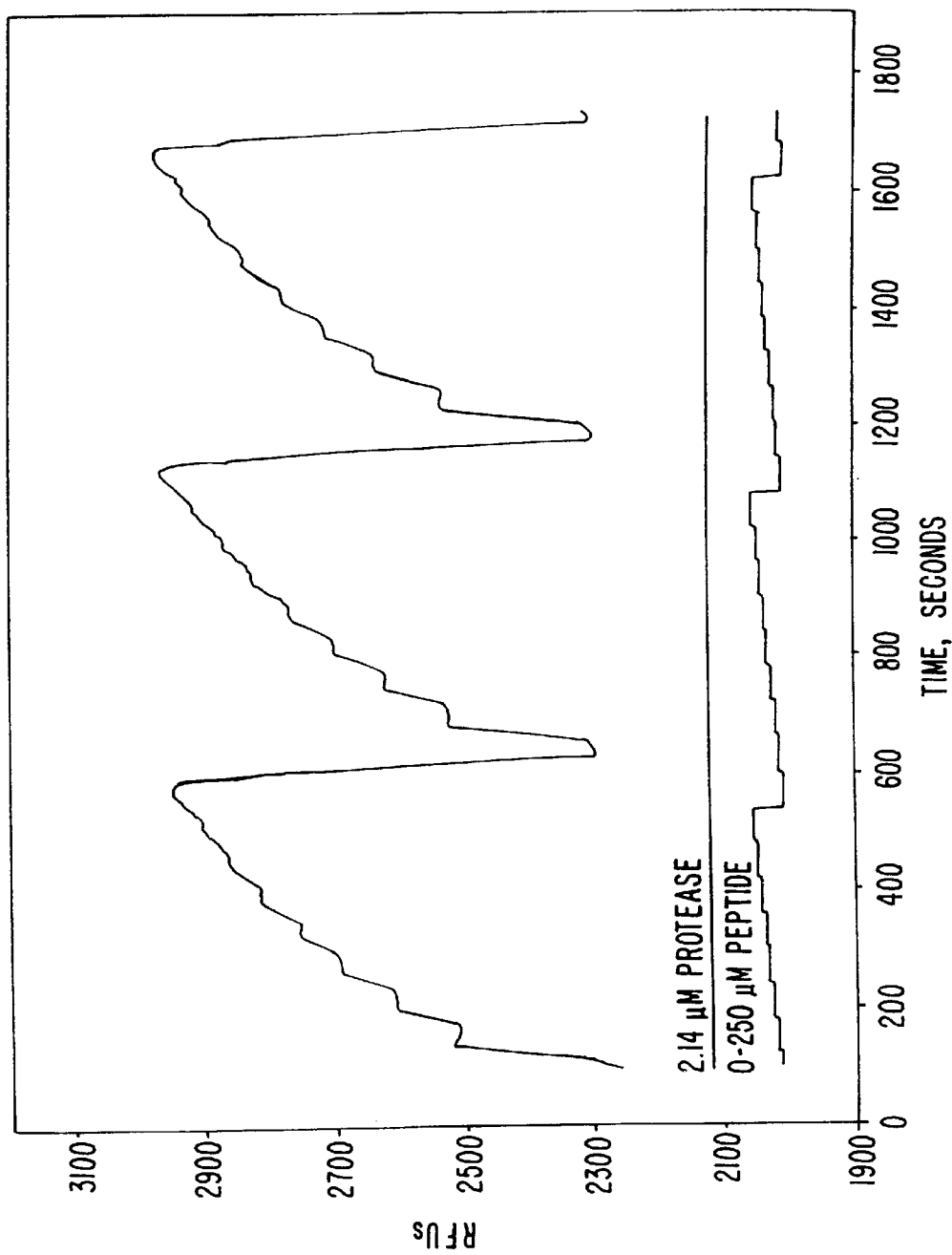
FIG. 19 is the raw data from an exemplar protease reaction on a microchip as a function of increasing FRET substrate concentration.

HCV protease was used in a similar fluorogenic assay to LAR phosphatase; however, the peptide substrate incorporates a fluorescence resonance energy transfer (FRET) label (FIG. 18). In order to verify that the depsipeptide/protease reaction was well behaved and the reaction parameters are in the range we expect, a continuous flow enzyme experiment with substrate titration was performed. FIG. 19 shows the fluorescence generated in a constant flow stream of 2.14 µM protease when various levels of depsipeptide are introduced, 0 to 250 µM depsipeptide. The product fluorescence is proportional to the amount of cleaved substrate. The height of the product signal is proportional to the rate of enzyme turnover for that substrate concentration. The rate of fluorescence generation can be assessed as the fluorescence signal per mixing time of substrate and enzyme in the reaction channel. That mixing time is determined by the mean residence time of the fluorescent product in the reaction channel as it is electrokinetically pumped from the source of the mixing to the detector. $K_m$ was determined from the Michaelis Menton equation.

Due to the chemistry of this FRET quenching reaction, several considerations for accurate measurement of $k_m$ on the Labchip™ exist. (1.) There is not an accurate calibration curve for the EDANS labeled product. (2) Accurate determination of the substrate concentration in the Labchip™ reagent well by a simple spectrophotometric measurement is not performed. (3) A gross approximation about the fluorescent efficiency of the EDANS-labeled peptide product was made relative to EDANS.

Figure 20:
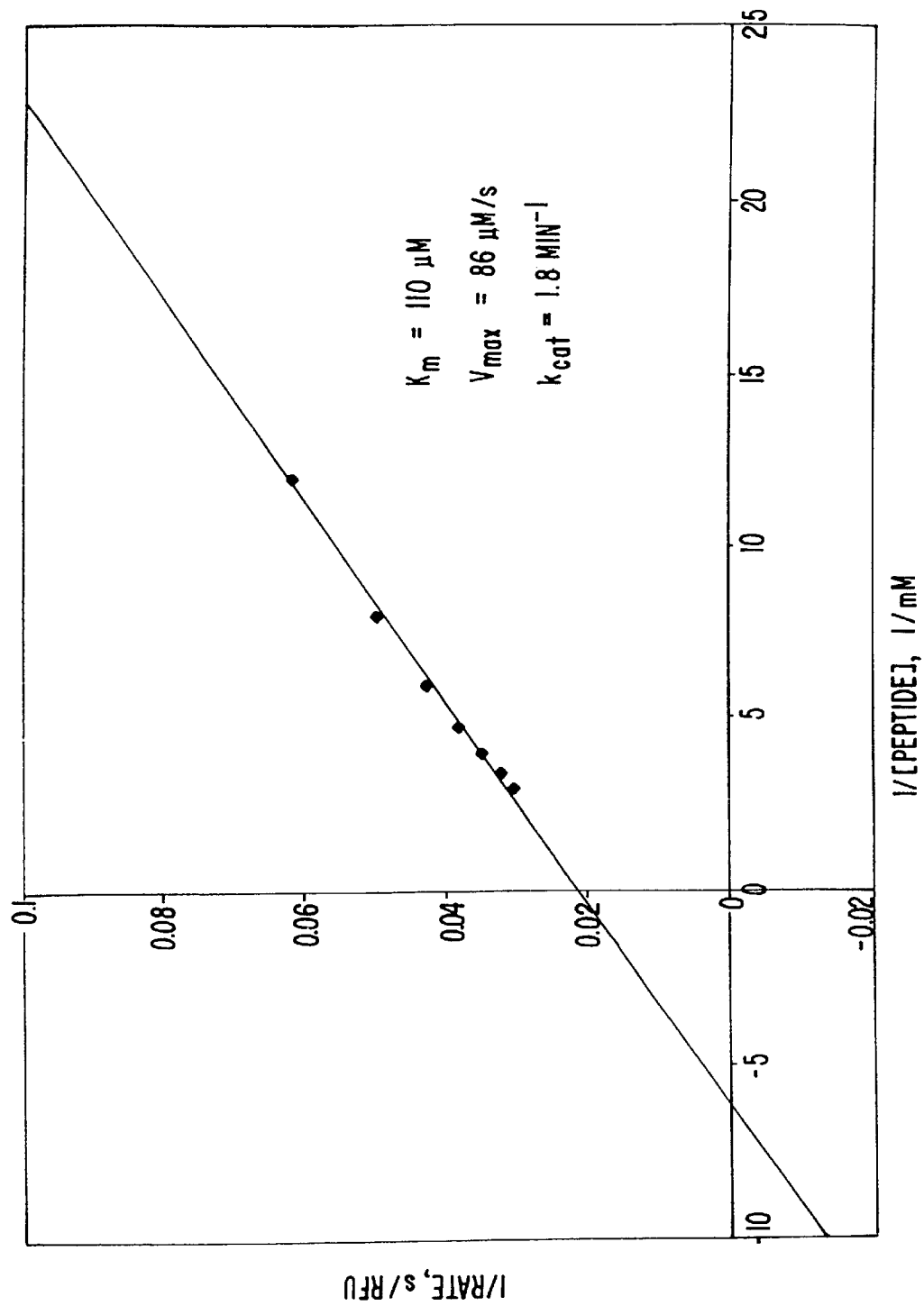
FIG. 20 is a Lineweaver Burke plot for determination of Km for the protease assay.

Despite these considerations, the data from FIG. 19 was converted to rate information and plotted as a function of the estimated depsipeptide concentration. The rate values were well behaved and the corresponding double reciprocal plot is shown in FIG. 20. In a Lineweaver-Burke plot, the slope of the line is $K_m/V_{max}$, the y-intercept is $1/V_{max}$ and the extrapolated -x intercept is $-1/K_m$. Values for $K_m$ and $k_{cat}$ derived from a least squares regression analysis of the points shown in FIG. 20 are summarized in Table 4 along with constants obtained using conventional analysis.

TABLE 4

Michaelis-Menten Constants Measured on a Labchip ™ and in cuvette for HCV protease and LAR Phosphatase

| | $K_m$ mM | $V_{max}$ mM/s | $k_{cat}$ min$^{-1}$ |
|---|---|---|---|
| HCV Protease/Depsipeptide Kinetics | | | |
| Chip | 0.11 | 0.086 | 1.8 |
| 25 mM TRIS/HCL, pH 8.5, 0.1% Triton X-100, 10 mM DTT, 1M NDSB-195 | | | |
| Cuvette | | | 46 |
| 50 mM TRIS/HCL, pH 7.5, 1.0% Triton X-100, 10 mM DTT, 1 *mm EDTA, 10 mM NaCl | | | |

TABLE 4-continued

Michaelis-Menten Constants Measured on a Labchip ™ and in cuvette for HCV protease and LAR Phosphatase

| | $K_m$ mM | $V_{max}$ mM/s | $k_{cat}$ min$^{-1}$ |
|---|---|---|---|
| HCV Protease/Depsipeptide Kinetics LAR/dFMUP Kinetics | | | |
| chip | 0.020–0.40 | 0.011 | 3000–5000 |
| 50 mM HEPES, pH 7.5, 10 mM DTT, 0.5M NDSB-195 | | | |

Note the buffer conditions for the Labchip™ analysis and the traditional analysis is different. Specifically, pH, surfactant concentration, and the presence of NDSB are known to influence the enzyme kinetics. Despite this, the agreement between the cuvette values and the Labchip™ kinetic constants is reasonable. Moreover, a comparison of the protease $k_{cat}$ with the phosphatase kinetic constants reveals the broad range of reaction rates we can expect to accommodate on the Lab-chip. It is possible to study the reaction kinetics of enzymes with three orders of magnitude difference in turnover rate on the same Labchip™.

Figure 21:
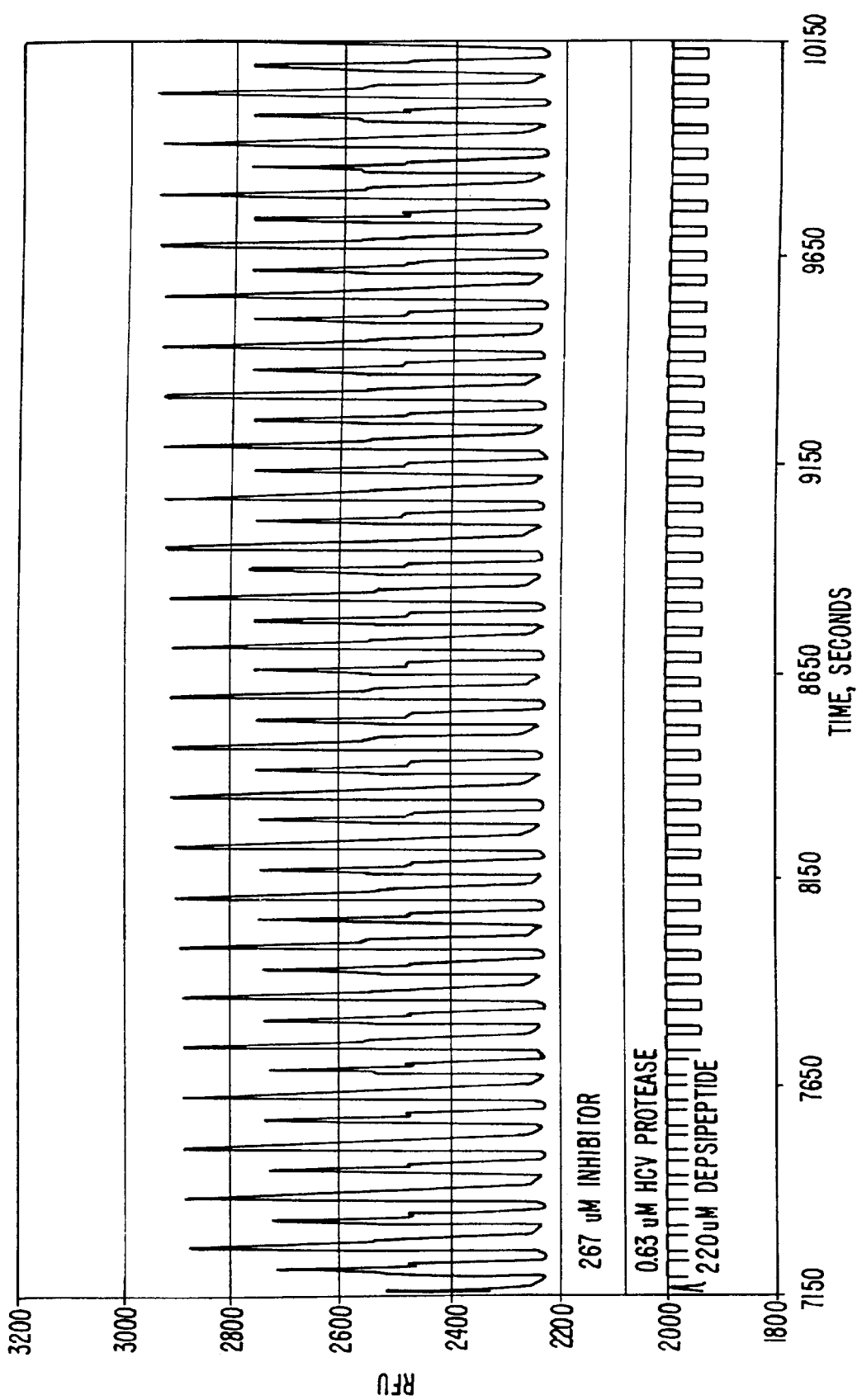
FIG. 21 is the third hour of a twelve-hour inhibition experiment for a continuous flow protease assay on a microchip.

A continuous flow experiment was performed to assess the Labchip™ lifetime for the enzyme assay for applications to high throughput screening. Since the sensitivity of the in vitro enzyme assay is depends on the enzyme concentration employed, in this experiment 0.63 µM HCV protease was continuously pumped through the reaction channel. Alternately, buffer for 40 seconds or 220 µM depsipeptide for 20 seconds was pumped into the flow stream such that the cycle time for each experiment was one minute. Every other substrate injection also contained 267 mM inhibitor. The reagents were loaded into reagent wells on the chip, the controller was initiated and the script was allowed to run uninterrupted for more than 12 hours. The raw data for the third hour of the experiment is shown in FIG. 21. As expected the inhibited response can be distinguished from the uninhibited substrate generated signal, and the peaks are separated by well behaved enzyme only blanks.

Figure 22:
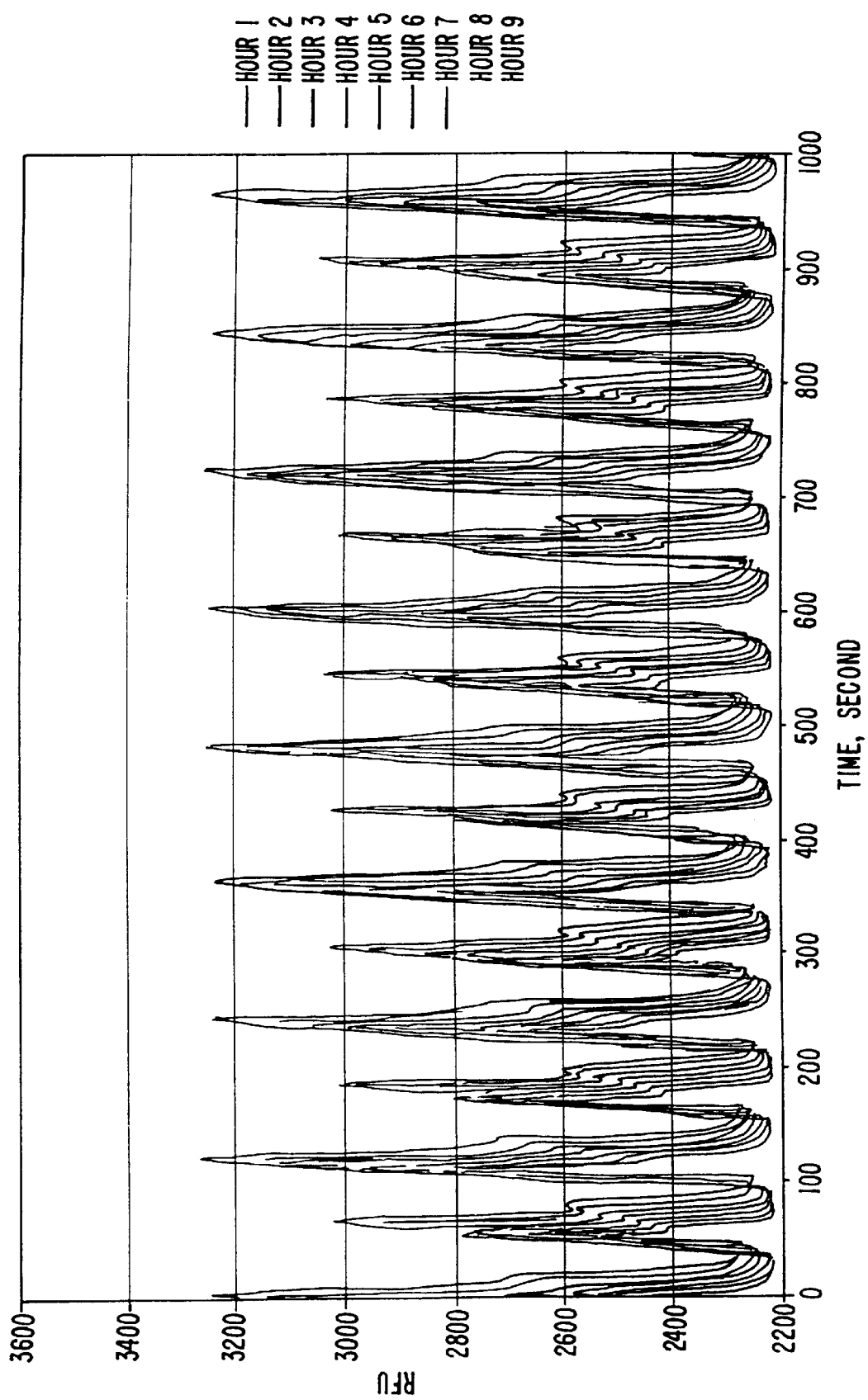
FIG. 22 is the raw data for the first 1000 seconds of each of the first nine hours of a protease reaction for the continuous flow inhibition assay.

The first 1000 seconds for each hour of the first nine hours of data is shown in FIG. 22. The background signal is very stable for this period of time. Note however that this well controlled background fluorescence is not the substrate only background. The extent of substrate hydrolysis over time could not be measured in the continuous flow analysis where enzyme was pumped throughout the course of the experiments. After nine hours the background increases and the assay no longer behaves reproducibly. The inhibition reaction is clearly seen for hours one through nine after which time the attenuation of the fluorescence response is not as great. Also the reproducible peak shapes for hours one through nine start to change after nine hours. The gradual delay in on time of inhibited and uninhibited peaks for each period of data is likely due to deterioration in EO flow. Enzyme adsorbing to the surface of the capillary can retard the electroosmotic flow, thereby increasing the incubation time of substrate and enzyme. This produces both the larger signals and longer mean response times observed here.

Figure 23:
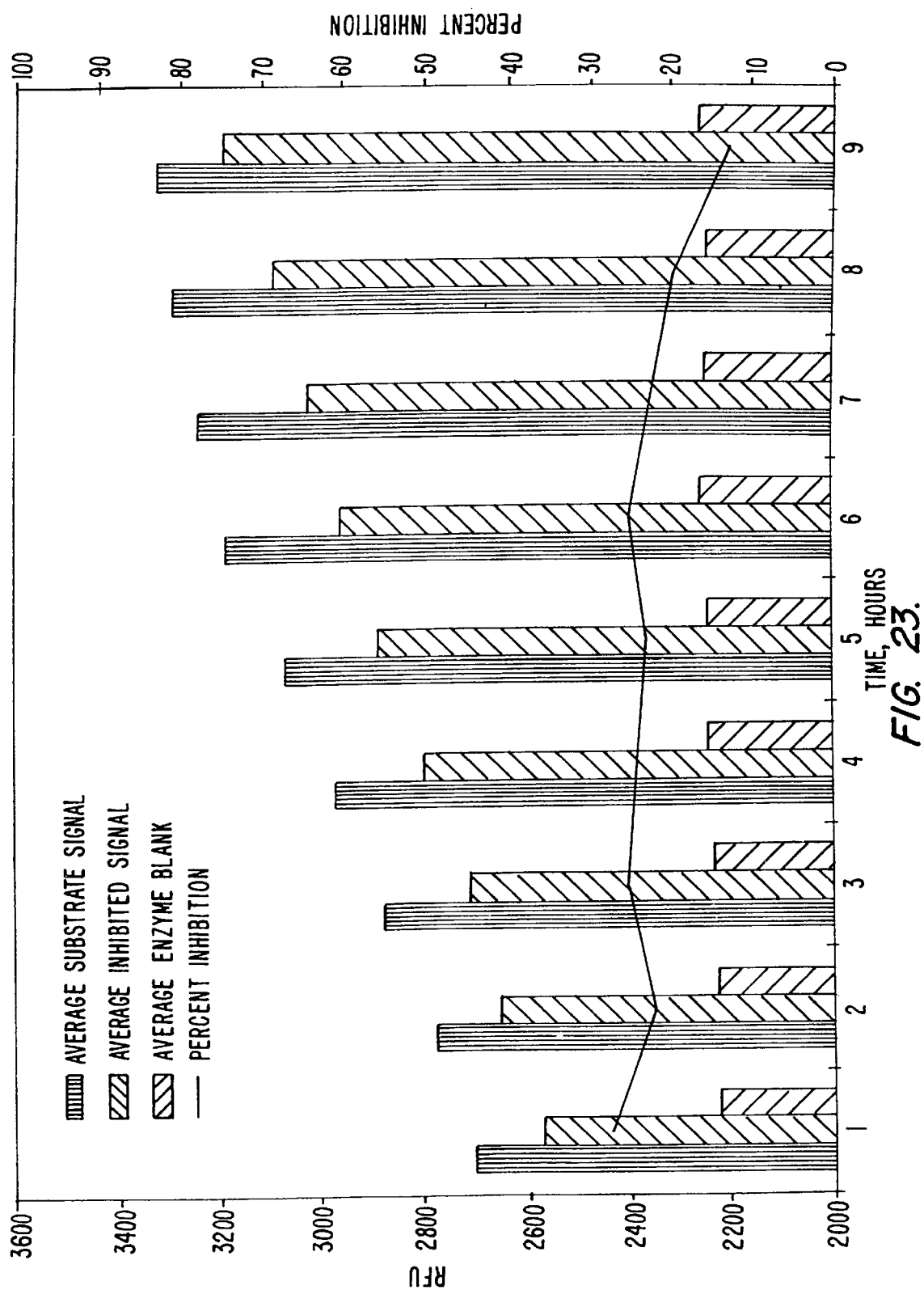
FIG. 23 is a summary of the inhibition observed for the first nine hours of the protease assay on a microchip.

The signals and percent inhibition for hours one through nine are summarized in FIG. 23. The chip was operational in that fluid was flowing for more than 12 hours of continuous electrokinetic pumping; however, the inhibition response was reproducible for seven hours. The total reagent volume consumed in the experiment can be calculated from the cross sectional area of the capillary and the total current.

For a 70 mm×20 mm channel and $I_{total}$ equal to 1.5 mA, the reagent volume consumed is 2.8 ml/hour or 33 ml in 12 hours. No effort was made to maximize the number of experiments in this time. Despite this fact, assuming each measurement is an individual experiment, a total of 1680 experiments were performed in seven hours. The average percent inhibition response was calculated for the first three inhibited and uninhibited signals at the start of each hour. The percent inhibition was 24+/−2% for the first seven hours of data.

Figure 24:
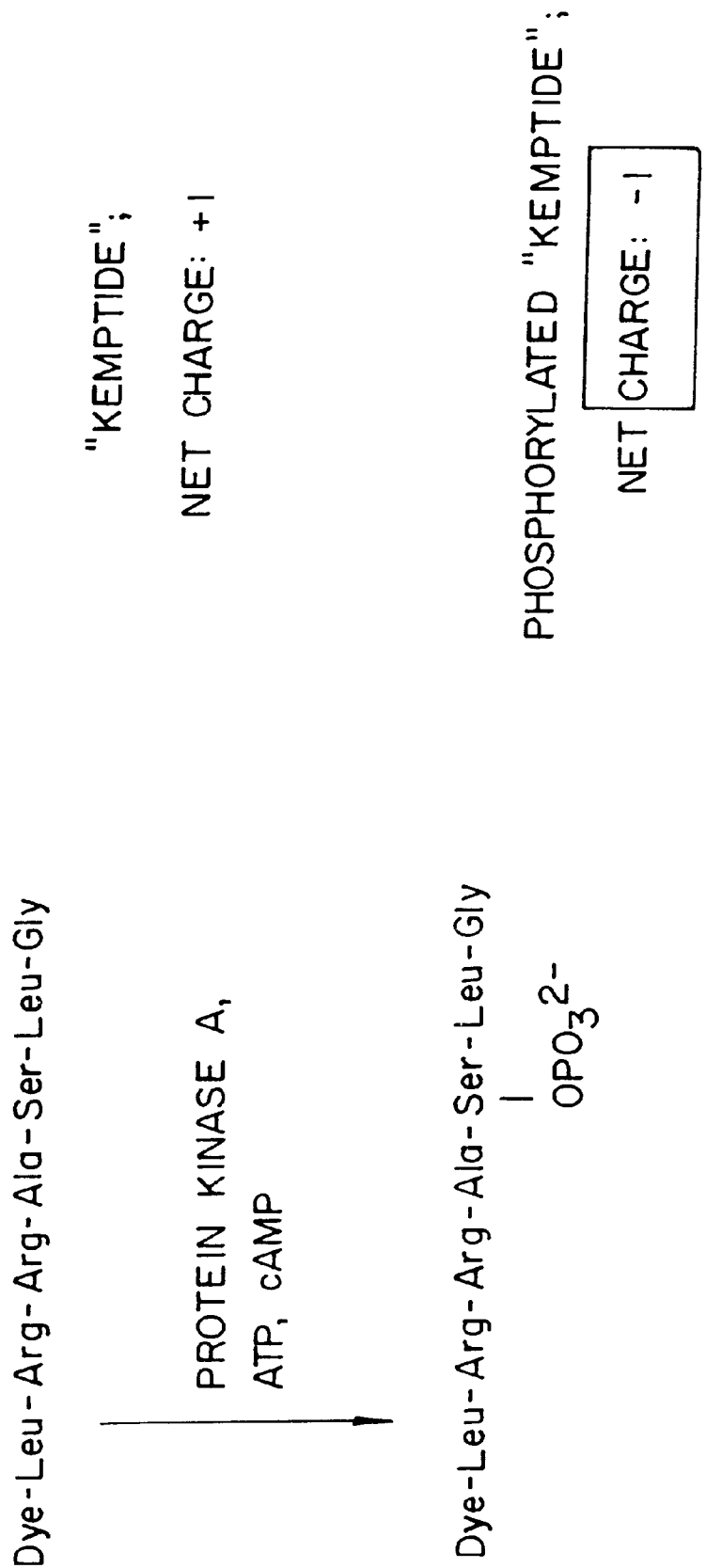
FIG. 24 is a schematic of an exemplar kinase reaction on a microchip.
Figure 25:
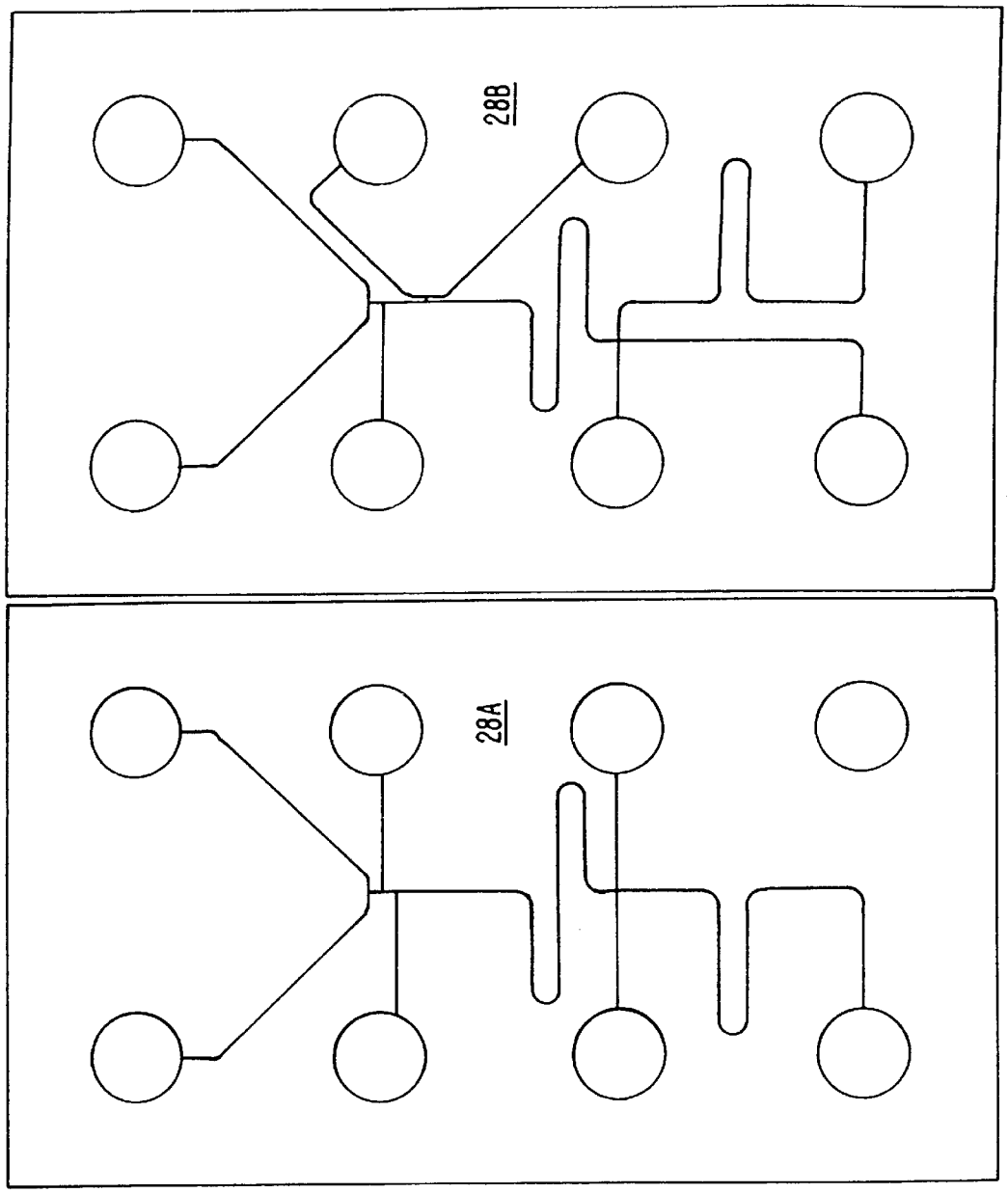
FIG. 25 is a schematic of microfluidic devices used in performing the non-fluorogenic kinase assays described herein (the "28A" and "28B" LABCHIPS™).

An example of a non-fluorogenic enzyme assay is depicted in FIG. 24. Here a protein kinase reaction is represented in which substrate is converted to product with differing mobility. Both substrate and product are fluorescently labeled and we rely on the separation of substrate and product following conversion to monitor the extent of reaction in a chip designed for mixing and incubation followed by separation, e.g. FIG. 25.

Figure 26B:
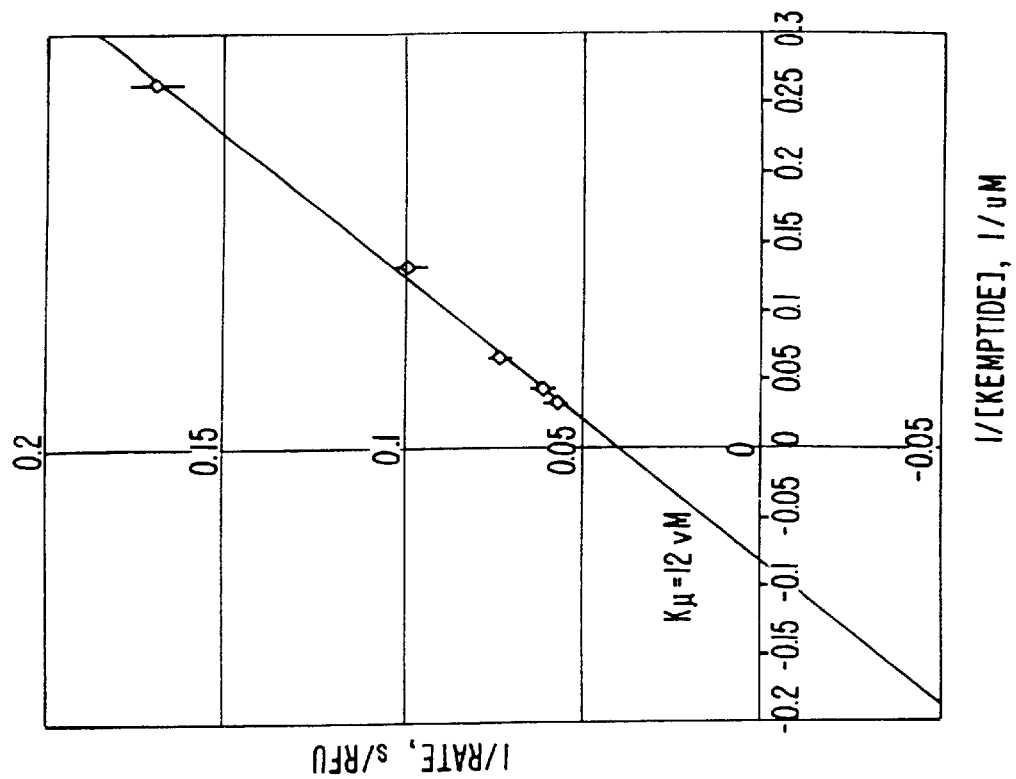
FIG. 26 is the fluorescence data and a Lineweaver Burke plot for the Km determination for PKA in a microchip.
Figure 26A:
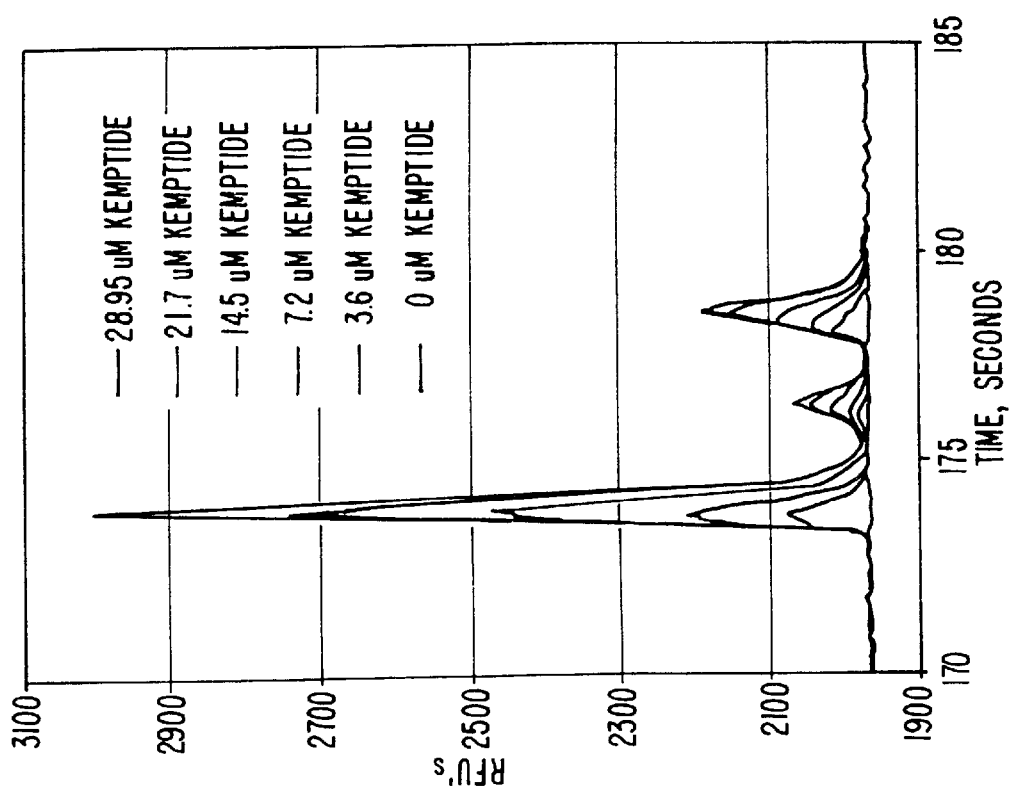

Similar to the phosphatase and protease, the kinase reactivity can by monitored in the microchip for kinetic analyses and applications to high throughput screening. FIG. 26 show the separated peaks due to substrate, dye marker, and product as a function of substrate concentration. The separation occurs following incubation of substrate and enzyme via a gated injection where the flux of substrate and product entering the separation channel is expected to accurately reflect the homogeneous reaction kinetics. The reaction conditions were 138 nM PKA in 100 mM Hepes, pH 7.5, 10 mM DTT, 5 mM MgCl2, 1M NDSB-195. The double reciprocal transformation is represented in a Lineweaver Burke plot, FIG. 26 and a Km of 12 uM is derived.

Figure 27:
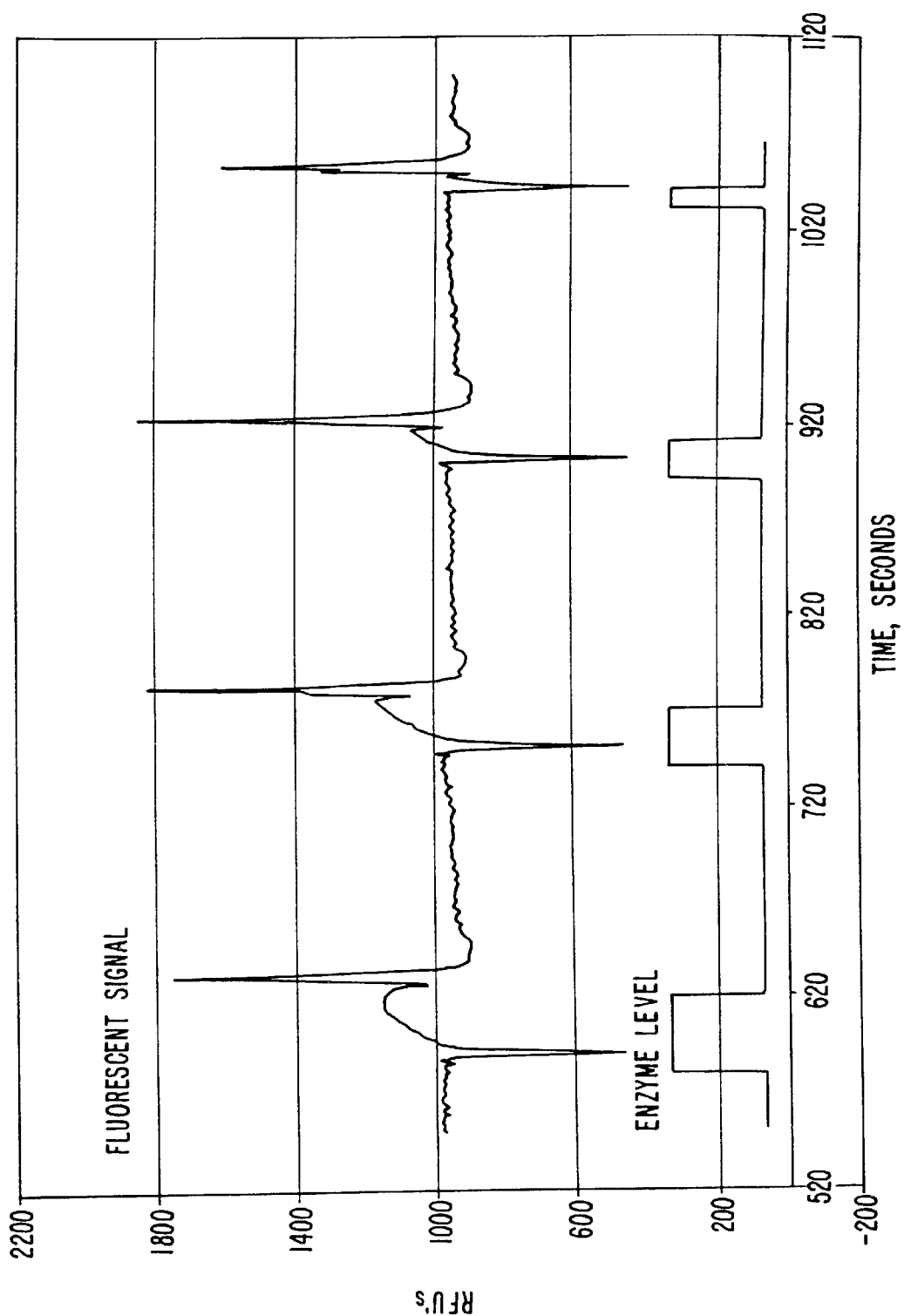
FIG. 27 is a fluorescence trace for the PKA assay demonstrating the mobility shift observed when enzyme is pulsed into a continuous stream of fluorescent substrate for various periods of time.

Non-fluorogenic assays can be designed in various other modes of operation. Among the strategies available are assays that modulate the enzyme concentration in a reaction channel containing a constant stream of fluorescent substrate. FIG. 27 contains the trace resulting from a constant stream of rhodamine-labeled-kemptide injected with PKA for 40, 30, 30 and 10 second periods. Because the product mobility is faster than the substrate mobility under this particular set of conditions, the trace shows a decrease in substrate concentration due to enzymatic consumption, followed by an increase in signal of concomitant area due to an accelerated rate of product generation. Displace substrate is turned over to product and appears as a peak in the fluorescent trace.

Figure 28:
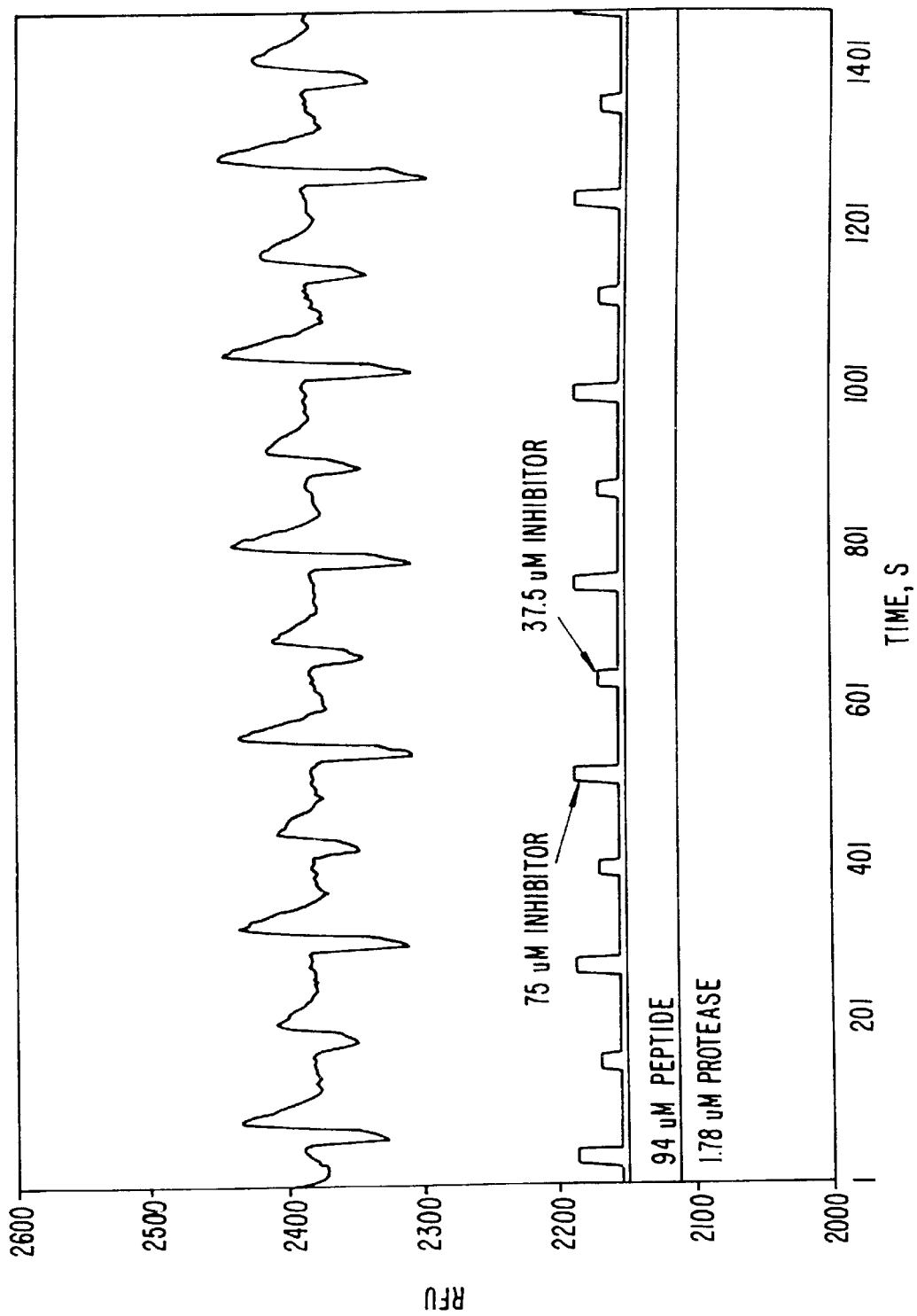
FIG. 28 is a fluorescence trace for the protease assay demonstrating the concentration dependent mobility shift observed when inhibitor is pulsed into a continuous stream of substrate and enzyme for two concentrations of inhibitor.
Figure 29:
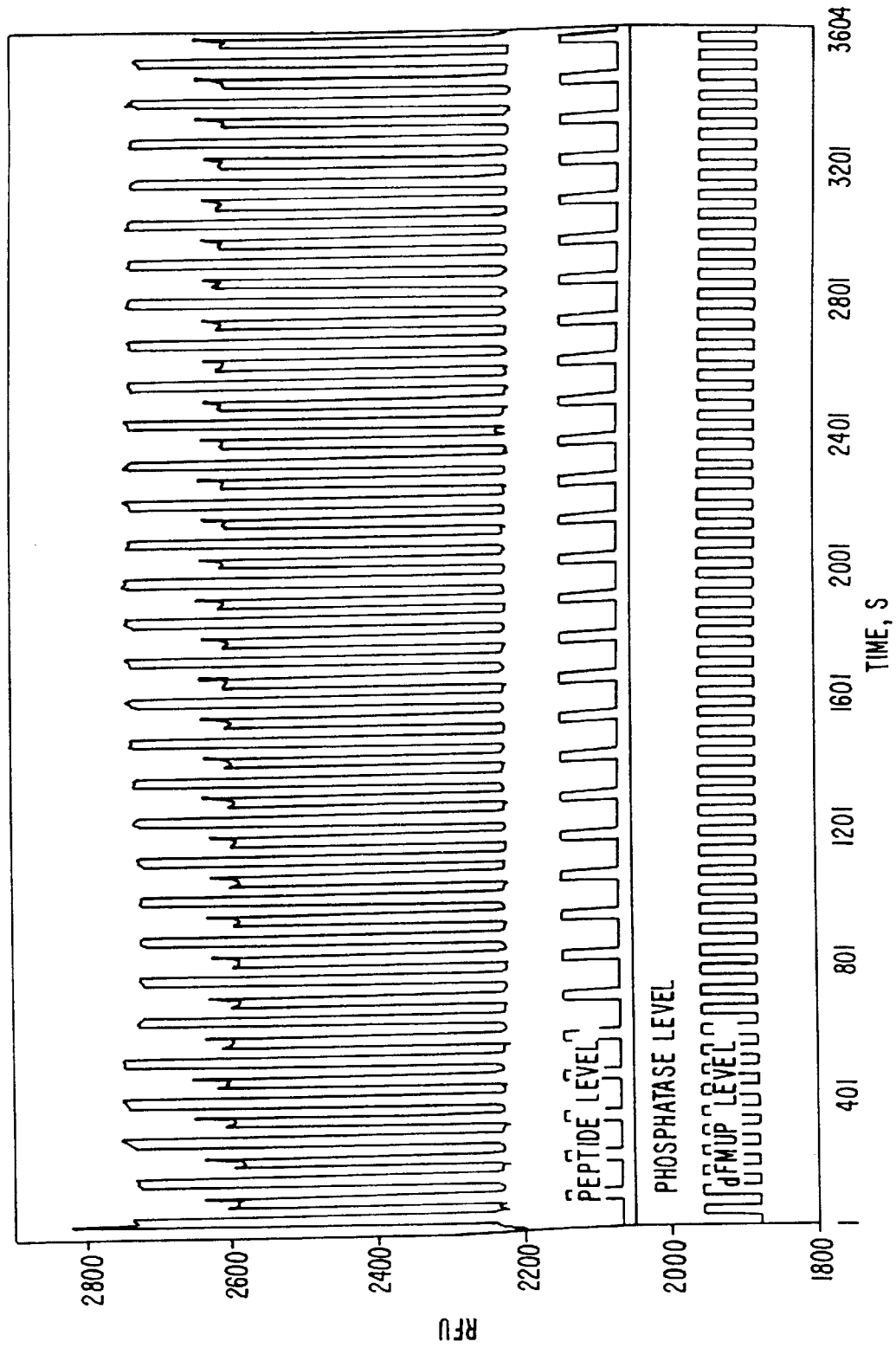
FIG. 29 is an extended time phosphatase assay (hour 3 of an 8 hour data run) with no reagent replacement.

In a similar way utilizing a fluorogenic reaction, here the protease reaction, constant fluorogenesis can be interrogated with pulses of inhibitor. An example is the protease and peptide substrate reaction. This is particularly relevant to high throughput screening systems in which continuously flowing enzyme and substrate are electrokinetically pumped through the reaction channel of the sipper chip and plugs of potential inhibitory compounds are injected. A decrease in the fluorescence signal should indicate inhibition for the compounds of interest. In an effort to simulate the high through put experiment on a planar chip, a constant fluorescence experiment was conducted. The reaction channel was continuously flowing 1.8 $\mu$M HCV Protease and 94 $\mu$M depsipeptide. Upon observation of the steady state fluorescence, inhibitor was injected into the flow stream at 75 $\mu$M and 37.5 $\mu$M for 20 s. The total cycle time for injections of two concentrations of inhibitor was 240 s. FIG. 28 shows the fluorescence trace for about 25 minutes.

Superimposed on the constant fluorescence signal is the inhibitor signature at two inhibitor concentrations. The higher inhibitor concentration gives rise to the larger dip followed by a peak. The lower inhibitor concentration yields a smaller dip followed by a comparable size peak. The dip and peak pairs are of similar area. We can rationalize these fluorescence responses.

The depsipeptide has six minus charges while the EDANS labeled product contains only two. Therefore we expected, based simply on the difference in charge, that the substrate should move more slowly in the flow stream than the product. During the time the enzyme "sees" inhibitor in the flow stream, the amount of fluorogenic substrate consumed is less than that during the uninhibited trace. If the slow moving substrate lags behind the inhibited response, an increase in the effective substrate concentration down stream from the inhibition will occur in the reaction channel. That higher substrate concentration can in turn generate a higher product concentration such that superimposed on the steady state fluorescence signal is a product peak. The similar area of dip and peak for each inhibitor concentration supports this rationale. The inhibitor concentration dependence of the signatures also supports this thinking. In light of the constant fluorescence in the absence of inhibitor it is likely that a similar experiment may be performed with shortened inhibitor injection times.

Modifications can be made to the method and apparatus as hereinbefore described without departing from the spirit or scope of the invention as claimed, and the invention can be put to a number of different uses, including:

The use of an integrated microfluidic system to test the effect of each of a plurality of reaction, assay or components test compounds in a biochemical or non-biochemical system, the system including data correction elements as described herein.

The use of a microfluidic system as hereinbefore described, wherein said biochemical system flows through one of said channels substantially continuously, enabling sequential testing of said plurality of test compounds, wherein the system includes provisions for data correction as described.

The use of a microfluidic system as hereinbefore described, wherein the provision of a plurality of reaction channels in said first substrate enables parallel exposure of a plurality of test compounds to at least one biochemical system, wherein the system includes provisions for data correction as described.

The use of a substrate carrying intersecting channels in screening test materials for effect on a biochemical system by flowing said test materials and biochemical system together using said channels wherein an apparatus utilizing the substrate includes provisions for data correction as described.

The use of a microfluidic substrate as hereinbefore described, wherein at least one of said channels has at least one cross-sectional dimension of range 0.1 to 500 $\mu$m.

The use of a system as described herein for nucleic acid sequencing, wherein the effects of the velocity of labeled components of a nucleic acid sequencing reaction are corrected for.

An assay, kit or system utilizing a use of any one of the microfluidic components, methods or substrates hereinbefore described. Kits will optionally additionally comprise instructions for performing assays or using the devices herein, packaging materials, one or more containers which contain assay, device or system components, or the like.

In an additional aspect, the present invention provides kits embodying the methods and apparatus herein. Kits of the invention optionally comprise one or more of the following: (1) an apparatus or apparatus component as described herein; (2) instructions for practicing the methods described herein, and/or for operating the apparatus or apparatus components herein, e.g., for correcting observed concentration for effects of velocity; (3) one or more assay component; (4) a container for holding apparatus or assay components, and, (5) packaging materials.

In a further aspect, the present invention provides for the use of any apparatus, apparatus component or kit herein, for the practice of any method or assay herein, and/or for the use of any apparatus or kit to practice any assay or method herein.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes, as if each reference were specifically indicated to be incorporated by reference.

What is claimed is:

1. A method of determining concentration of a reaction or assay product ($C_p$) in a microfluidic device, the method comprising:
    (i) converting a labeled first reactant or assay component having a velocity ($U_r$) and a label ($L_r$) and a concentration ($C_r$), the labeled first reactant or assay component producing a signal ($S_{as}$) in a signal detection system, to a reaction or assay product comprising a label $L_p$, having a velocity ($U_p$), wherein ($U_r$) does not equal ($U_p$);
    (ii) detecting a resulting change in $S_{as}$, which change is dependent on a difference between $U_p$ and $U_r$, wherein the change in $S_{as}$ correlates to a ratio of $U_r$ to $U_p$ or a ratio of $C_p$ to $C_r$; and,
    (iii) determining $C_p$ from the ratio of $C_p$ to $C_r$, or $U_r$ to $U_p$.

2. The method of claim 1, wherein the resulting change in $S_{as}$ is an indicator of $U_r$.

3. The method of claim 1, wherein $L_r$ comprises a fluorophore.

4. The method of claim 1, wherein the first reactant or assay component is contacted by a second reactant or assay component in a microfluidic channel in a first microfluidic channel region and wherein $S_{as}$ is detected by monitoring an output from a label detection device which is mounted to view a second microfluidic channel region in fluid communication with the first microfluidic channel region.

5. The method of claim 4, further comprising the step of injecting one or more fluorescent dyes or other flow markers into the microfluidic channel to generate a flow profile versus time mask file.

6. The method of claim 4, further comprising the step of injecting one or more labeled size markers into the microfluidic channel to generate a fluorescence intensity versus time mask file.

7. The method of claim 4, further deconvolution of a complex signal with a time mask file.

8. The method of claim 4, further comprising baseline subtraction by injecting a series of blanks into the microfluidic channel in a control experiment to measure a time dependent baseline.

9. The method of claim 4, further comprising injecting at least one flow marker into the microfluidic channel, sampling signal from a flow marker and generating a flow profile versus time mask file.

10. The method of claim 1, further comprising baseline subtraction of reactant signal ($S_r$) produced by the labeled first reactant from $S_{as}$ to provide a normalized signal ($S_n$) produced by the product.

11. The method of claim 1, wherein the step of converting the labeled first reactant or assay component to a reaction or assay product is performed by contacting the labeled first reactant or assay component with a second reactant or assay component to form a reaction or assay product comprising a label $L_p$ having a velocity ($U_p$), wherein ($U_r$) does not equal ($U_p$) and wherein $L_p$ comprises component elements of $L_r$.

12. The method of claim 1 wherein $L_p$ is formed from the components of $L_r$ by treating the first reactant with a label modifier selected from light, heat, electrical charge, a polymerization agent, and a catalyst.

13. The method of claim 1, wherein $L_p$ and $L_r$ comprise the same label moiety.

14. The method of claim 1, wherein $L_p$ and $L_r$ comprise different label moieties.

15. The method of claim 1, wherein the assay or reaction is in a continuous flow format.

16. The method of claim 1, wherein flux is conserved in the assay or reaction.

17. The method of claim 1, wherein the reaction or assay is a non-fluorogenic reaction or assay.

18. The method of claim 1, wherein the first reactant or assay component is contacted to the second reactant or assay component in a microfluidic channel.

19. The method of claim 1, wherein the first reactant flows down a first channel and the second reactant is periodically injected into the first channel to contact the first reactant.

20. The method of claim 1, wherein the first reactant or assay component flows down a first microfluidic channel and the second reactant or assay component is periodically injected into the first microfluidic channel, whereby the first reactant or assay component contacts the second reactant or assay component in the first microfluidic channel.

21. The method of claim 1, wherein the second reactant or assay component is injected into a microfluidic channel comprising the first reactant for a duration of from 0.001 to 10 min.

22. The method of claim 1, wherein the second reactant or assay component is reacted with the first reactant or assay component in a non-fluorogenic continuous flow mode.

23. The method of claim 1, wherein the first reactant or assay component comprises a moiety derived from an antibody, an antigen, a ligand, a receptor, an enzyme, an enzyme substrate, an amino acid, a peptide, a protein, a nucleoside, a nucleotide, a nucleic acid, a fluorophore, a chromophore, biotin, avidin, an organic molecule, a monomer, a polymer, a drug, a polysaccharide, a lipid, a liposome, a micelle, a toxin, a biopolymer, a molecule from a biological source, a blood constituent, or a cell.

24. The method of claim 1, wherein the first assay component is a component of a biological assay.

25. The method of claim 1, wherein the first assay component is a component of a non-biological assay.

26. The method of claim 1, wherein the first assay component is a component of a chemical synthetic reaction.

27. The method of claim 1, further comprising contacting the first or second reactant or assay component with at least one additional reactant.

28. The method of claim 1, further comprising the formation of at least one additional reactant or product.

29. The method of claim 1, further comprising determining the velocity of an additional reactant, assay component, or product.

30. The method of claim 1, further comprising the step of injecting a series of blanks into a channel comprising the first reactant to determine a time-dependent baseline.

31. The method of claim 1, wherein the first or second reactant or assay component is dissolved in an aqueous buffer.

32. The method of claim 1, wherein the first or second reactant or assay component is dissolved in an aqueous buffer having a pH between 3 and 11.

33. The method of claim 1, further comprising determining the flux for the first reaction component, the second reaction component and the product.

34. The method of claim 1, wherein the first reaction component and the second reaction component are mixed at a first pH which facilitates reaction of the first and second reaction component, wherein unreacted first component, unreacted second component or product are subsequently electrokinetically transported at a second pH which inhibits reaction of the first and second components.

35. The method of claim 1, wherein the first reaction component is an enzyme.

36. The method of claim 1, wherein the first reactant or assay component is an enzyme, the second reactant or assay component is a substrate and the product is formed by conversion of the substrate by the enzyme into the product.

37. The method of claim 1, wherein the first reactant or assay component and the second reactant or assay component hybridize to form the product, which product has a velocity faster than either the first component or the second component.

38. The method of claim 1, wherein the first reactant or assay component and the second reactant or assay component hybridize to form the product, which product has a velocity slower than either the first component or the second component.

39. The method of claim 1, further comprising measuring the concentration of the product spectrophotometrically, or optically.

40. The method of claim 1, wherein the first reactant or assay component and the second reactant or assay component comprise a ligand and a ligand binder, wherein the first component hybridizes to the second component.

41. The method of claim 1, wherein the first reactant or assay component and the second reactant or assay component comprise a ligand and a ligand binder wherein the first reactant or assay component hybridizes to the second reactant or assay component, and the ligand and ligand binder are selected from the group consisting of: a first nucleic acid and a second nucleic acid; an antibody and an antibody ligand; a receptor and a receptor ligand; biotin and avidin; a protein and a complementary protein; and, a carbohydrate and a carbohydrate binding moiety.

42. The method of claim 1, wherein the first reactant or assay component further comprising a biotin moiety, the second reactant or assay component further comprising a streptavidin moiety and the product further comprising the biotin moiety hybridized to the streptavidin moiety.

43. The method of claim 1, wherein the step of converting the labeled first reactant or assay component to a reaction or assay product is performed by contacting the labeled first reactant or assay component with a second reactant or assay component to form a reaction or assay product comprising a label $L_p$ having a velocity ($U_p$), wherein ($U_r$) does not equal ($U_p$) and wherein $L_p$ comprises component elements of $L_r$, wherein the first reactant or assay component and the second reactant or assay component are contacted in a microfluidic channel.

44. The method of claim 43, further comprising measuring the concentration of the product in a microfluidic channel, and, measuring the concentration of the first reaction or assay component in a portion of the microfluidic channel and, measuring the concentration of the second reaction or assay component in a portion of the microfluidic channel.

45. The method of claim 43, further comprising measuring a length of time for travel of the first reaction component or the second reaction component along a selected length of the microfluidic channel.

46. The method of claim 43, further comprising measuring a length of time for travel of the product along a selected length of the microfluidic channel.

47. The method of claim 43, wherein the first component, the second component, and the product are soluble in an aqueous solvent, wherein the microchannel comprises said aqueous solvent.

48. The method of claim 43, further comprising providing an electrokinetic microfluidic device having the microfluidic channel; and, applying an electric field along the length of the microchannel.

49. The method of claim 43, wherein the first and second component have a Ka (association constant) of between about $10^5$ and $10^{15}$.

50. The method of claim 1, wherein determining $C_p$ from the ratio of $C_r$ to $C_p$, or $U_r$ to $U_p$ comprises measuring the change in $S_{as}$ to determine the ratio of $U_r$ to $U_p$, measuring $C_r$ and solving for $C_p$ using the formula $C_p=C_r(U_r/U_p)$.

* * * * *

UNITED STATES PATENT AND TRADEMARK OFFICE
CERTIFICATE OF CORRECTION

PATENT NO.    : 6,524,790 B1                                                Page 1 of 1
DATED         : February 25, 2003
INVENTOR(S)   : Anne R. Kopf-Sill et al.

It is certified that error appears in the above-identified patent and that said Letters Patent is hereby corrected as shown below:

Column 49,
Line 36, replace "correlates to" with -- correlates with --.

Column 52,
Line 5, replace "the second" with -- a second --.
Line 42, replace "Ka" with -- $K_a$ --.

Signed and Sealed this

Fifth Day of August, 2003

JAMES E. ROGAN
*Director of the United States Patent and Trademark Office*